(12) United States Patent
Yedgar et al.

(10) Patent No.: US 11,013,811 B2
(45) Date of Patent: May 25, 2021

(54) LIPID-POLYMER CONJUGATES, THEIR PREPARATION AND USES THEREOF

(71) Applicant: YISSUM RESEARCH DEVELOPMENT COMPANY OF THE HEBREW UNIVERSITY OF JERUSALEM LTD., Jerusalem (IL)

(72) Inventors: Saul Yedgar, Jerusalem (IL); Yuval Cohen, Brooklyn, NY (US); Joseph V. Bondi, Collegeville, PA (US)

(73) Assignee: Yissum Research Development Company of the Hebrew University of Jerusalem Ltd., Jerusalem (IL)

( * ) Notice: Subject to any disclaimer, the term of this patent is extended or adjusted under 35 U.S.C. 154(b) by 0 days.

(21) Appl. No.: 14/525,111

(22) Filed: Oct. 27, 2014

(65) Prior Publication Data
US 2015/0119567 A1  Apr. 30, 2015

Related U.S. Application Data

(62) Division of application No. 12/997,014, filed as application No. PCT/US2010/034317 on May 11, 2010, now abandoned.

(60) Provisional application No. 61/177,083, filed on May 11, 2009.

(51) Int. Cl.
| | |
|---|---|
| *A61K 47/48* | (2006.01) |
| *A61K 31/728* | (2006.01) |
| *A61K 47/54* | (2017.01) |
| *A61K 31/727* | (2006.01) |
| *A61K 47/61* | (2017.01) |

(52) U.S. Cl.
CPC .......... *A61K 47/544* (2017.08); *A61K 31/727* (2013.01); *A61K 31/728* (2013.01); *A61K 47/61* (2017.08)

(58) Field of Classification Search
CPC ................ A61K 31/727; A61K 31/728; A61K 47/4823; A61K 47/48053
USPC ........................................................ 536/53
See application file for complete search history.

(56) References Cited

U.S. PATENT DOCUMENTS

| | | |
|---|---|---|
| 2,976,576 A | 3/1961 | Wichterle et al. |
| 3,220,960 A | 11/1965 | Wichterle et al. |
| 3,431,046 A | 3/1969 | Conrad et al. |
| 3,503,942 A | 3/1970 | Seiderman |
| 3,532,679 A | 10/1970 | Steckler |
| 3,542,461 A | 11/1970 | Girard et al. |
| 3,621,079 A | 11/1971 | Leeds et al. |
| 3,639,524 A | 2/1972 | Seiderman |
| 3,700,761 A | 10/1972 | O'Driscoll et al. |
| 3,721,657 A | 3/1973 | Seiderman |
| 3,758,448 A | 9/1973 | Stamberger |
| 3,772,235 A | 11/1973 | Stamberger |
| 3,786,034 A | 1/1974 | Blair et al. |
| 3,803,093 A | 4/1974 | Neefe et al. |
| 3,816,571 A | 6/1974 | O'Driscoll et al. |
| 3,875,211 A | 4/1975 | Steckler |
| 3,937,680 A | 2/1976 | de Carle |
| 3,940,207 A | 2/1976 | Barkdoll |
| 3,948,871 A | 4/1976 | Butterfield et al. |
| 3,949,021 A | 4/1976 | Kunitomo et al. |
| 3,983,083 A | 9/1976 | Kaetsu et al. |
| 3,988,274 A | 10/1976 | Masuhara et al. |
| 4,018,853 A | 4/1977 | Le Boeuf et al. |
| 4,055,378 A | 10/1977 | Feneberg et al. |
| 4,062,624 A | 12/1977 | Hammer |
| 4,064,086 A | 12/1977 | Cowsar et al. |
| 4,099,859 A | 7/1978 | Merrill |
| 4,604,376 A | 8/1986 | Teng |
| 4,624,919 A | 11/1986 | Kokusho et al. |
| 4,654,327 A | 3/1987 | Teng |
| 5,034,166 A | 7/1991 | Rawlings et al. |
| 5,064,817 A * | 11/1991 | Yedgar ............. A61K 47/48238 514/78 |
| 5,169,636 A | 12/1992 | Nanba et al. |
| 5,354,853 A | 10/1994 | Staveski et al. |
| 5,401,511 A | 3/1995 | Margalit |
| 5,401,777 A | 3/1995 | Ammon et al. |
| 5,464,942 A * | 11/1995 | Sakurai ............... C08B 37/0063 536/117 |
| 5,470,578 A | 11/1995 | Aoki et al. |
| 5,512,671 A | 4/1996 | Piantadosi et al. |
| 5,587,363 A | 12/1996 | Henderson |
| 5,707,821 A | 1/1998 | Rydel et al. |
| 5,719,656 A | 2/1998 | Bowling |
| 5,733,892 A | 3/1998 | Sakurai et al. |
| 5,785,975 A | 7/1998 | Parikh |
| 6,022,866 A | 2/2000 | Falk et al. |

(Continued)

FOREIGN PATENT DOCUMENTS

| | | |
|---|---|---|
| EP | 0236951 | 9/1987 |
| EP | 0581282 | 2/1994 |

(Continued)

OTHER PUBLICATIONS

Singh et al, Resonance, 1998, 56-60.*
Al-Turkmani MR .et al. 'Fatty acid alterations and n-3 fatty acid supplementation in cystic fibrosis', Prostaglandins, Leukotrienes and Essential Fatty Acids, 77, 309-318, 2007.
Albini, A, Iwamoto, Y, Kleinman, HK, Martin, GR, Aaronson, SA, Kozlowski, JM and McEwan, RN (1987) "A rapid in vitro assay for quantitating the invasive potential of tumor cells" Cancer Res 47(12):3239-45.
Balsinde, J. et al. 'Regulation and inhibition of phospholipase A2', Annu. Rev. Pharmacol. Toxicol. 39: 175-89, 1999.

(Continued)

Primary Examiner — Ganapathy Krishnan
(74) Attorney, Agent, or Firm — Alston & Bird LLP

(57) ABSTRACT

This invention provides low molecular weight lipid-GAG and phospholipids-GAG conjugates and methods of use thereof in suppressing, inhibiting, preventing, or treating a pathogenic effect on a cell, including, inter alia, infection with intracellular pathogens.

6 Claims, 35 Drawing Sheets

(56) References Cited

U.S. PATENT DOCUMENTS

| | | | |
|---|---|---|---|
| 6,043,231 A | 3/2000 | Pruzanski et al. | |
| 6,071,532 A | 6/2000 | Chaikof et al. | |
| 6,162,787 A | 12/2000 | Sorgente et al. | |
| 6,171,614 B1 | 1/2001 | Chaikof et al. | |
| 6,180,596 B1 | 1/2001 | Tsao | |
| 6,300,308 B1 | 1/2001 | Schroit et al. | |
| 6,211,162 B1 | 4/2001 | Dale et al. | |
| 6,325,385 B1 | 12/2001 | Iwashita et al. | |
| 6,444,660 B1 | 9/2002 | Unger et al. | |
| 6,654,460 B1 | 12/2003 | Benita et al. | |
| 6,749,813 B1 | 6/2004 | David et al. | |
| 7,014,860 B1* | 3/2006 | Kawata | A61L 24/0031 424/422 |
| 7,034,006 B2 | 4/2006 | Yedgar et al. | |
| 7,101,859 B2 | 9/2006 | Yedgar et al. | |
| 7,141,552 B2 | 11/2006 | Yedgar et al. | |
| 7,393,938 B2 | 7/2008 | Yedgar | |
| 7,893,226 B2* | 2/2011 | Yedgar | A61K 47/48053 536/18.7 |
| 2006/0189571 A1 | 8/2006 | Yedgar | |
| 2008/0109236 A1* | 5/2008 | DeAngelis | A61K 39/102 435/188.5 |
| 2008/0113935 A1 | 5/2008 | Yedgar et al. | |
| 2008/0193538 A1* | 8/2008 | Kitazono | A61L 27/20 424/488 |

FOREIGN PATENT DOCUMENTS

| | | |
|---|---|---|
| EP | 1046394 | 10/2000 |
| JP | 02345455 | 12/2002 |
| JP | 03160498 | 3/2003 |
| JP | 03335801 | 11/2003 |
| JP | 04018841 | 1/2004 |
| JP | 04170194 | 6/2004 |
| WO | WO 87/02777 | 5/1987 |
| WO | WO 91/00289 | 1/1991 |
| WO | WO 96/04001 | 2/1996 |
| WO | WO 96/28544 | 9/1996 |
| WO | WO 97/01330 | 1/1997 |
| WO | WO 97/48337 | 12/1997 |
| WO | WO 98/16198 | 4/1998 |
| WO | WO 98/51285 | 11/1998 |
| WO | WO 01/51003 | 7/2001 |
| WO | WO 01/91805 | 12/2001 |

OTHER PUBLICATIONS

Balsinde, J, Balboa, MA, Yedgar, S and Dennis, EA (2000) "Group V phospholipase A(2)-mediated oleic acid mobilization in lipopolysaccharide-stimulated P388D(1) macrophages" J Biol Chem 275(7):4783-6.

Beck, G, Yard, BA, Schulte, J, Oberacker, R, Van Ackern, K, Van Der Woude, FJ, Krimsky, M, Kaszkin, M and Yedgar, S (2002) "Inhibition of LPS-induced chemokine production in human lung endothelial cells by lipid conjugates anchored to the membrane" Br J Pharmacol 135(7):1665-74.

Brenner, T, Arnon, R, Sela, M, Abramsky, O, Meiner, Z, Riven-Kreitman, R, Tarcik, N and Teitelbaum, D (2001) "Humoral and cellular immune responses to Copolymer 1 in multiple sclerosis patients treated with Copaxone" J Neuroimmunol 115(1-2):152-60.

Brenner, T, Lisak, RP, Rostami, A, Pleasure, De and Silberberg, DH (1986) "Astrocytes, oligodendrocytes, and Schwann cells share a common antigenic determinant that cross-reacts with myelin basic protein: identification with monoclonal antibody" J Neurosci 6(7):1925-33.

Brenner, T, Poradosu, E, Soffer, D, Sicsic, C, Gazit, A and Levitzki, A (1998) "Suppression of experimental autoimmune encephalomyelitis by tyrphostin AG-556" Exp Neurol 154(2):489-98.

Cabanas, C and Hogg, N (1993) "Ligand intercellular adhesion molecule 1 has a necessary role in activation of integrin lymphocyte function-associated molecule 1" Proc Natl Acad Sci U S A 90(12):5838-42.

Carey et al, "Contrasting effects of cycloxygenase-1 (cox-1) and cox-2 deficiency in the host response to influenze, a viral infection". Journ. of Immunology 2005, vol. 15: 175 (10): 6878-84.

Carlstedt-Duke, et al. (1986), "Pathological regulation of arachidonic acid release in cystic fibrosis: The putative basic defect," Proceedings of the National Academy of Sciences, vol. 83, pp. 9202-9206.

Chen, WM, Soria, J, Soria, C, Krimsky, M and Yedgar, S (2002) "Control of capillary formation by membrane-anchored extracellular inhibitor of phospholipase A(2)" FEBS Lett 522(1-3):113-8.

Dan, P, Dagan, A, Krimsky, M, Pruzanski, W, Vadas, P and Yedgar, S (1998) "Inhibition of type I and type II phospholipase A2 by phosphatidyl-ethanolamine linked to polymeric carriers" Biochemistry 37(17):6199-204.

Darville, T, Yedgar, S, Krimsky, M, Andrews, CW, Jr., Jungas, T and Ojcius, DM (2004) "Protection against Chlamydia trachomatis infection in vitro and modulation of inflammatory response in vivo by membrane-bound glycosaminoglycans" Microbes Infect 6(4):369-76.

Davidson, FF, Dennis, EA, Powell, M and Glenney, JR, Jr. (1987) "Inhibition of phospholipase A2 by "lipocortins" and calpactins. An effect of binding to substrate phospholipids" J Biol Chem 262(4):1698-705.

Definition of prevention, Merriam-Webster Online Dictionary, retrieved Dec. 16, 2010.

Epelman, S., et al., (2000) "Pseudonomas aeruginosa Exoensyme S induces transcriptional expression of proinflammatory cytokines and chemokines" Infection and Immunity, vol. 68, No. 8, pp. 4811-4814.

Farooqui AA. et al. 'Inhibitors of intracellular phospholipase A2 activity: Their neurochemical effects and therapeutical importance for neurological disorders' , Brain Research Bulletin, vol. 49, No. 3, 139-153, 1999.

Freedman SD. et al. 'A membrane lipid imbalance plays a role in the phenotypic expression of cystic fibrosis in cftr −/− mice', PNAS vol. 96 No. 24: 13995-14000, Nov. 23, 1999.

Freedman SD. et al. Association of Cystic Fibrosis with Abnormalities in Fatty Acid Metabolism. NEJM, vol. 350: 560-569, Feb. 5, 2004.

Greaves MW and Camp RD (1988) "Prostaglandins, leukotrienes, phospholipase, platelet activating factor, and cytokines: an integrated approach to inflammation of human skin." Arch Dermatol Res 280:S33-41.

Kammouni W. et al. 'Altered Cytokine Production by Cystic Fibrosis Tracheal Gland Serous Cells', Infection and Immunity, p. 5176-5183, 1997.

Krimsky, M, Dagan, A, Aptekar, L, Ligumsky, M and Yedgar, S (2000) "Assessment of intestinal permeability in rats by permeation of inulin-fluorescein" J Basic Clin Physiol Pharmacol 11(2):143-53.

Krimsky, M, Yedgar, S, Aptekar, L, Schwob, O, Goshen, G, Gruzman, A, Sasson, S and Ligumsky, M (2003) "Amelioration of TNBS-induced colon inflammation in rats by phospholipase A2 inhibitor" Am J Physiol Gastrointest Liver Physiol 285(3):G586-92.

Kunzelmann et al, "Pharmacotherapy of the Ion Transport Defect in Cystic Fibrosis," Clin. Exper. Pharm. Phys. (2001) 28:857-67.

Margolis-Nunno, H, Ben-Hur, E, Gottlieb, P, Robinson, R, Oetjen, J and Horowitz, B (1996) "Inactivation by phthalocyanine photosensitization of multiple forms of human immunodeficiency virus in red cell concentrates" Transfusion 36(8):743-50.

Murthy, SN, Cooper, HS, Shim, H, Shah, RS, Ibrahim, SA and Sedergran, DJ (1993) "Treatment of dextran sulfate sodium-induced murine colitis by intracolonic cyclosporin" Dig Dis Sci 38(9):1722-34.

Okayasu, I, Hatakeyama, S, Yamada, M, Ohkusa, T, Inagaki, Y and Nakaya, R (1990) "A novel method in the induction of reliable experimental acute and chronic ulcerative colitis in mice" Gastroenterology 98(3):694-702.

Parish et al (Int. J. Cancer 1987 40: 511-518), "Evidence that sulphated polysaccharides inhibit tumour metastasis by blocking tumour-cell-derived heparanases."

Price, J.F. and Greally, P., "Corticosteroid treatment in cystic fibrosis," Arch Dis Child, 1993 68:719-721.

(56) References Cited

OTHER PUBLICATIONS

Schelstraete, P., et al., (2008), "Pseudonomas aeruginosa in the home environment of newly infected systic fibrosis patients," European Respiratory Journal, vol. 31, pp. 822-829.
Schmiel, DH and Miller, VL (1999) "Bacterial phospholipases and pathogenesis" Microbes Infect 1(13):1103-12.
Schnitzer, E, Dagan, A, Krimsky, M, Lichtenberg, D, Pinchuk, I, Shinar, H and Yedgar, S (2000) "Interaction of hyaluronic acid-linked phosphatidylethanolamine (HyPE) with LDL and its effect on the susceptibility of LDL lipids to oxidation" Chem Phys Lipids 104(2):149-60.
Schnitzer, E, Pinchuk, I, Fainaru, M, Lichtenberg, D and Yedgar, S (1998) "LDL-associated phospholipase A does not protect LDL against lipid peroxidation in vitro" Free Radic Biol Med 24(7-8):1294-303.
Schnitzer, E, Yedgar, S, Danino, D, Talmon, Y and Lichtenberg, D (1999) "The Interaction of hyaluronic-phosphatidylethanolamine with low density lipoprotein (LDL) and its effect on copper induced LDL oxidation" Biophysical Journal 76(1): Part 2.
Soeda S., et al., (Biochemistry 1990 29:5188-5194) "Tissue plasminogen activator catalyzed lys-plasminogen activation on heparin-inserted phospholipid liposomes".
Strandvik, B., Brönnegåd, M., Gilljam, H., Carlstedt-Duke, J., "Relation between Defective Regulation of Arachidonic Acid Release and Symptoms in Cystic Fibrosis," Scandinavian Journal of Gastroenterology, 1988, vol. 23, No. s143, pp. 1-4, Summary.
Strandvik B. et al 'Prostanoid biosynthesis in patients with cystic fibrosis. Prostaglandins, Leukotrienes and Essential Fatty Acids', 1996.
Teichgräber, V., (2008) "Ceramide accumulation mediates inflammation, cell death and infection susceptibility in cystic fibrosis," Nature Medicine, vol. 14, No. 4, pp. 382-391.
Teitelbaum D, Arnon R, Sela M, Rabinsohn Y, Shapiro D., "Sphingomyelin specific antibodies elicited by synthetic conjugates," Immunochemistry. Nov. 1973;10(11):735-43.
Van Biervliet S. et al 'Docosahexaenoic acid trials in cystic fibrosis: A review of the rationale behind the clinical trials', Journal of Cystic Fibrosis, 4, 27-34, 2005.
Vij N. et al. 'CHOP Transcription Factor Mediates IL-8 Signaling in Cystic Fibrosis Bronchial Epithelial Cells', Am. J. Respir Cell Mol Biol, vol. 38, 176-184, 2008.
Wang D.P, Matthias Schuster, Yi Fong Wang, Chi Huey Wong "Synthesis of phospholipid-inhibitor conjugates by enzymic transphosphatidylation with phospholipase", J. Am. Chem. soc.; 1993; 115(23); 10487-10491.
Welsh et al, "Molecular Mechanisms of CFTR Chloride Channel Dysfunction in Cystic Fibrosis," Cell (1993) 73:1251-54.
Weltzien HU, Matthiessen HP, Meyer-Delius M, Zimmermann F, Rüde E., "Acidic "peptidophospholipids", a new class of hapten-bearing cell surface modifying reagents," Mol Immunol. Sep. 1984;21(9):801-10.
Winger TM, Ludovice PJ, Chaikof EL, "Lipopeptide conjugates: biomolecular building blocks for receptor activating membrane-mimetic structures," Biomaterials. Feb. 1996;17(4):437-41.
Yard, BA, Yedgar, S, Scheele, M, Van Der Woude, D, Beck, G, Heidrich, B, Krimsky, M, Van Der Woude, FJ and Post, S (2002) "Modulation of IFN-gamma-induced immunogenicity by phosphatidylethanolamine-linked hyaluronic acid" Transplantation 73(6):984-92.
Yedgar, S, Lichtenberg, D and Schnitzer, E (2000) "Inhibition of phospholipase A(2) as a therapeutic target" Biochim Biophys Acta 1488(1-2):182-7.
Zar H. et al. 'Binding of pseudomonas aeruginosa to respiratory epithelial cells from patients with various mutations in the cystic fibrosis transmembrane regulator', Journal of Pediatrics, vol. 126, No. 2, Feb. 1995.
Wikipedia_Phosphatidylserine, Last modified on May 24, 2010, [Retrieved on Jun. 13, 2010]. Retrieved from the Internet: <URL: http://en.wikipedia.org/wiki/Phosphatidylserine>.
Wikipedia_Phosphatidylcholine, Last modified on Jun. 9, 2010, [Retrieved on Jun. 13, 2010]. Retrieved from the Internet: <URL: http://en.wikipedia.org/wiki/Phosphatidylcholine>.
Wikipedia_Phosphatidic acid, Last modified on Apr. 16, 2010, [Retrieved on Jun. 13, 2010]. Retrieved from the Internet: <URL: http://en.wikipedia.org/wiki/Phosphatidic_acid>.
Wikipedia_Polydispersity, [online]. Last modified on May 10, 2010, [Retrieved on Jun. 12, 2010]. Retrieved from the Internet: <URL: http://en.wikipedia.org/wiki/Polydispersity_Index>.
Search Report and Written Opinion of corresponding International application No. PCT/US10/34317 dated Jul. 20, 2010.
Mexican Office Action for Mexican Patent Application No. Mx/A2008/001639 dated May 2, 2013.
PCT/US2010/034317 International Preliminary Report on Patentability dated Nov. 15, 2011.

* cited by examiner

A: Cells plated and allowed to adhere.
B: Test Articles added.
C: LPS added.
D: Cell culture supernatants removed.

| Peak # | Time [min] | Area [μV·s] | Height [μV] | Area [%] | Norm. Area [%] | BL | Area/Height [s] |
|---|---|---|---|---|---|---|---|
| ~ | 7.000 | 0.00 | 0.00 | 0.00 | 0.00 | | |
| 1 | 7.480 | 30241017.54 | 457278.46 | 7.57 | 7.57 | *BV | 66.1326 |
| 2 | 10.738 | 66582570.86 | 394793.76 | 16.67 | 16.67 | *VV | 168.6515 |
| 3 | 12.984 | 94820267.76 | 2.11e+06 | 23.75 | 23.75 | *VV | 44.9951 |
| 4 | 13.628 | 68887133.84 | 1.97e+05 | 17.25 | 17.25 | *VE | 34.9416 |
| 5 | 15.146 | 241670.00 | 13902.28 | 0.06 | 0.06 | *EE | 17.3835 |
| 6 | 17.133 | 1.39e+08 | 709661.20 | 34.69 | 34.69 | *BB | 195.2153 |

| Peak # | Time [min] | Area [µV·s] | Height [µV] | Area [%] | Norm. Area [%] | BL | Area/Height [s] |
|---|---|---|---|---|---|---|---|
| | | 32773972.93 | 634045.56 | 7.45 | 7.45 | *BV | 51.6902 |
| | | 21884051.28 | 460511.28 | 4.98 | 4.98 | *VV | 47.5212 |
| | | 52201319.39 | 319662.04 | 11.87 | 11.87 | *VV | 163.3016 |
| | | 81252064.27 | 2.20e+06 | 18.48 | 18.48 | *VV | 36.9520 |
| | | 63353166.34 | 1.50e+06 | 14.41 | 14.41 | *VV | 42.2893 |
| | | 49402855.79 | 1.34e+06 | 11.23 | 11.23 | *VB | 36.7336 |
| | | 75664950.00 | 1.18e+06 | 17.21 | 17.21 | *BB | 64.3784 |
| | | 63240950.00 | 1.33e+06 | 14.38 | 14.38 | *BB | 47.5950 |

LIPID-POLYMER CONJUGATES, THEIR PREPARATION AND USES THEREOF

CROSS-REFERENCE TO RELATED APPLICATIONS

This application is a divisional application of pending U.S. patent application Ser. No. 12/997,014, filed on Dec. 9, 2010 as a National Phase Application of PCT International Application No. PCT/US10/34317, International Filing Date May 11, 2010, claiming priority of U.S. Provisional Application Ser. No. 61/177,083 filed May 11, 2009, all of which are hereby incorporated by reference.

FIELD OF THE INVENTION

This invention provides low molecular weight lipid-GAG conjugates and methods of use thereof in suppressing, inhibiting, preventing, or treating a pathogenic effect on a cell, including, inter alia, infection with intracellular pathogens.

BACKGROUND OF THE INVENTION

Lipid-conjugates having a pharmacological activity of inhibiting the enzyme phospholipase A2 (PLA2, EC 3.1.1.4) are known in the prior art. Phospholipase A2 catalyzes the breakdown of phospholipids at the sn-2 position to produce a fatty acid and a lysophospholipid. The activity of this enzyme has been correlated with various cell functions, particularly with the production of lipid mediators such as eicosanoid production (prostaglandins, thromboxanes and leukotrienes), platelet activating factor and lysophospholipids. Lipid-conjugates may offer a wider scope of protection of cells and organisms from injurious agents and pathogenic processes, including the prevention and treatment of microbial infections. Lipid-conjugates may offer a wider scope of protection of cells and organisms from injurious agents and pathogenic processes, including the prevention and treatment of microbial infections.

Lipid-conjugates have been subjected to intensive laboratory investigation in order to obtain a wider scope of protection of cells and organisms from injurious agents, pathogenic and inflammatory processes.

SUMMARY OF THE INVENTION

In one embodiment, the present invention provides a lipid-polymer conjugate comprising a glycosaminoglycan (GAG) conjugated to a phospholipid (PL) wherein said conjugate is prepared by reacting said GAG with said PL in a mass$_{PL}$ to mass$_{GAG}$ ratio from about 0.25:15 to about 5:15, respectively.

In one embodiment, the present invention provides a lipid-polymer conjugate comprising a glycosaminoglycan (GAG) conjugated to a phospholipid (PL) via an amide or ester linkage wherein the molecular weight of said GAG is between 5 to 20 kD.

In one embodiment, the present invention provides a lipid-polymer conjugate represented by the structure of the general formula (A):

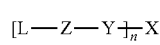

wherein
L is a lipid or a phospholipid;
Z is either nothing, ethanolamine, serine, inositol, choline, phosphate, or glycerol;
Y is either nothing or a spacer group ranging in length from 2 to 30 atoms;
X is a glycosaminoglycan; and
n is a number from 1 to 70;
wherein any bond between L, Z, Y and X is either an amide or an esteric bond;
wherein the molecular weight of said glycosaminoglycan is between 5 kD and 20 kD.

In one embodiment, the present invention provides a process for preparing a compound represented by the structure of the general formula (I):

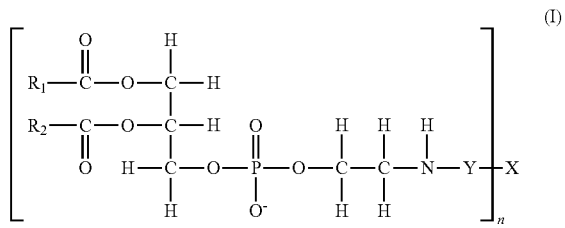

wherein
$R_1$ is a linear, saturated, mono-unsaturated, or poly-unsaturated, alkyl chain ranging in length from 2 to 30 carbon atoms;
$R_2$ is a linear, saturated, mono-unsaturated, or poly-unsaturated, alkyl chain ranging in length from 2 to 30 carbon atoms;
Y is either nothing or a spacer group ranging in length from 2 to 30 atoms;
X is a glycosaminoglycan; and
n is a number from 1 to 70;
wherein if Y is nothing the phosphatidylethanolamine is directly linked to X via an amide bond and if Y is a spacer, said spacer is directly linked to X via an amide or an esteric bond and to said phosphatidylethanolamine via an amide bond;
comprising the steps of:
b. reacting a phospholipid (PL) with a glycosaminoglycan (GAG) and a coupling agent, wherein the mass$_{PL}$ to mass$_{GAG}$ ratio from about 0.25:15 to about 5:15, respectively;
c. filtering the reaction mixture from (a) to generate a filtrate; and
d. extracting a product from a filtrate.

In one embodiment, the present invention provides a method of treating inflammatory disorders in a subject, said method comprising administering to a subject suffering from an inflammatory disorder a composition comprising a lipid-polymer conjugate comprising a glycosaminoglycan (GAG) conjugated to a phospholipid (PL) wherein said conjugate is prepared by reacting said GAG with said PL in a mass$_{PL}$ to mass$_{GAG}$ ratio from about 0.25:15 to about 5:15, respectively. In one embodiment, the present invention provides a method for decreasing expression of proinflammatory chemokines, cytokines, or a combination thereof comprising the step of administering a compound represented by the structure of the general formula (A):

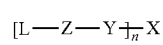

wherein

L is a lipid or a phospholipid;

Z is either nothing, ethanolamine, serine, inositol, choline, or glycerol;

Y is either nothing or a spacer group ranging in length from 2 to 30 atoms;

X is a glycosaminoglycan; and n is a number from 1 to 70;

wherein any bond between L, Z, Y and X is either an amide or an esteric bond to a subject with high levels of proinflammatory chemokines, cytokines, or a combination thereof.

In one embodiment, the present invention provides a method of activating NF-κB, IL-6, IL-8, or a combination thereof in human airway epithelial cell lines comprising the step of administering to a subject a compound represented by the structure of the general formula (A):

$$[L-Z-Y]_n X \qquad (A)$$

wherein

L is a lipid or a phospholipid;

Z is either nothing, ethanolamine, serine, inositol, choline, or glycerol;

Y is either nothing or a spacer group ranging in length from 2 to 30 atoms;

X is a glycosaminoglycan; and n is a number from 1 to 70;

wherein any bond between L, Z, Y and X is either an amide or an esteric bond.

BRIEF DESCRIPTION OF THE DRAWINGS

The subject matter regarded as the invention is particularly pointed out and distinctly claimed in the concluding portion of the specification. The invention, however, both as to organization and method of operation, together with objects, features, and advantages thereof, may best be understood by reference to the following detailed description when read with the accompanying drawings in which:

Figure 1:
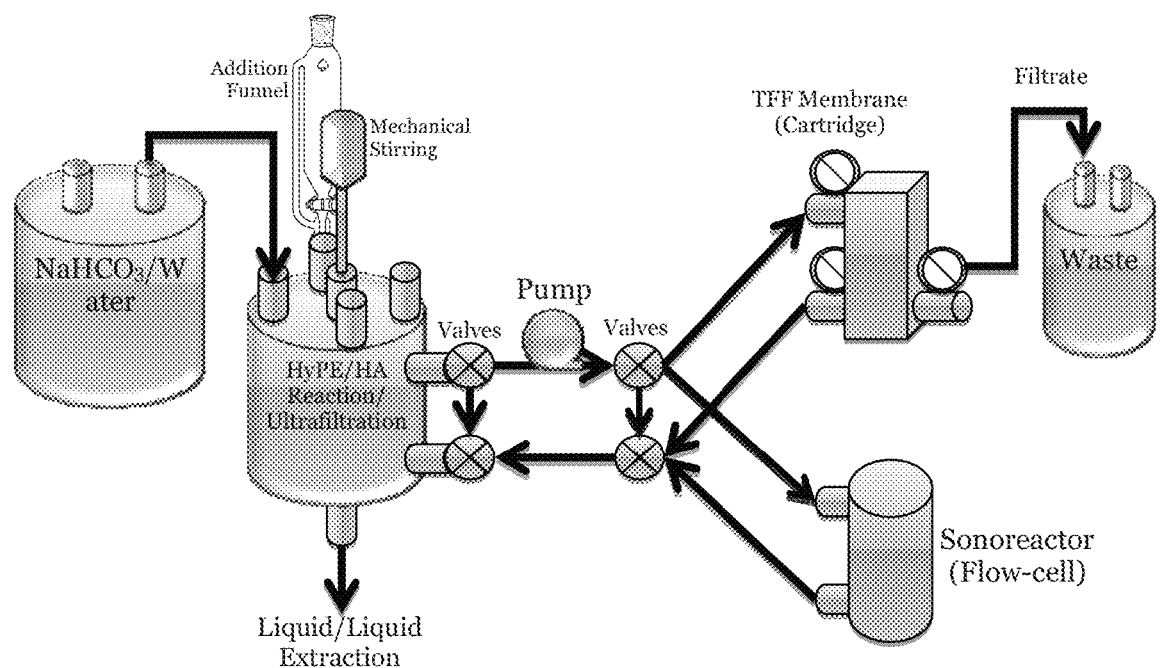
FIG. 1 depicts a conceptual diagram of the reaction vessel features required to practice the methods of this invention.

It will be appreciated that for simplicity and clarity of illustration, elements shown in the figures have not necessarily been drawn to scale. For example, the dimensions of some of the elements may be exaggerated relative to other elements for clarity. Further, where considered appropriate, reference numerals may be repeated among the figures to indicate corresponding or analogous elements.

DETAILED DESCRIPTION OF THE PRESENT INVENTION

In the following detailed description, numerous specific details are set forth in order to provide a thorough understanding of the invention. However, it will be understood by those skilled in the art that the present invention may be practiced without these specific details. In other instances, well-known methods, procedures, and components have not been described in detail so as not to obscure the present invention.

Abbreviations used to specify chemicals and reagents used in the processes described herein are readily recognized by one skilled in the art. For the purposes of this invention, it will be understood that DCC refers to dicyclohexylcarbodiimide, EDAC refers to 1-ethyl-3-(3-dimethylaminopropyl)carbodiimide hydrochloride), BOP refers to Benzotriazole-1-yl-oxy-tris-(dimethylamino)-phosphonium hexafluorophosphate, PyBOP refers to benzotriazol-1-yl-oxytripyrrolidinophosphonium hexafluorophosphate, HATU refers to O-(7-Azabenzotriazole-1-yl)-N,N,N',N'-tetramethyluronium hexafluorophosphate, TSTU refers to O—(N-Succinimidyl)-N,N,N',N'-tetramethyluronium tetrafluoroborate, HO-BT refers to hydroxybenzotriazole and HOAT refers to 1-hydroxy-7-aza-benzotriazole.

Herein, the term "lipid" refers to all types of lipids including phospholipids, glycerolipids, sphingolipids, sterol lipids, prenol lipids, saccharolipids and the like.

This invention provides, in one embodiment, a lipid-polymer conjugate which is useful in some embodiments for the treatment of inflammatory disorders.

In some embodiments, this invention provides a method for the preparation of the lipid-polymer conjugates of this invention. In some embodiments, this invention provides a method for the use of the lipid-polymer conjugates of this invention.

In one embodiment, this invention provides a lipid-polymer conjugate comprising a glycosaminoglycan (GAG) conjugated to a phospholipid (PL) wherein said conjugate is prepared by reacting said GAG with said PL in a $mass_{PL}$ to $mass_{GAG}$ ratio from about 0.25:15 to about 5:15, respectively.

In another embodiment, said $mass_{PL}$ to $mass_{GAG}$ ratio is about 0.25:15. In another embodiment, said $mass_{PL}$ to $mass_{GAG}$ ratio is about 0.5:15. In another embodiment, said $mass_{PL}$ to $mass_{GAG}$ ratio is about 1:15. In another embodiment, said $mass_{PL}$ to $mass_{GAG}$ ratio is about 2:15. In another embodiment, said $mass_{PL}$ to $mass_{GAG}$ ratio is about 5:15.

In one embodiment, the present invention provides a lipid-polymer conjugate comprising a glycosaminoglycan (GAG) conjugated to a phospholipid (PL) via an amide or ester linkage wherein the molecular weight of said GAG is between 5 to 20 kD.

In another embodiment, said GAG of the lipid-conjugate compound of this invention is hyaluronic acid, heparin, heparan sulfate, chondroitin, chondroitin sulfate, dermatan sulfate or keratan sulfate. In another embodiment, said GAG is hyaluronic acid. In another embodiment, said GAG is heparin. In another embodiment, said GAG is chondroitin. In another embodiment, said GAG is chondroitin sulfate. In another embodiment, said GAG is dermatan sulfate, in another embodiment, said GAG is keratan sulfate.

In another embodiment, said chondroitin sulfate is chondroitin-6-sulfate, chondroitin-4-sulfate or a derivative thereof. In another embodiment, said dermatan sulfate is dermatan-6-sulfate, dermatan-4-sulfate or a derivative thereof.

In another embodiment, said PL of the lipid-conjugate compound of this invention is a phosphatidylethanolamine, a phosphatidylserine, a phosphatidylcholine, a phosphatidylinositol, a phosphatidic acid or a phosphatidylglycerol. In another embodiment, said PL comprises the residue of palmitic acid, myristic acid, myristoleic acid, palmitoleic acid, oleic acid, linoleic acid, linolenic acid, arachidonic acid, eicosapentaenoic acid, erucic acid or docosahexaenoic acid. In another embodiment, said PL is dimyristoyl phosphatidylethanolamine In another embodiment, said PL is dipalmitoyl phosphatidylethanolamine.

In another embodiment, the polydispersity of said GAG is from about 1 to 1.75. In another embodiment, the polydispersity of said GAG is from about 1.25 to 1.5.

In one embodiment, the lipid-polymer conjugate of this invention comprises a GAG wherein the average molecular weight of said GAG is between 5 kd to 90 kd. In another embodiment, the average molecular weight of said GAG is between 5 kD to 60 kD. In another embodiment, the average molecular weight of said GAG is between 5 kD to 40 kD. In another embodiment, the average molecular weight of said GAG is between 5 kD to 15 kD. In another embodiment, the average molecular weight of said GAG is between 5 kD to 20 kD.

In one embodiment, low molecular weight GAG, such as sodium hyaluronate is prepared by acid hydrolysis of sodium hyaluronate as described in Example 9. In another embodiment, said acid hydrolysis comprises hydrochloric acid. In another embodiment, said acid hydrolysis comprises sulfuric acid. In another embodiment, said acid hydrolysis comprises trifluoroacetic acid. In another embodiment, said acid hydrolysis comprises hydrobromic acid. In another embodiment, said acid hydrolysis comprises acetic acid. In another embodiment, the concentration of the acid in said acid hydrolysis is from about 0.1 to 12 molar. In another embodiment, the concentration of the acid in said acid hydrolysis is from about 1 to 6 molar. In another embodiment, the concentration of the acid in said acid hydrolysis is from about 6 to 12 molar. In another embodiment, said acid hydrolysis is carried out at a temperature between 25 degrees Celsius to 100 degrees Celsius. In another embodiment, said acid hydrolysis is carried out at a temperature between 25 degrees Celsius to 50 degrees Celsius. In another embodiment, said acid hydrolysis is carried out at a temperature between 50 degrees Celsius to 100 degrees Celsius.

Figure 19:
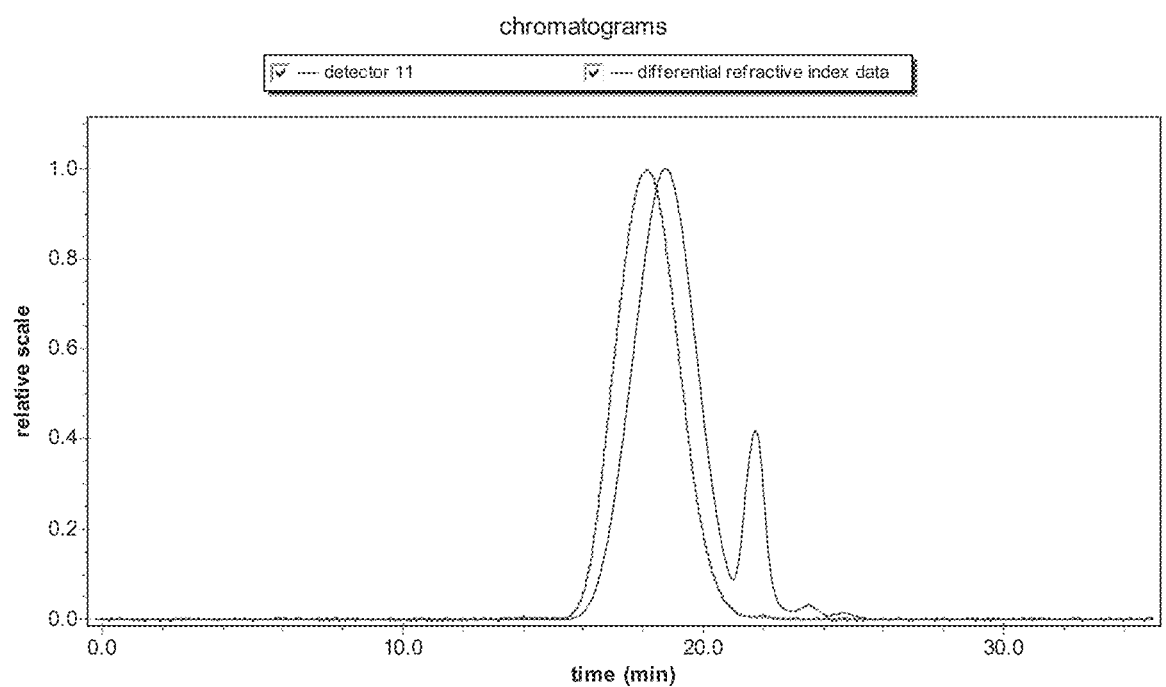
FIG. 19 is the chromatogram from the SEC-MALS molecular weight analysis of low molecular weight sodium hyaluronate. The red line pertains to the light scattering signal. The blue line refers to the refractive index signal.
Figure 20:
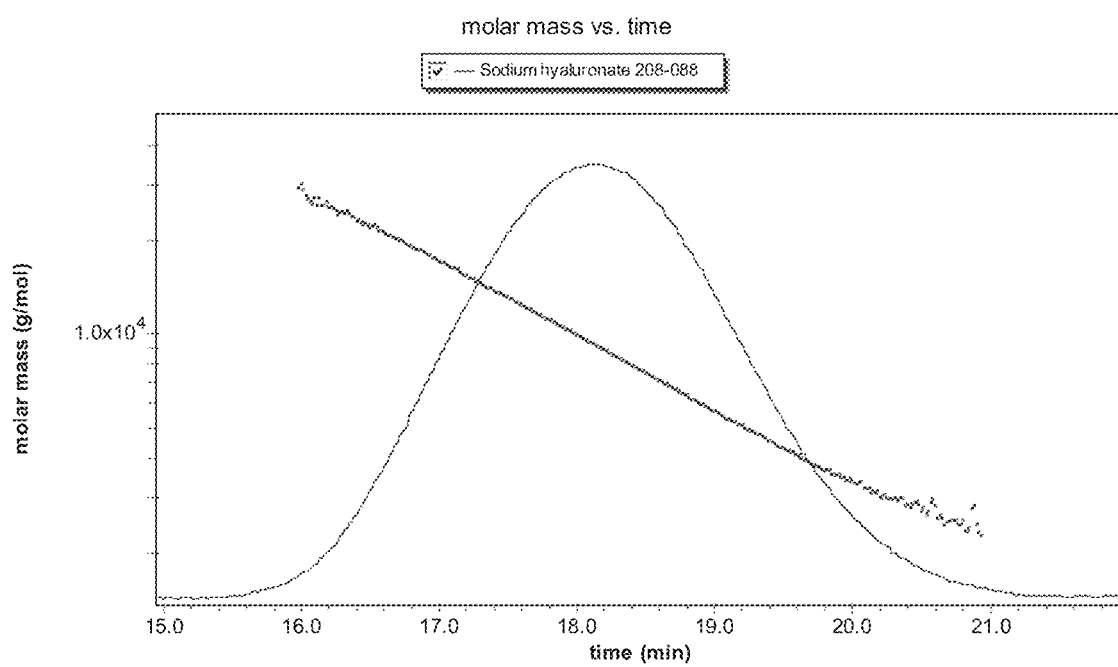
FIG. 20 is the SEC-MALS determined distribution of molecular weight of low molecular weight sodium hyaluronate.
Figure 21:
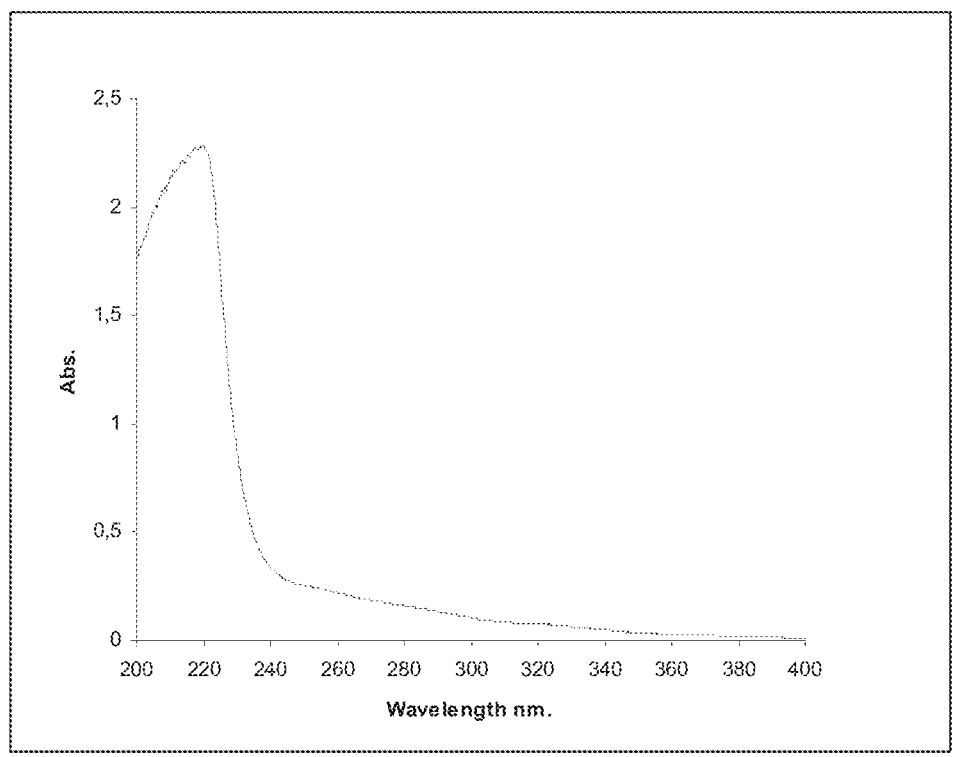
FIG. 21 is the UV spectrum of sample 208-088 (low molecular weight sodium hyaluronate).

In one embodiment the molecular weight of hyaluronic acid and derivatives is determined by size exclusion chromatography and multiangle light scattering (SEC-MALS) as described in Example 10. The chromatogram and distribution diagram are stated in FIG. 19 and FIG. 20 whereas the red line pertains to light scattering signal and the blue line to refractive index signal. FIG. 21 illustrates the UV spectrum.

Light scattering measurements can provide an absolute measurement of molar mass when used in series with a concentration sensitive detector such as a refractive index detector and if the value of dn/dc (differential refractive index increment) is known. In essence, light scattering measurements automatically provide a column calibration curve for every sample, obviating time-consuming, conformation dependent calibration procedure.

In one embodiment, the hyaluronan samples for SEC-MALS molecular weight determination are prepared by dissolving of a weighted amount of sample in a phosphate buffer. In another embodiment, the hyaluronan samples for SEC-MALS molecular weight determination are prepared by dissolving of a weighted amount of sample in an acetate buffer. In another embodiment, the hyaluronan samples for SEC-MALS molecular weight determination are prepared by dissolving of a weighted amount of sample in a tris buffer. In another embodiment, the hyaluronan samples for SEC-MALS molecular weight determination are prepared by dissolving of a weighted amount of sample in a MES buffer.

In another embodiment, this invention provides a pharmaceutical composition comprising a lipid-polymer conjugate comprising a glycosaminoglycan (GAG) conjugated to a phospholipid (PL) wherein said conjugate is prepared by reacting said GAG with said PL in a mass$_{PL}$ to mass$_{GAG}$ ratio from about 0.25:15 to about 5:15, respectively. In another embodiment, the average molecular weight of said GAG is between 5 kD to 90 kD. In another embodiment, the average molecular weight of said GAG is between 5 kD to 20 kD. In another embodiment, the average molecular weight of said GAG is greater than 10 kD.

In one embodiment, this invention provides a lipid-polymer conjugate represented by the structure of the general formula (A):

(A)

wherein
L is a lipid or a phospholipid;
Z is either nothing, ethanolamine, serine, inositol, choline, phosphate, or glycerol;
Y is either nothing or a spacer group ranging in length from 2 to 30 atoms;
X is a glycosaminoglycan; and
n is a number from 1 to 70;
wherein any bond between L, Z, Y and X is either an amide or an esteric bond;
wherein the molecular weight of said glycosaminoglycan is between 5 kD and 20 kD.

In one embodiment L is a lipid. In another embodiment L is a phospholipid. In another embodiment, L is a phosphatidylethanolamine, a phosphatidylserine, a phosphatidylcholine, a phosphatidylinositol, a phosphatidic acid or a phosphatidylglycerol. In another embodiment, L comprises the residue of palmitic acid, myristic acid, myristoleic acid, palmitoleic acid, oleic acid, linoleic acid, linolenic acid, arachidonic acid, eicosapentaenoic acid, erucic acid or docosahexaenoic acid. In another embodiment, L is dimyristoyl phosphatidylethanolamine. In another embodiment, said L is dipalmitoyl phosphatidylethanolamine.

In another embodiment, X is hyaluronic acid, heparin, heparan sulfate, chondroitin, chondroitin sulfate, dermatan sulfate or keratan sulfate. In another embodiment, X is hyaluronic acid. In another embodiment, X is heparin. In another embodiment, X is chondroitin. In another embodiment, X is chondroitin sulfate. In another embodiment, X is dermatan sulfate, in another embodiment, X is keratan sulfate.

In another embodiment, said chondroitin sulfate is chondroitin-6-sulfate, chondroitin-4-sulfate or a derivative thereof. In another embodiment, said dermatan sulfate is dermatan-6-sulfate, dermatan-4-sulfate or a derivative thereof.

In another embodiment, said lipid-polymer conjugate is represented by the structure of the general formula (I):

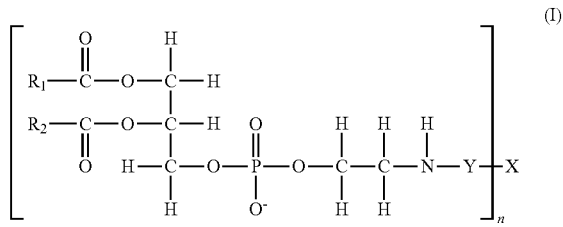

(I)

wherein
- $R_1$ is a linear, saturated, mono-unsaturated, or poly-unsaturated, alkyl chain ranging in length from 2 to 30 carbon atoms;
- $R_2$ is a linear, saturated, mono-unsaturated, or poly-unsaturated, alkyl chain ranging in length from 2 to 30 carbon atoms;
- Y is either nothing or a spacer group ranging in length from 2 to 30 atoms;
- X is a physiologically acceptable monomer, dimer, oligomer or polymer wherein X is a glycosaminoglycan (GAG); and
- n is a number from 1 to 70;
- wherein if Y is nothing the phosphatidylserine is directly linked to X via an amide bond and if Y is a spacer, said spacer is directly linked to X via an amide or an esteric bond and to said phosphatidylethanolamine via an amide bond.

In another embodiment, the molecular weight of said GAG is between 5 to 20 kD.

Examples of phosphatidylethanolamine (PE) moieties are analogues of the phospholipid in which the chain length of the two fatty acid groups attached to the glycerol backbone of the phospholipid varies from 2-30 carbon atoms length, and in which these fatty acids chains contain saturated and/or unsaturated carbon atoms. In lieu of fatty acid chains, alkyl chains attached directly or via an ether linkage to the glycerol backbone of the phospholipid are included as analogues of PE. In one embodiment, the PE moiety is dipalmitoyl-phosphatidyl-ethanolamine. In another embodiment, the PE moiety is dimyristoyl-phosphatidyl-ethanolamine.

Phosphatidyl-ethanolamine and its analogues may be from various sources, including natural, synthetic, and semi-synthetic derivatives and their isomers.

Phospholipids which can be employed in lieu of the PE moiety are N-methyl-PE derivatives and their analogues, linked through the amino group of the N-methyl-PE by a covalent bond; N,N-dimethyl-PE derivatives and their analogues linked through the amino group of the N,N-dimethyl-PE by a covalent bond, phosphatidylserine (PS) and its analogues, such as palmitoyl-stearoyl-PS, natural PS from various sources, semisynthetic PSs, synthetic, natural and artifactual PSs and their isomers. Other phospholipids useful as conjugated moieties in this invention are phosphatidylcholine (PC), phosphatidylinositol (PI), phosphatidic acid and phosphatidylglycerol (PG), as well as derivatives thereof comprising either phospholipids, lysophospholipids, phosphatidic acid, sphingomyelins, lysosphingomyelins, ceramide, and sphingosine.

For PE-conjugates and PS-conjugates, the phospholipid is linked to the conjugated monomer or polymer moiety through the nitrogen atom of the phospholipid polar head group, either directly or via a spacer group. For PC, PI, and PG conjugates, the phospholipid is linked to the conjugated monomer or polymer moiety through either the nitrogen or one of the oxygen atoms of the polar head group, either directly or via a spacer group.

In another embodiment, said lipid-polymer conjugate is represented by the structure of the general formula (II):

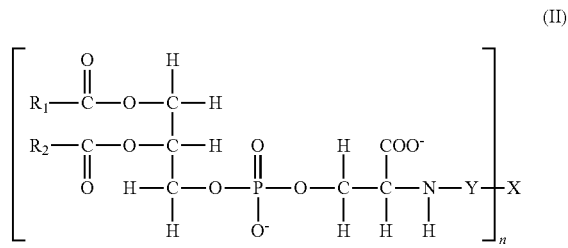

(II)

wherein
- $R_1$ is a linear, saturated, mono-unsaturated, or poly-unsaturated, alkyl chain ranging in length from 2 to 30 carbon atoms;
- $R_2$ is a linear, saturated, mono-unsaturated, or poly-unsaturated, alkyl chain ranging in length from 2 to 30 carbon atoms;
- Y is either nothing or a spacer group ranging in length from 2 to 30 atoms;
- X is a physiologically acceptable monomer, dimer, oligomer or polymer wherein X is a glycosaminoglycan; and
- n is a number from 1 to 70;
    - wherein if Y is nothing the phosphatidylserine is directly linked to X via an amide bond and if Y is a spacer, said spacer is directly linked to X via an amide or an esteric bond and to said phosphatidylethanolamine via an amide bond.

In one embodiment, the phosphatidylserine may be bonded to Y, or to X if Y is nothing, via the COO⁻ moiety of the phosphatidylserine.

In another embodiment, said lipid-polymer conjugate is represented by the structure of the general formula (III):

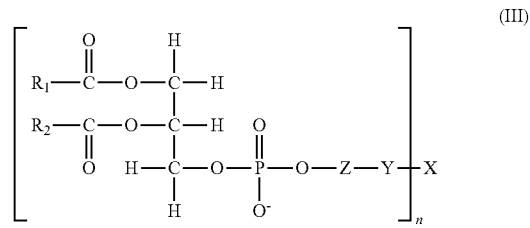

(III)

wherein
- $R_1$ is a linear, saturated, mono-unsaturated, or poly-unsaturated, alkyl chain ranging in length from 2 to 30 carbon atoms;
- $R_2$ is a linear, saturated, mono-unsaturated, or poly-unsaturated, alkyl chain ranging in length from 2 to 30 carbon atoms;
- Z is either nothing, inositol, choline, or glycerol;
- Y is either nothing or a spacer group ranging in length from 2 to 30 atoms;
- X is a physiologically acceptable monomer, dimer, oligomer or polymer wherein X is a glycosaminoglycan; and
- n is a number from 1 to 70;
- wherein any bond between the phosphatidyl, Z, Y and X is either an amide or an esteric bond.

In another embodiment, said lipid-polymer conjugate is represented by the structure of the general formula (IV).

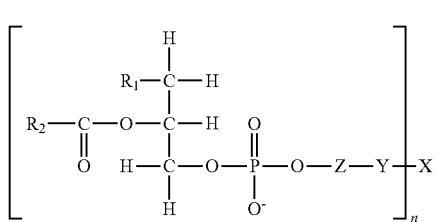

(IV)

wherein $R_1$ is a linear, saturated, mono-unsaturated, or poly-unsaturated, alkyl chain ranging in length from 2 to 30 carbon atoms;

$R_2$ is a linear, saturated, mono-unsaturated, or poly-unsaturated, alkyl chain ranging in length from 2 to 30 carbon atoms;

Z is either nothing, ethanolamine, serine, inositol, choline, or glycerol;

Y is either nothing or a spacer group ranging in length from 2 to 30 atoms;

X is a physiologically acceptable monomer, dimer, oligomer or polymer wherein X is a glycosaminoglycan; and n is a number from 1 to 70;

wherein any bond between the phospholipid, Z, Y and X is either an amide or an esteric bond.

In another embodiment, said lipid-polymer conjugate is represented by the structure of the general formula (V):

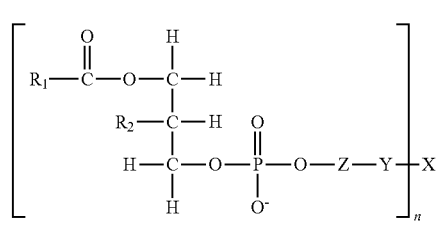

(V)

wherein $R_1$ is a linear, saturated, mono-unsaturated, or poly-unsaturated, alkyl chain ranging in length from 2 to 30 carbon atoms;

$R_2$ is a linear, saturated, mono-unsaturated, or poly-unsaturated, alkyl chain ranging in length from 2 to 30 carbon atoms;

Z is either nothing, ethanolamine, serine, inositol, choline, or glycerol;

Y is either nothing or a spacer group ranging in length from 2 to 30 atoms;

X is a physiologically acceptable monomer, dimer, oligomer or polymer wherein X is a glycosaminoglycan; and n is a number from 1 to 70;

wherein any bond between the phospholipid, Z, Y and X is either an amide or an esteric bond.

In another embodiment, said lipid-polymer conjugate is represented by the structure of the general formula (VI):

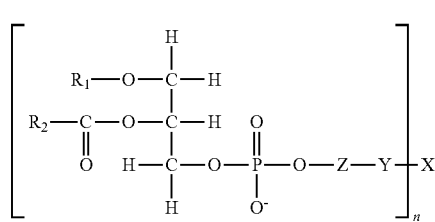

(VI)

wherein $R_1$ is a linear, saturated, mono-unsaturated, or poly-unsaturated, alkyl chain ranging in length from 2 to 30 carbon atoms;

$R_2$ is a linear, saturated, mono-unsaturated, or poly-unsaturated, alkyl chain ranging in length from 2 to 30 carbon atoms;

Z is either nothing, ethanolamine, serine, inositol, choline, or glycerol;

Y is either nothing or a spacer group ranging in length from 2 to 30 atoms;

X is a physiologically acceptable monomer, dimer, oligomer or polymer wherein X is a glycosaminoglycan; and n is a number from 1 to 70;

wherein any bond between the phospholipid, Z, Y and X is either an amide or an esteric bond.

In another embodiment, said lipid-polymer conjugate is represented by the structure of the general formula (VII):

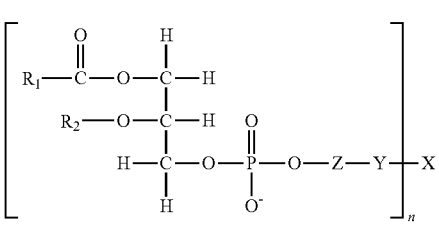

(VII)

wherein $R_1$ is a linear, saturated, mono-unsaturated, or poly-unsaturated, alkyl chain ranging in length from 2 to 30 carbon atoms;

$R_2$ is a linear, saturated, mono-unsaturated, or poly-unsaturated, alkyl chain ranging in length from 2 to 30 carbon atoms;

Z is either nothing, ethanolamine, serine, inositol, choline, or glycerol;

Y is either nothing or a spacer group ranging in length from 2 to 30 atoms;

X is a physiologically acceptable monomer, dimer, oligomer or polymer wherein X is a glycosaminoglycan; and n is a number from 1 to 70;

wherein any bond between the phospholipid, Z, Y and X is either an amide or an esteric bond.

In another embodiment, said lipid-polymer conjugate is represented by the structure of the general formula (VIII):

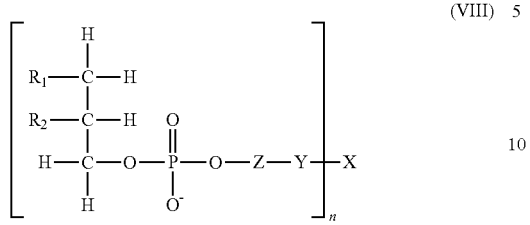

(VIII)

wherein
- $R_1$ is a linear, saturated, mono-unsaturated, or poly-unsaturated, alkyl chain ranging in length from 2 to 30 carbon atoms;
- $R_2$ is either hydrogen or a linear, saturated, mono-unsaturated, or poly-unsaturated, alkyl chain ranging in length from 2 to 30 carbon atoms;
- Z is either nothing, ethanolamine, serine, inositol, choline, or glycerol;
- Y is either nothing or a spacer group ranging in length from 2 to 30 atoms;
- X is a physiologically acceptable monomer, dimer, oligomer or polymer wherein X is a glycosaminoglycan; and
- n is a number from 1 to 70;
- wherein any bond between the phospholipid, Z, Y and X is either an amide or an esteric bond.

In another embodiment, said lipid-polymer conjugate is represented by the structure of the of the general formula (IX):

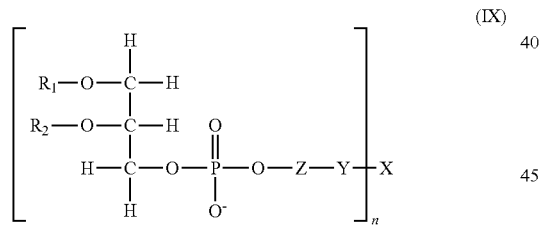

(IX)

wherein
- $R_1$ is either hydrogen or a linear, saturated, mono-unsaturated, or poly-unsaturated, alkyl chain ranging in length from 2 to 30 carbon atoms;
- $R_2$ is either hydrogen or a linear, saturated, mono-unsaturated, or poly-unsaturated, alkyl chain ranging in length from 2 to 30 carbon atoms;
- Z is either nothing, ethanolamine, serine, inositol, choline, or glycerol;
- Y is either nothing or a spacer group ranging in length from 2 to 30 atoms;
- X is a physiologically acceptable monomer, dimer, oligomer, or polymer wherein X is a glycosaminoglycan; and
- n is a number from 1 to 70;
- wherein any bond between the phospholipid, Z, Y and X is either an amide or an esteric bond.

In another embodiment, said lipid-polymer conjugate is represented by the structure of the general formula (IXa):

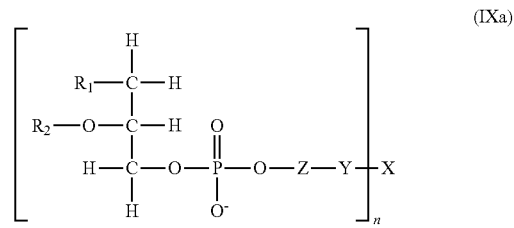

(IXa)

wherein
- $R_1$ is either hydrogen or a linear, saturated, mono-unsaturated, or poly-unsaturated, alkyl chain ranging in length from 2 to 30 carbon atoms;
- $R_2$ is either hydrogen or a linear, saturated, mono-unsaturated, or poly-unsaturated, alkyl chain ranging in length from 2 to 30 carbon atoms;
- Z is either nothing, ethanolamine, serine, inositol, choline, or glycerol;
- Y is either nothing or a spacer group ranging in length from 2 to 30 atoms;
- X is a physiologically acceptable monomer, dimer, oligomer, or polymer wherein X is a glycosaminoglycan; and
- n is a number from 1 to 70;
- wherein any bond between the phospholipid, Z, Y and X is either an amide or an esteric bond.

In another embodiment, said lipid-polymer conjugate is represented by the structure of the general formula (IXb):

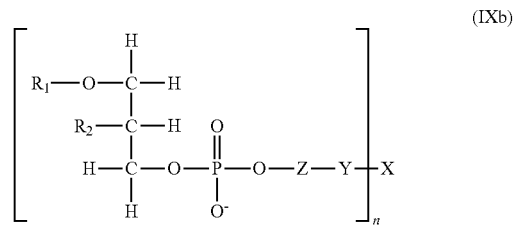

(IXb)

wherein
- $R_1$ is either hydrogen or a linear, saturated, mono-unsaturated, or poly-unsaturated, alkyl chain ranging in length from 2 to 30 carbon atoms;
- $R_2$ is either hydrogen or a linear, saturated, mono-unsaturated, or poly-unsaturated, alkyl chain ranging in length from 2 to 30 carbon atoms;
- Z is either nothing, ethanolamine, serine, inositol, choline, or glycerol;
- Y is either nothing or a spacer group ranging in length from 2 to 30 atoms;
- X is a physiologically acceptable monomer, dimer, oligomer, or polymer wherein X is a glycosaminoglycan; and
- n is a number from 1 to 70;
- wherein any bond between the phospholipid, Z, Y and X is either an amide or an esteric bond.

In another embodiment, said lipid-polymer conjugate is represented by the structure of the of the general formula (X):

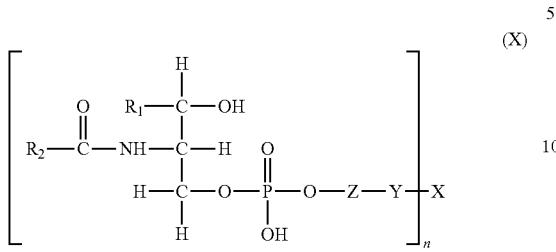

wherein $R_1$ is either hydrogen or a linear, saturated, mono-unsaturated, or poly-unsaturated, alkyl chain ranging in length from 2 to 30 carbon atoms;

$R_2$ is a linear, saturated, mono-unsaturated, or poly-unsaturated, alkyl chain ranging in length from 2 to 30 carbon atoms;

Z is either nothing, ethanolamine, serine, inositol, choline, or glycerol;

Y is either nothing or a spacer group ranging in length from 2 to 30 atoms;

X is a physiologically acceptable monomer, dimer, oligomer, or polymer wherein X is a glycosaminoglycan; and n is a number from 1 to 70;

wherein any bond between the ceramide phosphoryl, Z, Y and X is either an amide or an esteric bond.

In another embodiment, the compound for use in the present invention is represented by the structure of the general formula (Xa):

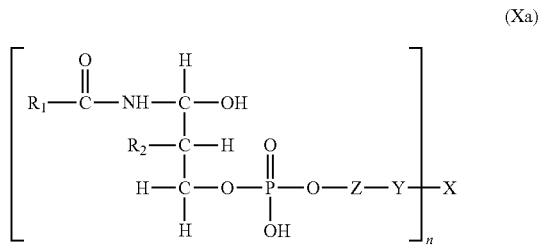

wherein $R_1$ is either hydrogen or a linear, saturated, mono-unsaturated, or poly-unsaturated, alkyl chain ranging in length from 2 to 30 carbon atoms;

$R_2$ is a linear, saturated, mono-unsaturated, or poly-unsaturated, alkyl chain ranging in length from 2 to 30 carbon atoms;

Z is either nothing, ethanolamine, serine, inositol, choline, or glycerol;

Y is either nothing or a spacer group ranging in length from 2 to 30 atoms;

X is a physiologically acceptable monomer, dimer, oligomer, or polymer wherein X is a glycosaminoglycan; and n is a number from 1 to 70;

wherein any bond between the ceramide phosphoryl, Z, Y and X is either an amide or an esteric bond.

In another embodiment, said lipid-polymer conjugate is represented by the structure of the of the general formula (XI):

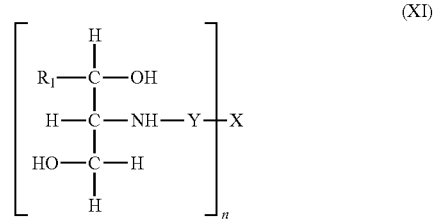

wherein $R_1$ is a linear, saturated, mono-unsaturated, or poly-unsaturated, alkyl chain ranging in length from 2 to 30 carbon atoms;

Y is either nothing or a spacer group ranging in length from 2 to 30 atoms;

X is a physiologically acceptable monomer, dimer, oligomer or polymer wherein X is a glycosaminoglycan; and n is a number from 1 to 70;

wherein if Y is nothing the sphingosyl is directly linked to X via an amide bond and if Y is a spacer, the spacer is directly linked to X and to the sphingosyl via an amide bond and to X via an amide or an esteric bond.

In another embodiment, said lipid-polymer conjugate is represented by the structure of the of the general formula (XII):

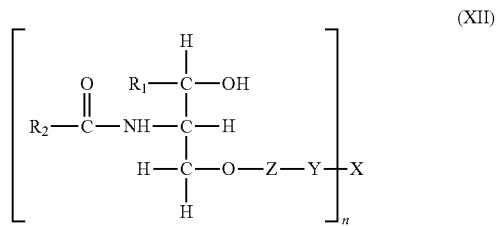

wherein $R_1$ is a linear, saturated, mono-unsaturated, or poly-unsaturated, alkyl chain ranging in length from 2 to 30 carbon atoms;

$R_2$ is a linear, saturated, mono-unsaturated, or poly-unsaturated, alkyl chain ranging in length from 2 to 30 carbon atoms;

Z is either nothing, ethanolamine, serine, inositol, choline, or glycerol;

Y is either nothing or a spacer group ranging in length from 2 to 30 atoms;

X is a physiologically acceptable monomer, dimer, oligomer or polymer wherein X is a glycosaminoglycan; and n is a number from 1 to 70;

wherein any bond between the ceramide, Z, Y and X is either an amide or an esteric bond.

In another embodiment, the compound for use in the present invention is represented by the structure of the general formula (XIIa):

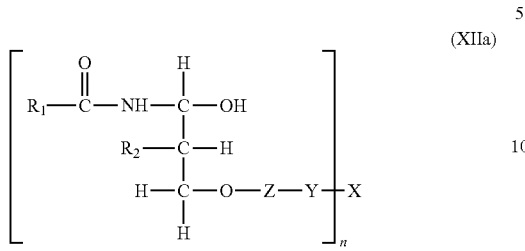

(XIIa)

wherein $R_1$ is a linear, saturated, mono-unsaturated, or poly-unsaturated, alkyl chain ranging in length from 2 to 30 carbon atoms;

$R_2$ is a linear, saturated, mono-unsaturated, or poly-unsaturated, alkyl chain ranging in length from 2 to 30 carbon atoms;

Z is either nothing, ethanolamine, serine, inositol, choline, or glycerol;

Y is either nothing or a spacer group ranging in length from 2 to 30 atoms;

X is a physiologically acceptable monomer, dimer, oligomer or polymer wherein X is a glycosaminoglycan; and n is a number from 1 to 70;

wherein any bond between the ceramide, Z, Y and X is either an amide or an esteric bond.

In another embodiment, said lipid-polymer conjugate is represented by the structure of the general formula (XIII):

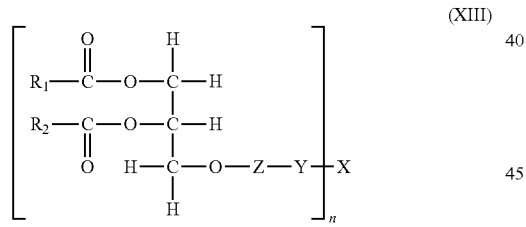

(XIII)

wherein $R_1$ is a linear, saturated, mono-unsaturated, or poly-unsaturated, alkyl chain ranging in length from 2 to 30 carbon atoms;

$R_2$ is a linear, saturated, mono-unsaturated, or poly-unsaturated, alkyl chain ranging in length from 2 to 30 carbon atoms;

Z is either nothing, ethanolamine, serine, choline, inositol, or glycerol;

Y is either nothing or a spacer group ranging in length from 2 to 30 atoms;

X is a physiologically acceptable monomer, dimer, oligomer or polymer wherein X is a glycosaminoglycan; and n is a number from 1 to 70;

wherein any bond between the diglyceryl, Z, Y and X is either an amide or an esteric bond.

In another embodiment, said lipid-polymer conjugate is represented by the structure of the general formula (XIV):

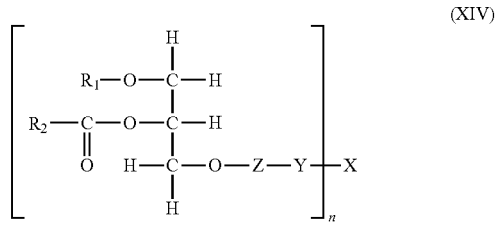

(XIV)

wherein $R_1$ is either hydrogen or a linear, saturated, mono-unsaturated, or poly-unsaturated, alkyl chain ranging in length from 2 to 30 carbon atoms;

$R_2$ is a linear, saturated, mono-unsaturated, or poly-unsaturated, alkyl chain ranging in length from 2 to 30 carbon atoms;

Z is either nothing, choline, ethanolamine, serine, inositol, or glycerol;

Y is either nothing or a spacer group ranging in length from 2 to 30 atoms;

X is a physiologically acceptable monomer, dimer, oligomer or polymer wherein X is a glycosaminoglycan; and n is a number from 1 to 70;

wherein any bond between the glycerolipid, Z, Y and X is either an amide or an esteric bond.

In another embodiment, said lipid-polymer conjugate is represented by the structure of the general formula (XV):

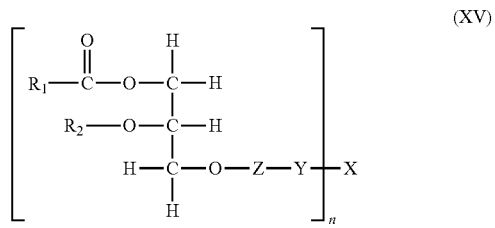

(XV)

wherein $R_1$ is a linear, saturated, mono-unsaturated, or poly-unsaturated, alkyl chain ranging in length from 2 to 30 carbon atoms;

$R_2$ is either hydrogen or a linear, saturated, mono-unsaturated, or poly-unsaturated, alkyl chain ranging in length from 2 to 30 carbon atoms;

Z is either nothing, choline, ethanolamine, serine, inositol, or glycerol;

Y is either nothing or a spacer group ranging in length from 2 to 30 atoms;

X is a physiologically acceptable monomer, dimer, oligomer or polymer wherein X is a glycosaminoglycan; and n is a number from 1 to 70;

wherein any bond between the glycerolipid, Z, Y and X is either an amide or an esteric bond.

In another embodiment, said lipid-polymer conjugate is represented by the structure of the general formula (XVI):

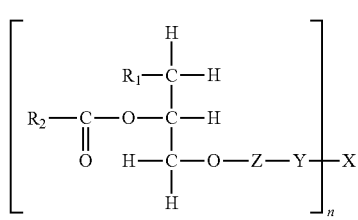

(XVI)

wherein $R_1$ is either hydrogen or a linear, saturated, mono-unsaturated, or poly-unsaturated, alkyl chain ranging in length from 2 to 30 carbon atoms;

$R_2$ is a linear, saturated, mono-unsaturated, or poly-unsaturated, alkyl chain ranging in length from 2 to 30 carbon atoms;

Z is either nothing, choline, ethanolamine, serine, inositol, or glycerol;

Y is either nothing or a spacer group ranging in length from 2 to 30 atoms;

X is a physiologically acceptable monomer, dimer, oligomer or polymer wherein X is a glycosaminoglycan; and n is a number from 1 to 70;

wherein any bond between the lipid, Z, Y and X is either an amide or an esteric bond.

In another embodiment, said lipid-polymer conjugate is represented by the structure of the general formula (XVII):

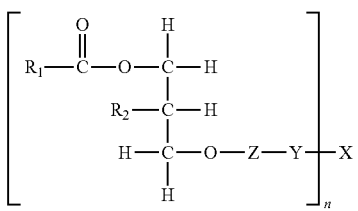

(XVII)

wherein $R_1$ is either hydrogen or a linear, saturated, mono-unsaturated, or poly-unsaturated, alkyl chain ranging in length from 2 to 30 carbon atoms;

$R_2$ is a linear, saturated, mono-unsaturated, or poly-unsaturated, alkyl chain ranging in length from 2 to 30 carbon atoms;

Z is either nothing, choline, ethanolamine, serine, inositol, or glycerol;

Y is either nothing or a spacer group ranging in length from 2 to 30 atoms;

X is a physiologically acceptable monomer, dimer, oligomer or polymer wherein X is a glycosaminoglycan; and n is a number from 1 to 70;

wherein any bond between the lipid, Z, Y and X is either an amide or an esteric bond.

In another embodiment, said lipid-polymer conjugate is represented by the structure of the general formula (XVIII):

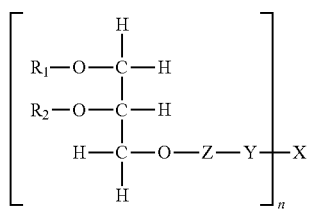

(XVIII)

wherein $R_1$ is either hydrogen or a linear, saturated, mono-unsaturated, or poly-unsaturated, alkyl chain ranging in length from 2 to 30 carbon atoms;

$R_2$ is either hydrogen or a linear, saturated, mono-unsaturated, or poly-unsaturated, alkyl chain ranging in length from 2 to 30 carbon atoms;

Z is either nothing, choline, ethanolamine, serine, inositol, or glycerol;

Y is either nothing or a spacer group ranging in length from 2 to 30 atoms;

X is a physiologically acceptable monomer, dimer, oligomer or polymer wherein X is a glycosaminoglycan; and n is a number from 1 to 70;

wherein any bond between the lipid, Z, Y and X is either an amide or an esteric bond.

In another embodiment, said lipid-polymer conjugate is represented by the structure of the general formula (XIX):

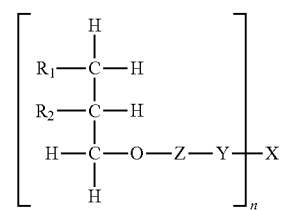

(XIX)

wherein $R_1$ is either hydrogen or a linear, saturated, mono-unsaturated, or poly-unsaturated, alkyl chain ranging in length from 2 to 30 carbon atoms;

$R_2$ is either hydrogen or a linear, saturated, mono-unsaturated, or poly-unsaturated, alkyl chain ranging in length from 2 to 30 carbon atoms;

Z is either nothing, choline, ethanolamine, serine, inositol, or glycerol;

Y is either nothing or a spacer group ranging in length from 2 to 30 atoms;

X is a physiologically acceptable monomer, dimer, oligomer or polymer wherein X is a glycosaminoglycan; and n is a number from 1 to 70;

wherein any bond between the lipid, Z, Y and X is either an amide or an esteric bond.

In another embodiment, said lipid-polymer conjugate is represented by the structure of the general formula (XX):

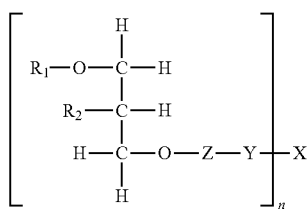

(XX)

wherein
$R_1$ is either hydrogen or a linear, saturated, mono-unsaturated, or poly-unsaturated, alkyl chain ranging in length from 2 to 30 carbon atoms;
$R_2$ is either hydrogen or a linear, saturated, mono-unsaturated, or poly-unsaturated, alkyl chain ranging in length from 2 to 30 carbon atoms;
Z is either nothing, choline, ethanolamine, serine, inositol, or glycerol;
Y is either nothing or a spacer group ranging in length from 2 to 30 atoms;
X is a physiologically acceptable monomer, dimer, oligomer or polymer wherein X is a glycosaminoglycan; and
n is a number from 1 to 70;
wherein any bond between the lipid, Z, Y and X is either an amide or an esteric bond.

In another embodiment, said lipid-polymer conjugate is represented by the structure of the general formula (XXI):

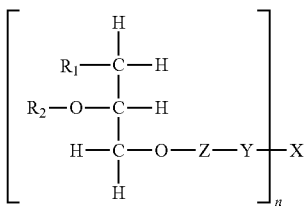

(XXI)

wherein
$R_1$ is either hydrogen or a linear, saturated, mono-unsaturated, or poly-unsaturated, alkyl chain ranging in length from 2 to 30 carbon atoms;
$R_2$ is either hydrogen or a linear, saturated, mono-unsaturated, or poly-unsaturated, alkyl chain ranging in length from 2 to 30 carbon atoms;
Z is either nothing, choline, ethanolamine, serine, inositol, or glycerol;
Y is either nothing or a spacer group ranging in length from 2 to 30 atoms;
X is a physiologically acceptable monomer, dimer, oligomer or polymer wherein X is a glycosaminoglycan; and
n is a number from 1 to 70;
wherein any bond between the lipid, Z, Y and X is either an amide or an esteric bond.

In another embodiment, $R_1$ of formulae (I), (II), (III), (IV), (V), (VI), (VII), (VIII), (IX), (IXa), (IXb), (X), (Xa), (XI), (XII), (XIIa), (XIII), (XIV), (XV), (XVI), (XVII), (XVIII), (XIX), (XX), (XXI) and (XXII) is a residue of palmitic acid or a residue of myristic acid.

In another embodiment, $R_2$ of formulae (I), (II), (III), (IV), (V), (VI), (VII), (VIII), (IX), (IXa), (IXb), (X), (Xa), (XI), (XII), (XIIa), (XIII), (XIV), (XV), (XVI), (XVII), (XVIII), (XIX), (XX), (XXI) and (XXII) is a residue of palmitic acid or a residue of myristic acid.

In some embodiments, the compounds (A), (B) (III), (IV), (V), (VI), (VII), (VIII), (IX), (IXa), (IXb), (X), (Xa), (XI), (XII), (XIIa), (XIII), (XIV), (XV), (XVI), (XVII), (XVIII), (XIX), (XX), (XXI) and (XXII) as presented hereinabove comprises a Z group. In one embodiment, Z is a nothing. In another embodiment Z is inositol. In another embodiment, Z is choline. In another embodiment, Z is glycerol. In another embodiment, Z is ethanoleamine. In another embodiment, Z is serine.

For any or all of the compounds represented by the structures of the general formulae (A), (I), (II), (III), (IV), (V), (VI), (VII), (VIII), (IX), (IXa), (IXb), (X), (Xa), (XI), (XII), (XIIa), (XIII), (XIV), (XV), (XVI), (XVII), (XVIII), (XIX), (XX), (XXI), and (XXII) hereinabove: In one embodiment, X is a glycosaminoglycan. According to this aspect and in one embodiment, the glycosaminoglycan may be, inter alia, hyaluronic acid, heparin, heparan sulfate, chondroitin sulfate, keratin, keratan sulfate, dermatan sulfate or a derivative thereof. In one embodiment, the chondroitin sulfate may be, inter alia, chondroitin-6-sulfate, chondroitin-4-sulfate or a derivative thereof. In another embodiment, X is not a glycosaminoglycan. In another embodiment, X is a polysaccharide, which in one embodiment is a heteropolysaccharide, and in another embodiment, is a homopolysaccharide. In another embodiment, X is a polypyranose.

In another embodiment, the glycosaminoglycan is a polymer of disaccharide units. In another embodiment, the number of the disaccharide units in the polymer is m. In another embodiment, m is a number from 2-10,000. In another embodiment, m is a number from 2-500. In another embodiment, m is a number from 2-1000. In another embodiment, m is a number from 50-500. In another embodiment, m is a number from 2-2000. In another embodiment, m is a number from 500-2000. In another embodiment, m is a number from 1000-2000. In another embodiment, m is a number from 2000-5000. In another embodiment, m is a number from 3000-7000. In another embodiment, m is a number from 5000-10,000. In another embodiment, a disaccharide unit of a glycosaminoglycan may be bound to one lipid or phospholipid moiety. In another embodiment, each disaccharide unit of the glycosaminoglycan may be bound to zero or one lipid or phospholipid moieties. In another embodiment, the lipid or phospholipid moieties are bound to the —COOH group of the disaccharide unit. In another embodiment, the bond between the lipid or phospholipid moiety and the disaccharide unit is an amide bond.

In one embodiment, this invention provides lipid-GAG conjugate or phospholipid-GAG conjugate, and methods of use thereof, wherein said conjugate represented by the structures of the general formulae (A), (I), (II), (III), (IV), (V), (VI), (VII), (VIII), (IX), (IXa), (IXb), (X), (Xa), (XI), (XII), (XIIa), (XIII), (XIV), (XV), (XVI), (XVII), (XVIII), (XIX), (XX), (XXI), and (XXII). In another embodiment, the average molecular weight of said GAG is between 5 kD to 90 kD. In another embodiment, the average molecular weight of said GAG is between 5 kD to 60 kD. In another embodiment, the average molecular weight of said GAG is between 5 kD to 40 kD. In another embodiment, the average molecular weight of said GAG is between 5 kD to 15 kD. In another embodiment, the average molecular weight of said GAG is between 5 kD to 20 kD. In another embodiment, the lipid-GAG conjugate is a phospholipid-GAG conjugate.

In one embodiment of the invention, Y is nothing. Non-limiting examples of suitable divalent groups forming the optional bridging group (which in one embodiment, is referred to as a spacer) Y, according to embodiments of the invention, are straight or branched chain alkylene, e.g., of 2 or more, preferably 4 to 30 carbon atoms, —CO-alkylene-CO, —NH-alkylene-NH—, —CO-alkylene-NH—, —NH-alkylene-NH, CO-alkylene-NH—, an amino acid, cycloalkylene, wherein alkylene in each instance, is straight or branched chain and contains 2 or more, preferably 2 to 30 atoms in the chain, —(—O—CH(CH$_3$)CH$_2$)$_x$— wherein x is an integer of 1 or more.

In one embodiment of the invention, the sugar rings of the glycosaminoglycan are intact. In another embodiment, intact refers to closed. In another embodiment, intact refers to natural. In another embodiment, intact refers to unbroken.

In one embodiment of the invention, the structure of the lipid or phospholipid in any compound according to the invention is intact. In another embodiment, the natural structure of the lipid or phospholipids in any compound according to the invention is maintained.

In one embodiment, the compounds for use in the present invention are biodegradable.

In some embodiments, the compounds for use are as listed in Table 1 below.

TABLE 1

| Phospholipid | Spacer | Polymer (m.w.) |
| --- | --- | --- |
| PE | None | Hyaluronic acid (2-2000 kDa) |
| Dimyristoyl-PE | None | Hyaluronic acid |
| PE | None | Heparin (0.5-110 kDa) |
| PE | None | Chondroitin sulfate A |
| PE | None | Carboxymethylcellulose (20-500 kDa) |
| PE | Dicarboxylic acid + Diamine | Polygeline (haemaccel) (4-40 kDa) |
| PE | None | Hydroxyethylstarch |
| PE | Dicarboxylic acid + Diamine | Dextran (1-2,000 kDa) |
| PE | Carboxyl amino group | Hyaluronic acid (5-20 kDa) |
| PE | Dicarboxyl group | Hyaluronic acid (5-20 kDa) |
| PE | Dipalmitoic acid | Hyaluronic acid (5-20 kDa) |
| PE | Carboxyl amino group | Heparin (5-20 kDa) |
| PE | Dicarboxyl group | Heparin (5-20 kDa) |
| PE | Carboxyl amino group | Chondroitin sulfate A |
| PE | Dicarboxyl group | Chondroitin sulfate A |
| PE | Carboxyl amino group | Carboxymethylcellulose (5-20 kDa) |
| PE | Dicarboxyl group | Carboxymethylcellulose (5-20 kDa) |
| PE | None | Polygeline (haemaccel) (5-20 kDa) |
| PE | Carboxyl amino group | Polygeline (haemaccel) (5-20 kDa) |
| PE | Dicarboxyl group | Polygeline (haemaccel) (5-20 kDa) |
| PE | Carboxyl amino group | Hydroxyethylstarch |
| PE | Dicarboxyl group | Hydroxyethylstarch |
| PE | None | Dextran (5-20 kDa) |
| PE | Carboxyl amino group | Dextran (5-20 kDa) |
| PE | Dicarboxyl group | Dextran (5-20 kDa) |

TABLE 1-continued

| Phospholipid | Spacer | Polymer (m.w.) |
| --- | --- | --- |
| PE | None | Chondroitin sulfates |
| Dipalmitoyl-PE | None | Hyaluronic acid |
| Dipalmitoyl-PE | None | Heparin |
| Dipalmitoyl-PE | None | Chondroitin sulfate A |
| Dipalmitoyl-PE | None | Carboxymethylcellulose |
| Dipalmitoyl-PE | None | Polygeline (haemaccel) |
| Dipalmitoyl-PE | None | Hydroxyethylstarch |
| Dipalmitoyl-PE | None | Dextran |
| Dimyristoyl-PE | None | Heparin |
| Dimyristoyl-PE | None | Chondroitin sulfate A |
| Dimyristoyl-PE | None | Carboxymethylcellulose |
| Dimyristoyl-PE | None | Polygeline (haemaccel) |
| Dimyristoyl-PE | None | Hydroxyethylstarch |
| Dimyristoyl-PE | None | Dextran |
| PS | None | Hyaluronic acid |
| PS | None | Heparin |
| PS | None | Polygeline (haemaccel) |
| PC | None | Hyaluronic acid |
| PC | None | Heparin |
| PC | None | Polygeline (haemaccel) |
| PI | None | Hyaluronic acid |
| PI | None | Heparin |
| PI | None | Polygeline (haemaccel) |
| PG | None | Hyaluronic acid |
| PG | None | Heparin |
| PG | None | Polygeline (haemaccel) |

In one embodiment, this invention provides a lipid-polymer conjugate represented by the structure of the general formula (B):

(B)

wherein

L is a lipid or a phospholipid;

Z is either nothing, ethanolamine, serine, inositol, choline, phosphate, or glycerol;

Y is either nothing or a spacer group ranging in length from 2 to 30 atoms;

X is a glycosaminoglycan; and n is a number from 1 to 10;

wherein any bond between L, Z, Y and X is either an amide or an esteric bond.

In one embodiment, this invention provides a lipid-polymer conjugate represented by the structure of the general formula (XXII):

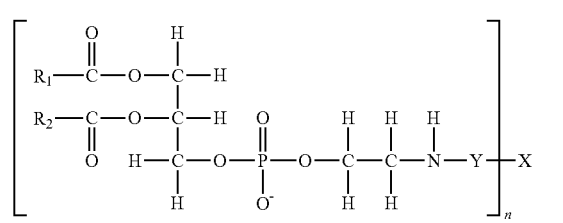

(XXII)

R$_1$ is a linear, saturated, mono-unsaturated, or poly-unsaturated, alkyl chain ranging in length from 2 to 30 carbon atoms;

R$_2$ is a linear, saturated, mono-unsaturated, or poly-unsaturated, alkyl chain ranging in length from 2 to 30 carbon atoms;

Y is either nothing or a spacer group ranging in length from 2 to 30 atoms;
X is a glycosaminoglycan; and
n is a number from 1 to 10;
wherein if Y is nothing the phosphatidylethanolamine is directly linked to X via an amide bond and if Y is a spacer, said spacer is directly linked to X via an amide or an esteric bond and to said phosphatidylethanolamine via an amide bond.

In one embodiment, n of formula (B) and formula (XXII) is 1-10, in another embodiment, n is 1. In another embodiment, n is 2. In another embodiment, n is 3. In another embodiment, n is 4. In another embodiment, n is 5. In another embodiment, n is 6. In another embodiment, n is 7. In another embodiment, n is 8. In another embodiment, n is 9. In another embodiment, n is 10.

In one embodiment, this invention provides a process for preparing a compound represented by the structure of the general formula (I):

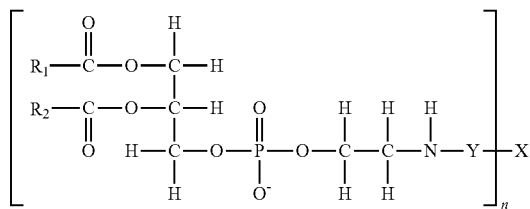

(I)

wherein
$R_1$ is a linear, saturated, mono-unsaturated, or poly-unsaturated, alkyl chain ranging in length from 2 to 30 carbon atoms;
$R_2$ is a linear, saturated, mono-unsaturated, or poly-unsaturated, alkyl chain ranging in length from 2 to 30 carbon atoms;
Y is either nothing or a spacer group ranging in length from 2 to 30 atoms;
X is a glycosaminoglycan; and
n is a number from 1 to 70;
wherein if Y is nothing the phosphatidylethanolamine is directly linked to X via an amide bond and if Y is a spacer, said spacer is directly linked to X via an amide or an esteric bond and to said phosphatidylethanolamine via an amide bond;
comprising reacting a phospholipid (PL) with a glycosaminoglycan (GAG) and a coupling agent, wherein the $mass_{PL}$ to $mass_{GAG}$ ratio from about 0.25:15 to about 5:15, respectively;

In one embodiment, this invention provides a process for preparing a compound represented by the structure of the general formula (I):

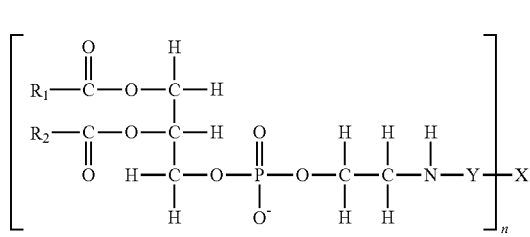

(I)

wherein
$R_1$ is a linear, saturated, mono-unsaturated, or poly-unsaturated, alkyl chain ranging in length from 2 to 30 carbon atoms;
$R_2$ is a linear, saturated, mono-unsaturated, or poly-unsaturated, alkyl chain ranging in length from 2 to 30 carbon atoms;
Y is either nothing or a spacer group ranging in length from 2 to 30 atoms;
X is a glycosaminoglycan; and
n is a number from 1 to 70;
wherein if Y is nothing the phosphatidylethanolamine is directly linked to X via an amide bond and if Y is a spacer, said spacer is directly linked to X via an amide or an esteric bond and to said phosphatidylethanolamine via an amide bond;
comprising the steps of:
a. reacting a phospholipid (PL) with a glycosaminoglycan (GAG) and a coupling agent, wherein the $mass_{PL}$ to $mass_{GAG}$ ratio from about 0.25:15 to about 5:15, respectively;
b. filtering the reaction mixture from (a) to generate a filtrate; and
c. extracting a product from a filtrate.

In another embodiment, said coupling agent is DCC, EDAC, BOP, PyBOP, HATU, TSTU or any other amide coupling agent. In another embodiment, said coupling agent is EDAC. In another embodiment, said coupling agent further comprises HOBT or HOAT.

In another embodiment, said filtering step comprises a 10 kD centrasette membrane.

In another embodiment, $R_1$ is the residue of palmitic acid or the residue of myristic acid.

In another embodiment, $R_2$ is the residue of palmitic acid or the residue of myristic acid.

In another embodiment, the average molecular weight of the glycosaminoglycan is between 5 kD to 90 kD. In another embodiment, the average molecular weight of the glycosaminoglycan is between 5 kD to 20 kD. In another embodiment, the average molecular weight of the glycosaminoglycan is between 5 kD to 10 kD. In another embodiment, the average molecular weight of the glycosaminoglycan is between 10 kD to 20 kD. In another embodiment, the average molecular weight of the glycosaminoglycan is between 20 kD to 50 kD. In another embodiment, the average molecular weight of the glycosaminoglycan is between 30 kD to 60 kD. In another embodiment, the average molecular weight of the glycosaminoglycan is between 40 kD to 70 kD. In another embodiment, the average molecular weight of the glycosaminoglycan is between 50 kD to 80 kD. In another embodiment, the average molecular weight of the glycosaminoglycan is between 60 kD to 90 kD In one embodiment, hyaluronic acid (HA) is used in solution form. In another embodiment, HA solution is prepared according to Example 1.

In one embodiment, the process for the preparation of fractionated hyaluronic acid includes ultrafiltration. In another embodiment, the ultrafiltration fractionation of hyaluronic acid is as described in Example 2.

In one embodiment, phosphatidylethanolamine-hyaluronic acid conjugate (HyPE) is prepared by reacting a GAG with a PL using a coupling agent. In another embodiment, HyPE is prepared according to Example 3 using the apparatus depicted in FIG. 1.

In one embodiment, fractionated HA is used in the preparation of HyPE. In another embodiment, fractionated HA is prepared according to Example 3. In another embodiment, HyPE is prepared according to Example 11.

In one embodiment, a coupling reagent is used in the preparation of HyPE according to Example 3. In another embodiment, EDAC is used as the coupling reagent. In another embodiment, DCC is used as the coupling agent. In another embodiment, BOP is used as the coupling agent. In another embodiment, PyBOP is used as the coupling agent. In another embodiment, HATU is used as the coupling agent. In another embodiment, TSTU is used as the coupling agent.

In one embodiment, the coupling agent used in the preparation of HyPE according to Example 3 comprises HOBT. In another embodiment, the coupling agent comprises HOAT.

In one embodiment, crude HyPE is processed by an ultrafiltration step. In another embodiment, HyPE is subjected to the alkaline ultrafiltration described in Example 4.

In one embodiment, filtered HyPE is isolated by extraction. In another embodiment, HyPE is extracted according to the process described in Example 5. In another embodiment, said extraction comprises dichloromethane, ethanol and methanol.

In one embodiment, this invention provides a method of treating an inflammatory disorder in a subject, said method comprising administering to a subject suffering from an inflammatory disorder a composition comprising a lipid-polymer conjugate comprising a glycosaminoglycan (GAG) conjugated to a phospholipid (PL) wherein said conjugate is prepared by reacting said GAG with said PL in a $mass_{PL}$ to $mass_{GAG}$ ratio from about 0.25:15 to about 5:15, respectively.

In another embodiment, said $mass_{PL}$ to $mass_{GAG}$ ratio is about 0.25:15. In another embodiment, said $mass_{PL}$ to $mass_{GAG}$ ratio is about 0.5:15. In another embodiment, said $mass_{PL}$ to $mass_{GAG}$ ratio is about 1:15. In another embodiment, said $mass_{PL}$ to $mass_{GAG}$ ratio is about 2:15. In another embodiment, said $mass_{PL}$ to $mass_{GAG}$ ratio is about 5:15.

In another embodiment, said inflammatory disorder is rheumatoid arthritis, osteoarthritis, wound healing, dermatitis, restenosis, cystic fibrosis, multiple sclerosis or sepsis.

In one embodiment, in vitro assays are used to measure the ability of HyPE and HyPE analogs to reduce the expression of pro-inflammatory cytokines. In another embodiment, cell-based assays are used according to Example 6, Example 7 and Example 8. In another embodiment, expression of IL-6 is measured. In another embodiment, expression of TNF-α is measured. In another embodiment, expression of IP-10 is measured. In another embodiment, expression of $PGE_2$ is measured.

In another embodiment, said composition is administered intravenously. In another embodiment, said composition is administered topically.

In one embodiment, the present invention provides a method for decreasing expression of proinflammatory chemokines, cytokines, or a combination thereof comprising the step of administering a compound represented by the structure of the general formula (A):

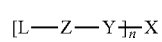
(A)

wherein
L is a lipid or a phospholipid;
Z is either nothing, ethanolamine, serine, inositol, choline, or glycerol;
Y is either nothing or a spacer group ranging in length from 2 to 30 atoms;
X is a glycosaminoglycan; and
n is a number from 1 to 70;
wherein any bond between L, Z, Y and X is either an amide or an esteric bond to a subject with high levels of proinflammatory chemokines, cytokines, or a combination thereof.

In one embodiment, the present invention provides a method of activating NF-κB, IL-6, IL-8, or a combination thereof in human airway epithelial cell lines comprising the step of administering to a subject a compound represented by the structure of the general formula (A):

(A)

wherein
L is a lipid or a phospholipid;
Z is either nothing, ethanolamine, serine, inositol, choline, or glycerol;
Y is either nothing or a spacer group ranging in length from 2 to 30 atoms;
X is a glycosaminoglycan; and
n is a number from 1 to 70;
wherein any bond between L, Z, Y and X is either an amide or an esteric bond.

Dosages and Routes of Administration

The methods of this invention can be adapted to the use of the therapeutic compositions comprising Lipid-conjugates in admixture with conventional excipients, i.e. pharmaceutically acceptable organic or inorganic carrier substances suitable for parenteral, enteral (e.g., oral) or topical application which do not deleteriously react with the active compounds. Suitable pharmaceutically acceptable carriers include but are not limited to water, salt solutions, alcohols, gum arabic, vegetable oils, benzyl alcohols, polyethylene glycols, gelatine, carbohydrates such as lactose, amylose or starch, magnesium stearate, talc, silicic acid, viscous paraffin, white paraffin, glycerol, alginates, hyaluronic acid, collagen, perfume oil, fatty acid monoglycerides and diglycerides, pentaerythritol fatty acid esters, hydroxy methylcellulose, polyvinyl pyrrolidone, etc. The pharmaceutical preparations can be sterilized and if desired mixed with auxiliary agents, e.g., lubricants, preservatives, stabilizers, wetting agents, emulsifiers, salts for influencing osmotic pressure, buffers, coloring, flavoring and/or aromatic substances and the like which do not deleteriously react with the active compounds. They can also be combined where desired with other active agents, e.g., vitamins, bronchodilators, steroids, anti-inflammatory compounds, gene therapy, i.e. sequences which code for the wild-type cystic fibrosis transmembrane conductance regulator (CFTR) receptor, surfactant proteins, etc., as will be understood by one skilled in the art.

In one embodiment, the invention provides for the administration of a salt of a compound as described herein as well. In one embodiment, the salt is a pharmaceutically acceptable salt, which, in turn may refer to non-toxic salts of compounds (which are generally prepared by reacting the free acid with a suitable organic or inorganic base) and include, but are not limited to, the acetate, benzenesulfonate, benzoate, bicarbonate, bisulfate, bitartrate, borate, bromide, calcium, camsylate, carbonate, chloride, clavulanate, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynapthoate, iodide, isothionate, lactate, lactobionate, laurate, malate, maleate, mandlate, mesylate, methylbromide, methylnitrate, methylsulfate, mucate, napsylate, nitrate, oleate, oxalate, pamaote, palmitate, panthothenate, phosphate, diphospate, polygalacturonate, salicylate, stearate, subacetate, succinate, tannate, tartrate, teoclate, tosylate, triethiodide, and valerate salts, as well as mixtures of these salts.

In one embodiment, the route of administration may be parenteral, enteral, or a combination thereof. In another embodiment, the route may be intra-ocular, conjunctival, topical, transdermal, intradermal, subcutaneous, intraperitoneal, intravenous, intra-arterial, vaginal, rectal, intratumoral, parcanceral, transmucosal, intramuscular, intravascular, intraventricular, intracranial, inhalation, nasal aspiration (spray), sublingual, oral, aerosol or suppository or a combination thereof. In one embodiment, the dosage regimen will be determined by skilled clinicians, based on factors such as exact nature of the condition being treated, the severity of the condition, the age and general physical condition of the patient, etc.

In general, the doses utilized for the above described purposes will vary, but will be in an effective amount to exert the desired anti-disease effect. As used herein, the term "pharmaceutically effective amount" refers to an amount of a compound of formula (I) which will produce the desired alleviation in symptoms or signs of disease in a patient. The doses utilized for any of the above-described purposes will generally be from 1 to about 1000 milligrams per kilogram of body weight (mg/kg), administered one to four times per day, or by continuous IV infusion. When the compositions are dosed topically, they will generally be in a concentration range of from 0.1 to about 10% w/v, administered 1-4 times per day.

In one embodiment, the use of a single chemical entity with potent anti-oxidant, membrane-stabilizing, anti-proliferative, anti-chemokine, anti-migratory, and anti-inflammatory activity provides the desired protection for a subject with an inflammatory disorder, or in another embodiment, the methods of this invention provide for use of a combination of the compounds described. In another embodiment, the compounds for use in the present invention may be provided in a single formulation/composition, or in another embodiment, multiple formulations may be used. In one embodiment, the formulations for use in the present invention may be administered simultaneously, or in another embodiment, at different time intervals, which may vary between minutes, hours, days, weeks or months.

In one embodiment the compositions comprising the compounds for use in the present invention may be administered via different routes, which in one embodiment, may be tailored to provide different compounds at different sites, for example some compounds may be given parenterally to provide for superior perfusion throughout the lung and lymphatic system, and in another embodiment, some formulations/compounds/compositions may be provided via aerosol, or in another embodiment, intranasally, to provide for higher lung mucosal concentration.is there something wrong with this sentence? Seems like you need the word "higher" before mucosal?

In one embodiment, the compounds for use in the invention may be used for acute treatment of temporary conditions, or may be administered chronically, as needed. In one embodiment of the invention, the concentrations of the compounds will depend on various factors, including the nature of the condition to be treated, the condition of the patient, the route of administration and the individual tolerability of the compositions.

In one embodiment, the methods of this invention provide for the administration of the compounds in early life of the subject, or in another embodiment, throughout the life of the subject, or in another embodiment, episodically, in response to severity or constancy of symptomatic stages, or in another embodiment. In another embodiment, the patients to whom the lipid or PL conjugates should be administered are those that are experiencing symptoms of disease or who are at risk of contracting the disease or experiencing a recurrent episode or exacerbation of the disease, or pathological conditions associated with the same.

As used herein, the term "pharmaceutically acceptable carrier" refers to any formulation which is safe, and provides the appropriate delivery for the desired route of administration of an effective amount of at least one compound of the present invention. As such, all of the above-described formulations of the present invention are hereby referred to as "pharmaceutically acceptable carriers." This term refers to as well the use of buffered formulations wherein the pH is maintained at a particular desired value, ranging from pH 4.0 to pH 9.0, in accordance with the stability of the compounds and route of administration.

For parenteral administration, particularly suitable are sterile solutions, preferably oily or aqueous solutions, as well as suspensions or emulsions. It is also possible to freeze-dry the new compounds and use the lyophilates obtained, for example, for the preparation of products for injection.

In one embodiment, implants or suppositories, can be used to administer a lipid-GAG conjugate of this invention.

For application by inhalation, particularly for treatment of airway obstruction or congestion, solutions or suspensions of the compounds mixed and aerosolized or nebulized in the presence of the appropriate carrier For topical application, particularly for the treatment of skin diseases such as contact dermatitis or psoriasis, admixture of the compounds with conventional creams or delayed release patches is acceptable.

For enteral application, particularly suitable are tablets, dragees, liquids, drops, suppositories, or capsules. A syrup, elixir, or the like can be used when a sweetened vehicle is employed. When indicated, suppositories or enema formulations may be the recommended route of administration.

Sustained or directed release compositions can be formulated, e.g., liposomes or those wherein the active compound is protected with differentially degradable coatings, e.g., by microencapsulation, multiple coatings, etc.

It will be appreciated that the actual preferred amounts of active compound in a specific case will vary according to the specific compound being utilized, the particular compositions formulated, the mode of application, and the particular situs and organism being treated. Dosages for a given host can be determined using conventional considerations, e.g., by customary comparison of the differential activities of the subject compounds and of a known agent, e.g., by means of an appropriate, conventional pharmacological protocol.

Methods of Use

In one embodiment of the invention, the methods of the present invention make use of a conjugate as described herein to treat a subject suffering from an inflammatory disorder, reduce or delay the mortality of a subject suffering from an inflammatory disorder or ameliorate symptoms associated with an inflammatory disorder.

In one embodiment, the compound for use in the present invention comprises dipalmitoyl phosphatidylethanolamine and heparin. In one embodiment, the compound for use in the present invention comprises dipalmitoyl phosphatidylethanolamine and chondroitin sulfate. In one embodiment, the compound for use in the present invention comprises dipalmitoyl phosphatidylethanolamine and hyaluronic acid. In one embodiment, the compound for use in the present invention comprises dipalmitoyl phosphatidylethanolamine and carboxymethylcellulose. In one embodiment, the compound for use in the present invention comprises dimyristoyl phosphatidylethanolamine and hyaluronic acid.

In one embodiment, the compound for use in the present invention is a dipalmitoyl phosphatidylethanolamine conjugated via an amide or ester bond to a glycosaminoglycan. In one embodiment, the compound for use in the present invention is a dipalmitoyl phosphatidylethanolamine conjugated via an amide or ester bond to a chondroitin sulfate, which is chondroitin-6-sulfate, chondroitin-4-sulfate or a derivative thereof. In another embodiment, the compound for use in the present invention is a dipalmitoyl phosphatidylethanolamine conjugated via an amide or ester bond to a heparin. In another embodiment, the compound for use in the present invention is a dipalmitoyl phosphatidylethanolamine conjugated via an amide or ester bond to a hyaluronic acid. In another embodiment, the compound for use in the present invention is a dimyristoyl phosphatidylethanolamine conjugated via an amide or ester bond to a hyaluronic acid.

In one embodiment, the conjugates of this invention display a wide-range combination of cytoprotective pharmacological activities, which are useful in the present invention. In one embodiment, the compounds may be useful for their anti-inflammatory effects. Cellular elaboration of cytokines and chemokines serve an important regulatory function in health; however, when a hyperactive response to stress or disease is triggered, these compounds may present in excess and damage tissue, thereby pushing the disease state toward further deterioration. In one embodiment, the lipid compounds for use in the methods of this invention, possess a combination of multiple and potent pharmacological effects, including inter-alia the ability to inhibit the extracellular form of the enzyme phospholipase A2.

Method of Treating CF

In one embodiment, the conjugates of this invention are useful in affecting inflammation in a subject with an inflammatory disorder, where the subject is administered lipid-conjugates at pre-symptomatic stages of the disease. A characteristic feature of inflammation in the CF lung is the persistent infiltration of massive numbers of neutrophils into the airways. Although neutrophils help to control infection, when present in great excess, they can be harmful. Major advances in the understanding of the inflammatory process in the CF lung have come from the use of bronchoscopy and bronchoalveolar lavage (BAL) to analyze the inflammatory process in patients who are relatively symptom free and/or do not regularly produce sputum. Recent BAL studies suggest that neutrophil-rich inflammation begins very early, even in infants without clinically apparent lung disease. Thus, in one embodiment, the lipid/phospholipid conjugates of the present invention may be useful in treating CF, even in presymptomatic stages of disease.

Thus, in one embodiment, the invention provides methods for treating a subject suffering from cystic fibrosis, reducing or delaying the mortality of a subject suffering from cystic fibrosis or ameliorating symptoms associated with cystic fibrosis, and the compounds/compositions/formulations, in one embodiment, diminish or abrogate a deleterious inflammatory response in said subject, or in another embodiment, prevent, treat, reduce the incidence of, reduce the severity of, delay the onset of, or diminish the pathogenesis of an infection is the CF subject. In another embodiment, the invention provides methods for decreasing expression of proinflammatory chemokines, cytokines, or a combination thereof, while in another embodiment, the invention provides methods of activating NF-κB, IL-6, IL-8, or a combination thereof in human airway epithelial cell lines.

Method of Treating Wounds

In another embodiment, provided herein a method for promoting wound healing comprising applying or administering to a wound site to be treated in a subject an effective amount of a composition comprising any conjugate as described herein. In another embodiment, provided herein a method for promoting wound healing comprising applying or administering to a wound site to be treated in a subject an effective amount of a composition comprising any compound represented by the structure of the general formula (A).

In another embodiment, promoting wound healing comprises inducing wound healing. In another embodiment, promoting wound healing comprises speeding up wound healing. In another embodiment, promoting wound healing comprises reducing the risk of viral and/or bacterial infection. In another embodiment, promoting wound healing comprises reducing inflammation in or near the wound site.

In another embodiment, the conjugates as described herein increase the rate of chronic and acute wound healing. In another embodiment, the conjugates as described herein counteract mechanisms which delay or impair wound healing. In another embodiment, the compounds as described herein counteract exogenous factors which delay or impair wound healing. In another embodiment, the conjugates as described herein counteract endogenous factors which delay or impair wound healing. In another embodiment, factors include: infection, ulceration particularly through diabetes, circulation problems associated with vascular disease, malnutrition, stress, cancer radiotherapy and/or chemotherapy, compromise of the immune system or simply due to the normal aging process. In another embodiment, a method a described herein provides both a therapeutic and a cosmetic approach that promote wound healing processes.

In another embodiment, wounds include, but are not limited to the following: surgical wounds; bites; burns; acid and alkali burns; cold burn (frostbite), sun burn, minor cuts, major cuts, abrasions, lacerations, wounds caused by gunshot or knife injury; wounds caused by congenital disorders; wounds following dental surgery; periodontal disease; wounds following trauma; tumour associated wounds, which can be classified as malignant cutaneous ulcers related to the primary tumour or metastases; ulcers, leg ulcers; foot ulcers; pressure sores and corneal wounds.

Method of Treating Arthritis

In another embodiment of the invention, the methods of the present invention make use of a conjugate as described herein for treating a subject suffering from arthritis, reducing or delaying the damage to the joints of a subject suffering from arthritis, or ameliorating symptoms associated with arthritis. In another embodiment of the invention, the methods of the present invention make use of a formulation comprising a conjugate as described herein for treating a subject suffering from arthritis, reducing or delaying the damage to the joints of a subject suffering from arthritis, or ameliorating symptoms associated with arthritis.

In another embodiment, provided herein a method of treating a subject suffering from joint pain, swelling within the joint, inflammation within the joint, or a combination thereof comprising the step of administering a composition comprising a conjugate of the invention to the subject. In another embodiment, provided herein a method of treating a subject suffering from joint pain, swelling within the joint, inflammation within the joint, or a combination thereof comprising the step of injecting into a swelled/inflamed joint a composition comprising a conjugate of the invention.

It is understood that one skilled in the art recognizes that the term "arthritis" refers to both rheumatoid arthritis (RA) and osteoarthritis (OA).

In another embodiment, a compound as described herein inhibits the production of IL-6, IL-8, TNF-alpha, NF-κB, or their combination, thereby reducing or delaying the damage to the joints of a subject suffering from arthritis. In another embodiment, a compound as described herein inhibits the production of IL-6, IL-8, TNF-alpha, NF-κB, or their combination, thereby ameliorating symptoms associated with arthritis. In another embodiment, methods comprising the administration of a conjugate as described herein treat a subject suffering from joint pain, swelling within the joint, inflammation within the joint, or a combination thereof by inhibiting the production of IL-6, IL-8, TNF-alpha, NF-κB, or their combination. In another embodiment, locally administering a composition comprising a conjugate as described herein by intra-joint injection inhibits the production of IL-6, IL-8, TNF-alpha, NF-κB, or their combination within the joint's cells. In another embodiment, locally administering a composition comprising a conjugate as described herein by intra-joint injection inhibits inflammation within the joint.

Method of Treating Other Inflammatory Disorders

It is understood by one skilled in the art that inflammatory disorders include, but are not limited to, disorders resulting from activation of the immune system. Thus, autoimmune disorders are understood to be inflammatory disorders. Such disorders include, but are not limited to, rheumatoid arthritis, osteoarthritis, wound healing, dermatitis, restenosis, cystic fibrosis, central nervous system tissue insult, multiple sclerosis, obstructive respiratory disease, Crohn's disease, cardiovascular disease, atherosclerosis, contact dermatitis, psoriasis, ARDS, or sepsis In one embodiment, the invention provides a method of treating a subject suffering from obstructive respiratory disease, including, inter alia, the step of administering to a subject an effective amount of a conjugate of this invention, thereby treating the subject suffering from obstructive respiratory disease.

In one embodiment, the invention provides a method of treating a subject suffering from colitis, Crohn's disease, or another form of intestinal mucosal injury, including, inter alia, the step of administering to a subject an effective amount of a conjugate of this invention, thereby treating the subject suffering from intestinal mucosal injury, including colitis or Crohn's disease.

In one embodiment, the invention provides a method of treating a subject suffering from cardiovascular disease, including, inter alia, the step of administering to a subject an effective amount of a conjugate of this invention, thereby treating the subject suffering from a cardiovascular disease.

The present invention provides a method of treating a subject suffering from atherosclerosis, including, inter alia, the step of administering to a conjugate of this invention, thereby treating the subject suffering from atherosclerosis.

In one embodiment, the invention provides a method of treating a subject suffering from central nervous system tissue insult, including, inter alia, the step of administering to a subject an effective amount of a conjugate of this invention, thereby treating the subject suffering from a central nervous system insult.

In one embodiment, the invention provides a method of treating a subject suffering from multiple sclerosis, including, inter alia, the step of administering to a subject an effective amount of conjugate of this invention, thereby treating the subject suffering from multiple sclerosis.

In one embodiment, the invention provides a method of treating a subject suffering from contact dermatitis, including, inter alia, the step of administering to a subject an effective amount of a conjugate of this invention, thereby treating the subject suffering from contact dermatitis.

In one embodiment, the invention provides a of treating a subject suffering from psoriasis, including, inter alia, the step of administering to a subject an effective amount of a conjugate of this invention, thereby treating the subject suffering from psoriasis.

In one embodiment, the invention provides a method of treating a subject suffering from sepsis, including, inter alia, the step of administering to a subject an effective amount of a conjugate of this invention, thereby treating the subject suffering from sepsis.

In one embodiment, the invention provides a method of treating a subject suffering from ARDS, comprising the steps of administering to a subject an effective amount of a conjugate of this invention, thereby treating the subject suffering from ARDS.

While pharmacological activity of the Lipid-conjugates described herein may be due in part to the nature of the lipid moiety, the multiple and diverse combination of pharmacological properties observed for the Lipid-conjugates may represent, in other embodiments, the ability of the conjugate to act essentially as several different drugs in one chemical entity. Thus, for example, lung mucosal or lung parenchymal injury, as may occur in CF, may be attenuated by any one or all of the pharmaceutical activities of immune suppression, anti-inflammation, anti-oxidation, suppression of nitric oxide production, or membrane stabilization.

In one embodiment, the invention provides a method of "treating" inflammatory disorders or related diseases or disorders, which in one embodiment, refers to both therapeutic treatment and prophylactic or preventative measures, wherein the object is to prevent or lessen the targeted pathologic condition or disorder as described hereinabove.

In one embodiment, treating refers to delaying the onset of symptoms, reducing the severity of symptoms, reducing the severity of an acute episode, reducing the number of symptoms, reducing the incidence of disease-related symptoms, reducing the latency of symptoms, ameliorating symptoms, reducing secondary symptoms, reducing secondary infections, prolonging patient survival, preventing relapse to a disease, decrease the number or frequency of relapse episodes, increasing latency between symptomatic episodes, increasing time to sustained progression, expediting remission, inducing remission, augmenting remission, speeding recovery, or increasing efficacy of or decreasing resistance to alternate therapeutics.

In one embodiment, the methods are useful in treating an infection in a subject, wherein the pathogen is a virus or in another embodiment, the pathogen is a bacterium. In one embodiment, the infection is with a pathogen which infects the respiratory system, such as mycobacteria, *pseudomonas, cryptococcus, streptococcus,* reovirus, influenza, or other infections known to those of skill in the art.

Without further elaboration, it is believed that one skilled in the art can, using the preceding description, utilize the present invention to its fullest extent. The following examples and preferred specific embodiments are, therefore, to be construed as merely illustrative, and not limitative of the remainder of the disclosure in any way whatsoever.

EXAMPLE 1

Preparation of Hyaluronic Acid (HA) Solution 4 g of chlorocresol was dissolved in 4 L of deionized (DI) water (0.1% solution). HA UL 15 was dissolved in 4 L of 0.1% chlorocresol solution with mechanical stiffing. To prevent clogging of the ultrafiltration membranes, the HA solution was filtered through a 100 μm filter followed by a 50 μm filter followed by a 10 μm filter, all previously disinfected with 10% hydrogen peroxide and washed with copious amounts of DI water to ensure hydrogen peroxide has been removed (verified with peroxide-detecting strips).

EXAMPLE 2

Ultrafiltration Fractionation of Hyaluronic Acid (HA)

HA solution of Example 1 was loaded into the Centramate system, previously disinfected with 10% hydrogen peroxide and washed with copious amounts of DI water to ensure hydrogen peroxide has been removed (verified with peroxide-detecting strips).

By means of constant volume diafiltration with 70 kDa Omega TFF membranes, 20 L of 0.1% chlorocresol solution, prepared as described in Example 1, was ultrafiltered, collecting the filtrate, the fraction less than 70 kDa, in a carboy, previously disinfected with 10% hydrogen peroxide. The pump speed and valves shall be set such that the retentate flow is ten times the filtrate flow and the feed pressure is less than 40 PSI.

The 70 kDa membranes were replaced with 30 kDa membranes and the Centramate system was disinfected with 10% hydrogen peroxide.

5 L of the filtrate, the fraction less than 70 kDa, were loaded into the reservoir and by means of constant volume diafiltration, the remaining 35 L in the carboys of the fraction less than 70 kDa were ultrafiltered. The reservoir volume was reduced to 2 L and an additional 10 L of DI water was ultrafiltered to remove the chlorocresol (confirmed by appropriate GC assay). The reservoir volume was further reduced to 1 L, reducing the pump speed, if necessary, to keep the feed pressure below 40 PSI. The reservoir was then emptied directly into an autoclaved lyoguard container, closed, frozen and lyophilized to yield HA UF 70/30. GPC analysis was performed to ensure that this lot of HA UF 70/30 was consistent with earlier batches. A bioburden assay and an appropriate GC assay for chlorocresol was performed. Karl Fischer analysis was performed to determine the water content of HA UF 70/30.

EXAMPLE 3

HyPE Synthesis Reaction

Figure 36:
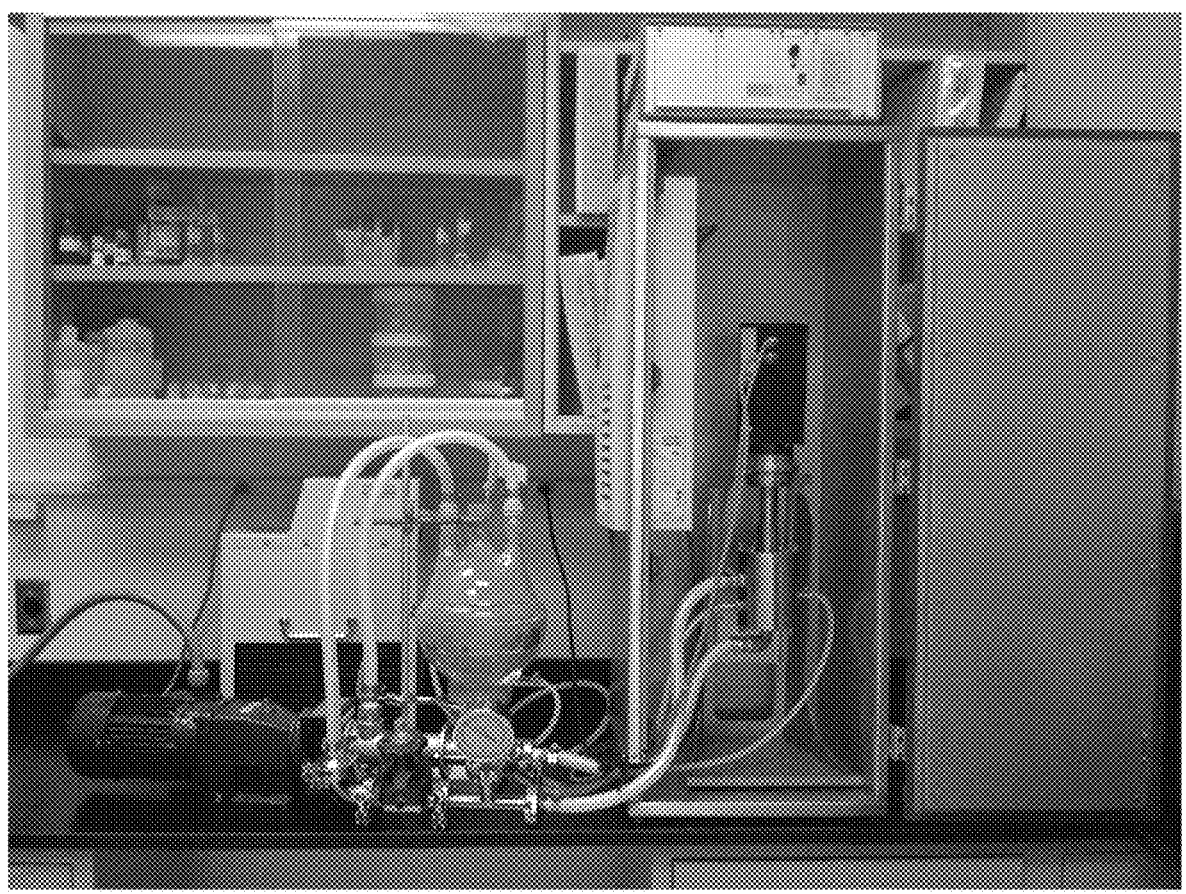
FIG. 36 depicts a photograph of the actual reaction vessel used for the preparation of HyPE. The chiller is behind the reaction vessel and the door on the sound-proof container is open to reveal the ultrasound flow-cell.

Using the apparatus depicted in FIG. 36, 24 g of 2-(N-morpholino)ethanesulfonic acid (MES) were dissolved in 125 mL of DI water and the pH was adjusted to pH 6.4 by addition of 4 N NaOH.

2.5 g of dipalmitoylphosphatidylethanolamine (DPPE) and 25 g of hydroxybenzotriazole (HOBT) were dissolved in 940 mL of tert-butanol and 80 mL of water with stiffing and heating at 45° C. in a 12 L round bottom flask (forming a closed system with the pump and the sonicator, all of which will have been previously autoclaved and/or disinfected with 70% isopropanol). To this was added 850 mL of water and 115 mL of the MES solution. The pH of this solution was adjusted to pH 6.4 by addition of 2.5 N NaOH. 25 g of HA UF 70/30 of Example 2 were then dissolved with stiffing and heating at 45° C. 25 g of 1-ethyl-3-(3-dimethylaminoethyl) carbodiimide (EDAC) were then added, the pump and the sonicator were turned on and the system was kept between 40 and 50° C. for 3 hours. GPC analysis was performed to monitor the progress of the reaction. After 3 hours the sonicator and the pump were turned off and the solution was stiffed at room temperature overnight. The following day 750 mL of acetonitrile were added to precipitate HyPE. This was allowed to stand for 30 minutes after which the supernatant was removed. To this was added 7.5 L of 2% $Na_2CO_3$, previously prepared by dissolving 150 g of $Na_2CO_3$ in 7.5 L in DI water. Vigorous mechanical stiffing for at least 2 hours hydrolyzed urea related byproducts. The solution was neutralized with 6 N HCl while the temperature was kept at ~20-25° C. by passing the solution through a cooled, jacketed flow cell.

EXAMPLE 4

Alkaline Ultrafiltration of HyPE 2.25 kg of $NaHCO_3$ was dissolved in 150 L of 0.1% chlorocresol solution, prepared by dissolving 150 g of chlorocresol in 150 L of DI water. By means of valves, the closed reaction system was diverted so that the digested, neutralized HyPE solution of Example 3 was pumped from the round bottom flask to the centrasette system. By means of constant volume diafiltration with a 10 kDa Omega TFF membrane, 150 L of 1.5% $NaHCO_3$ in 0.1% chlorocresol solution was ultrafiltered, discarding the filtrate, the fraction less than 10 kDa. The pump speed and valves were set such that the retentate flow was ten times the filtrate flow and the feed pressure was less than 40 PSI. GPC analysis was performed to ensure the disappearance of urea-related peaks at ~13.2 min and the HOBT peak at ~17.2 min. The solution was neutralized with 6 N HCl while the temperature was kept at ~20-25° C. by passing the solution through a cooled, jacketed flow cell.

EXAMPLE 5

Extraction of HyPE

Figure 2:
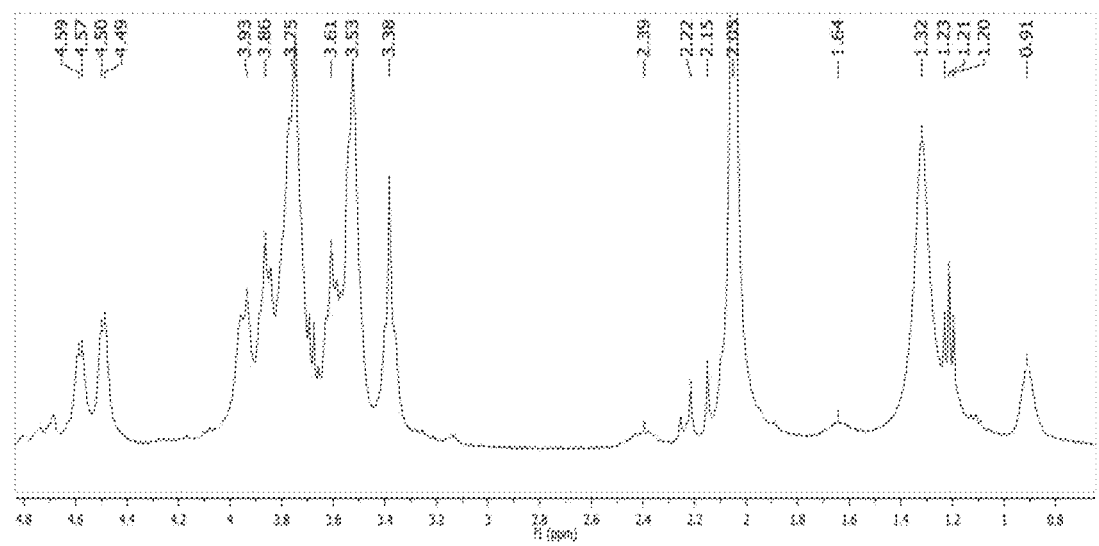
FIG. 2 depicts an NMR spectrum of a hyaluronic acid-phosphatidylethanolamine conjugate (HyPE) prepared according to Example 5.
Figure 3:
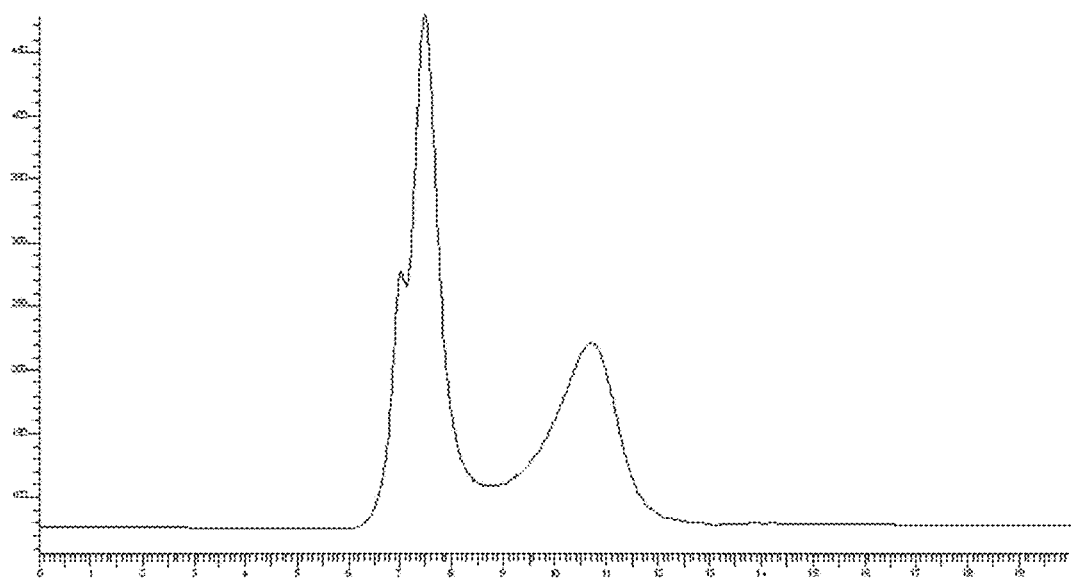
FIG. 3 is an HPLC chromatogram of HyPE prepared according to Example 5.

An extraction solution was made by mixing 3 L of dichloromethane, 3 L of ethanol and 2.25 L of methanol. 7.5 L of the extraction solution was added to a round bottom flask containing 3 L of crude HyPE solution of Example 4. This was stirred vigorously for 15 minutes after which time it was allowed to stand for 45 min. The lower dichloromethane layer was removed. By means of constant volume diafiltration the solution was washed with 100 L of DI water to remove the methanol and ethanol. GPC analysis was performed to ensure the disappearance of peaks at ~14 min. The volume was reduced to 3 L and emptied directly into 2 autoclaved lyoguard containers, closed, frozen and lyophilized to yield HyPE. NMR and HPLC data for isolated HyPE are shown in FIG. 2 and FIG. 3.

EXAMPLE 6

In Vitro Stimulation of RAW 264.7 Cells

Figure 4:
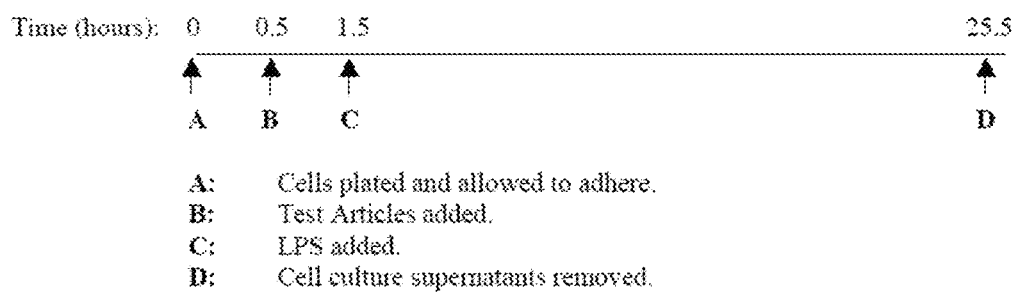
FIG. 4 depicts a schematic representation of the in vitro stimulation of RAW 264.7 cells.

In vitro stimulation of RAW 364.7 cells was carried out according to the schematic depicted in FIG. 4. Each Test Article was prepared in DMEM (no FBS) at 10 mg/ml (all Test Article concentrations were corrected for moisture content), vortexed, heated at 50° C. for 5 minutes, sonicated for 5 minutes and filtered through a 0.2 micron syringe filter. 2×Test Article working solutions of 0.6 mg/ml, 0.2 mg/ml and 0.06 mg/ml were prepared by diluting the 10 mg/ml stock solutions in CM. A 2.55 mM solution of dexamethasone prepared in ethanol was diluted to 2 µM (2×working solution) in CM. The vehicle control solution was CM. A 1 mg/ml solution of LPS (made in 1× PBS) was diluted in CM to 10 µg/ml. RAW 264.7 cells were grown for XX passages (subculture every 3-4 days) in CM at 37° C. with 5% $CO_2$. 0.5 ml of cells at 1×106 cells/ml was plated in 24-well tissue culture plates. Cells were allowed to adhere for 30 minutes at 37° C. with 5% $CO_2$ prior to treatment. The appropriate Test Article, dexamethasone or vehicle control working solutions were added to the cells. Cells were incubated for 1 hour at 37° C. with 5% $CO_2$ prior to LPS treatment. 110 µl of CM was added to the −LPS plates. 110 µl of 10 µg/ml LPS was added to the +1 µg/ml LPS plates. The plates were incubated for 24 hours at 37° C. with 5% $CO_2$.

EXAMPLE 7

Supernatant Harvesting/XXT Assay

Figure 5:
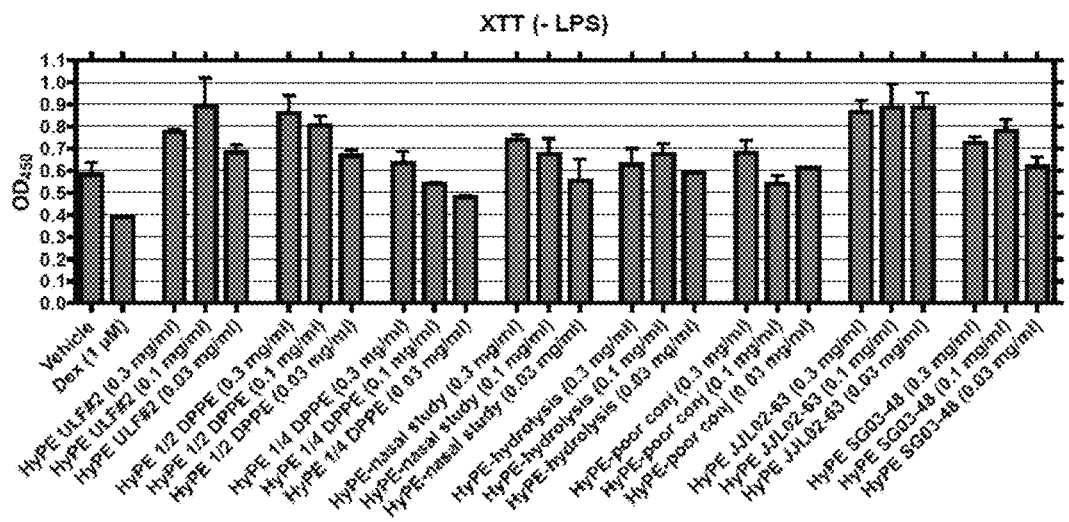
FIG. 5 depicts the mean XTT reduction ($OD_{450}$) by RAW 264.7 cells in the absence of LPS. Error bars represent standard deviations.
Figure 6:
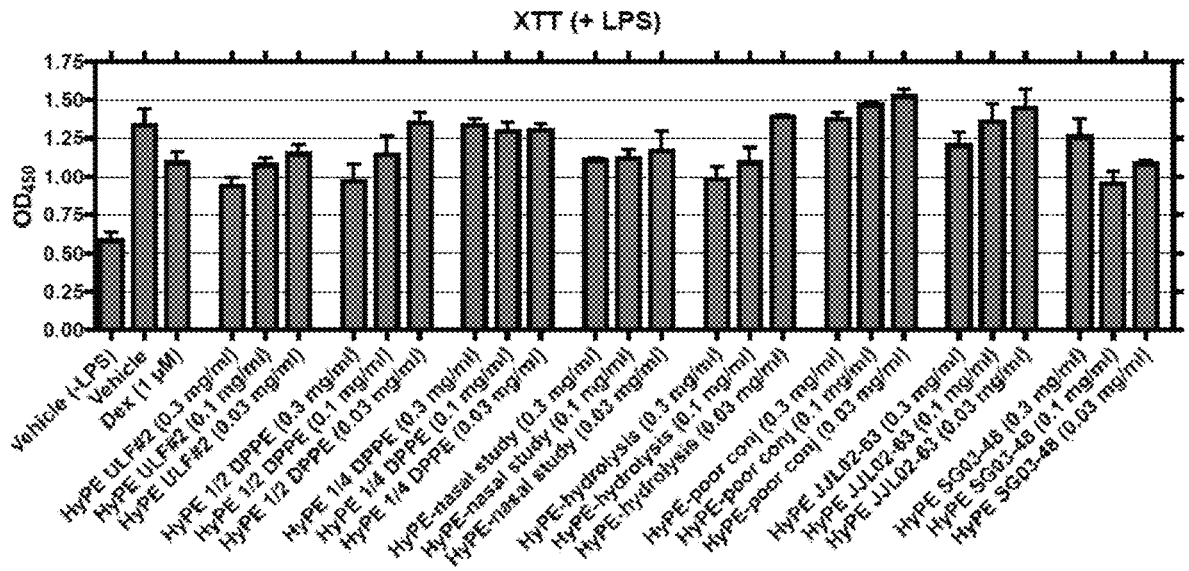
FIG. 6 depicts the mean XTT reduction ($OD_{450}$) by LPS-stimulated RAW 264.7 cells. Error bars represent standard deviations.
Figure 22:
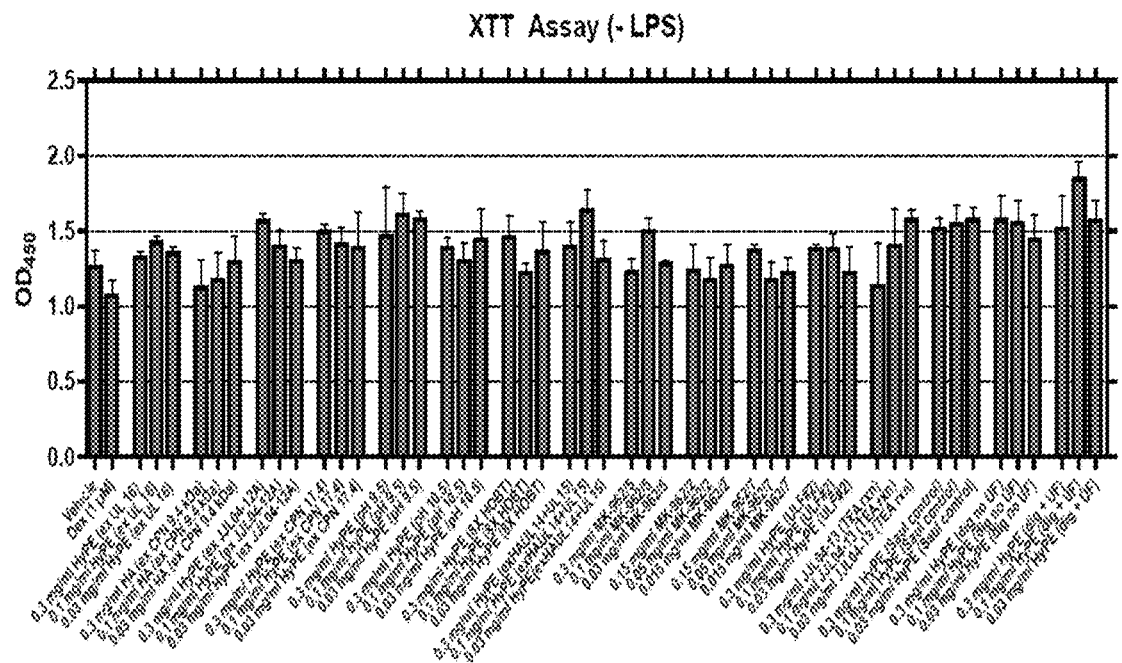
FIG. 22 depicts the mean XTT reduction ($OD_{450}$) by RAW 264.7 cells in the absence of LPS. Error bars represent standard deviations.
Figure 23:
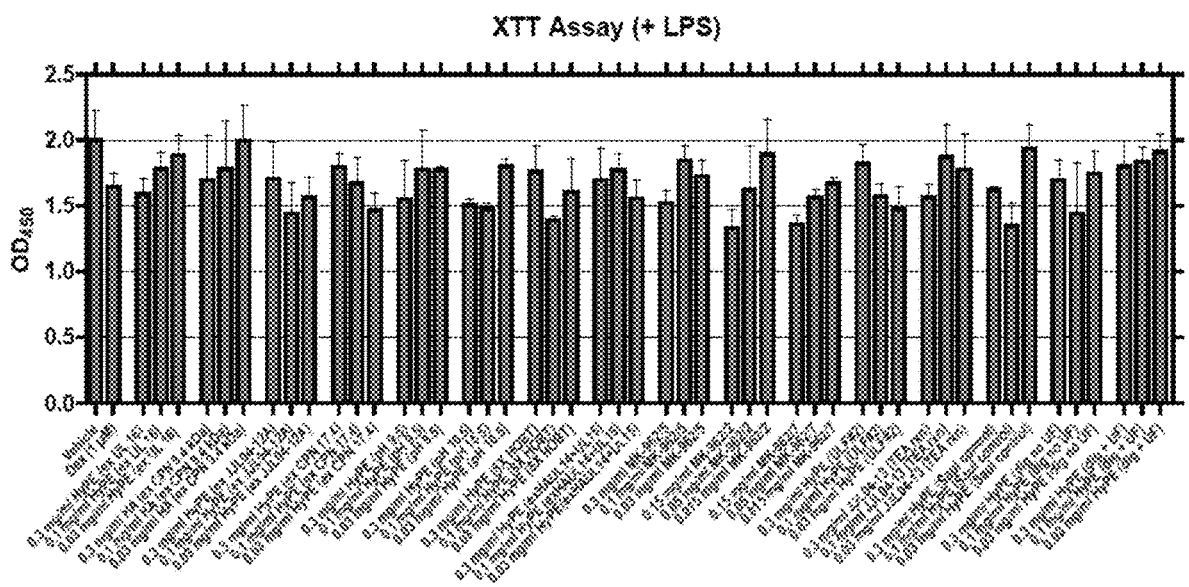
FIG. 23 depicts the mean XTT reduction ($OD_{450}$) by LPS-stimulated RAW 264.7 cells. Error bars represent standard deviations.

Cell culture supernatants were collected after 24 hours of LPS treatment and stored at −30° C. until assayed. 400 µl of media was left in each cell culture well for the XTT assay. 400 µl of media was added to a cell-free culture well for use as a blank in the XTT assay. 200 µl of activated XTT reagent was added to each well. Plates were incubated for 1 hour at 37° C. with 5% $CO_2$. 100 µl was removed from each well and read at 450 nm (630 nm correction) using a ThermoMax microplate reader (Molecular Devices, Sunnyvale, Calif.). XTT data relating to high molecular weight HyPE compositions are shown in FIG. 5 and FIG. 6. XTT data relating to low molecular weight HyPE compositions are shown in FIG. 22 and FIG. 23.

EXAMPLE 8

Cytokine/Chemokine Assays

Figure 7:
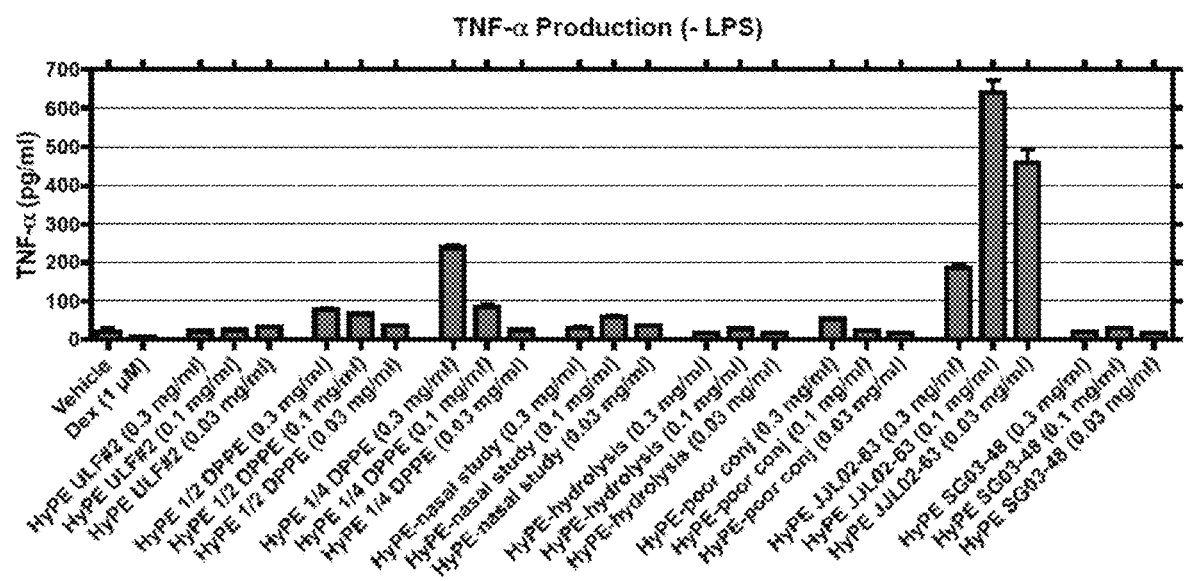
FIG. 7 depicts the mean TNF-α release from RAW 264.7 cells in the absence of LPS. Error bars represent standard deviations.
Figure 8:
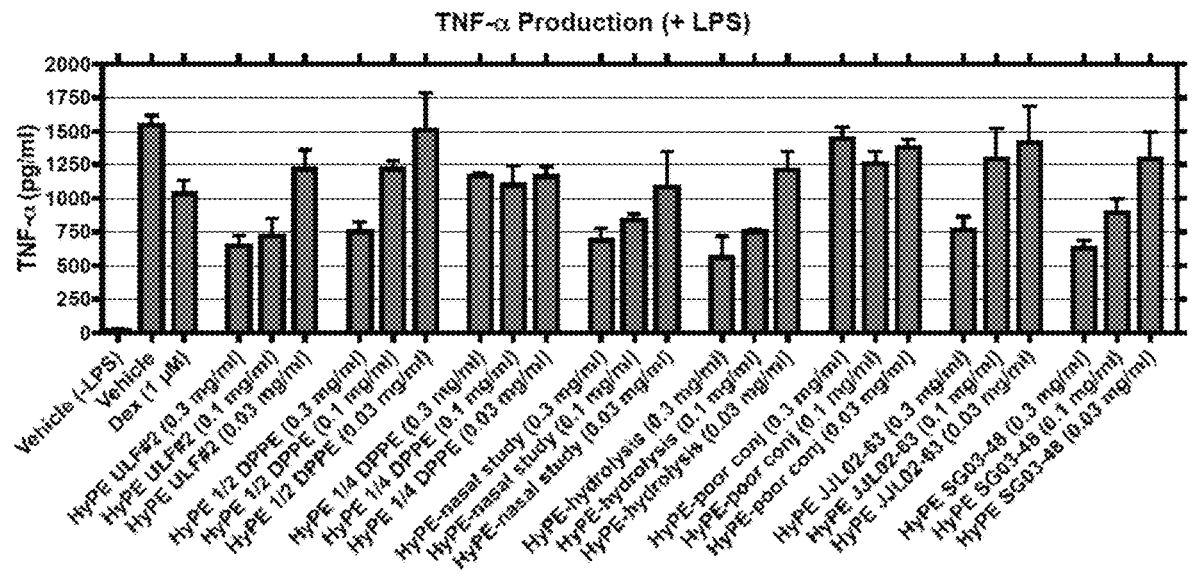
FIG. 8 depicts the mean TNF-α release from LPS-stimulated RAW 264.7 cells. Error bars represent standard deviations.
Figure 9:
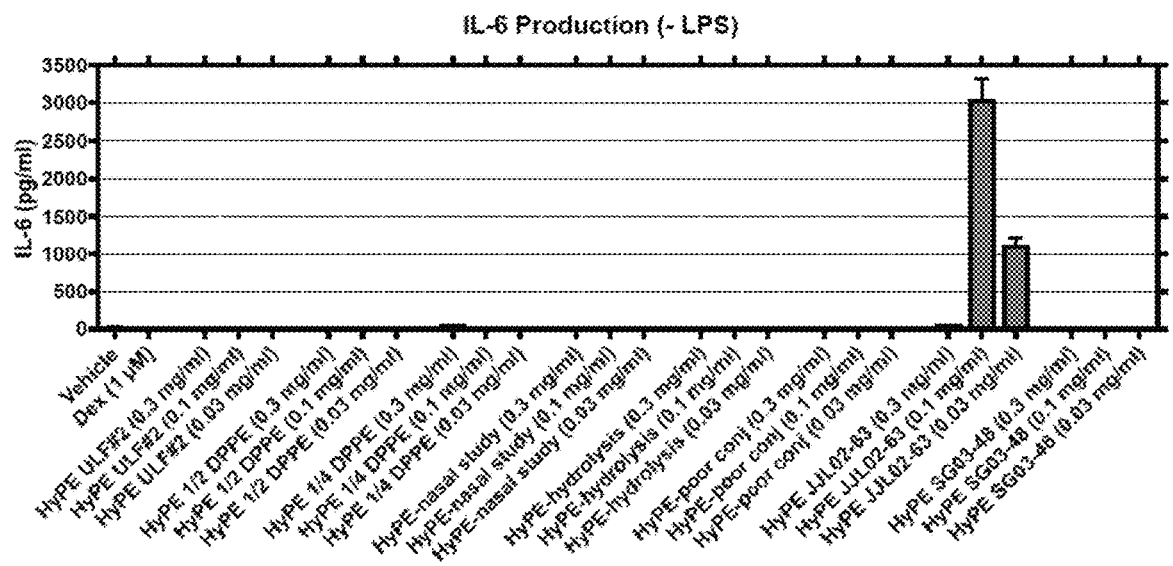
FIG. 9 depicts the mean IL-6 release from RAW 264.7 cells in the absence of LPS. Error bars represent standard deviations.
Figure 10:
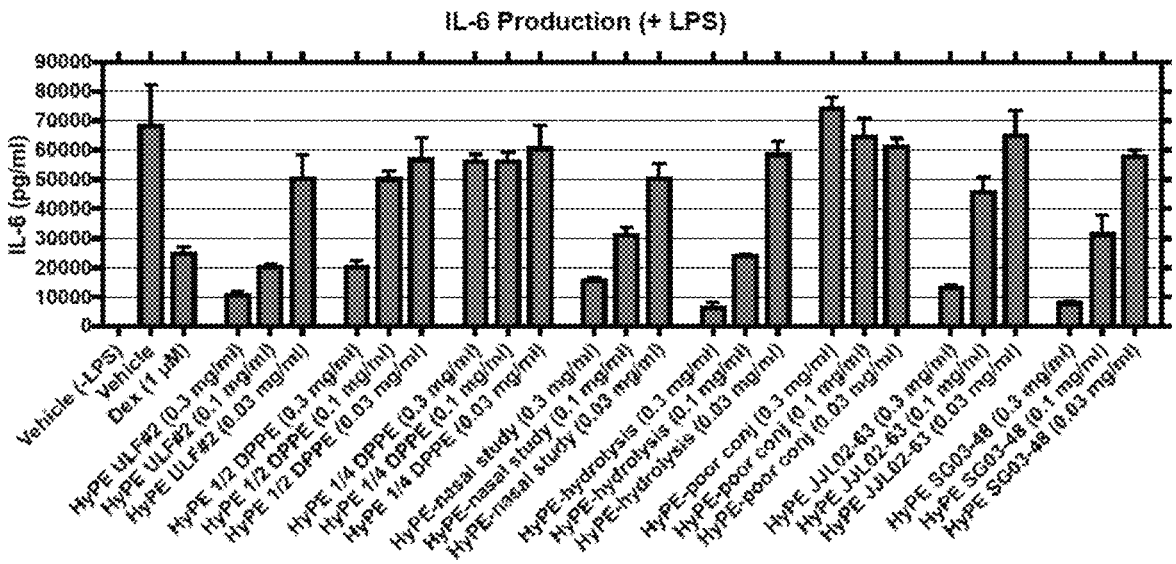
FIG. 10 depicts the mean IL-6 release from LPS-stimulated RAW 264.7 cells. Error bars represent standard deviations.
Figure 11:
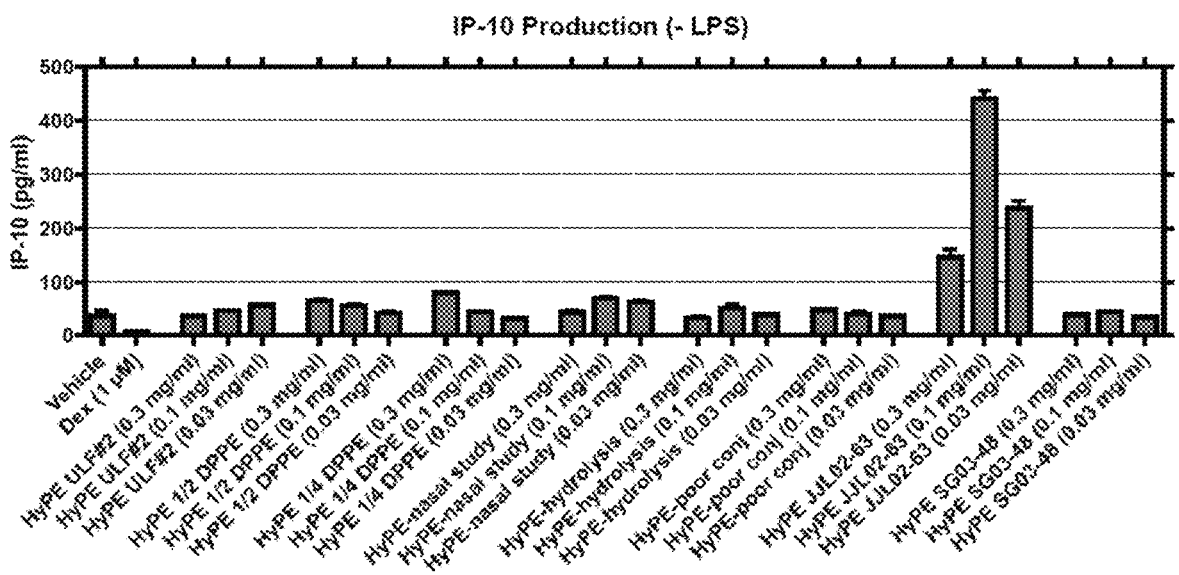
FIG. 11 depicts the mean IP-10 release from RAW 264.7 cells in the absence of LPS. Error bars represent standard deviations.
Figure 12:
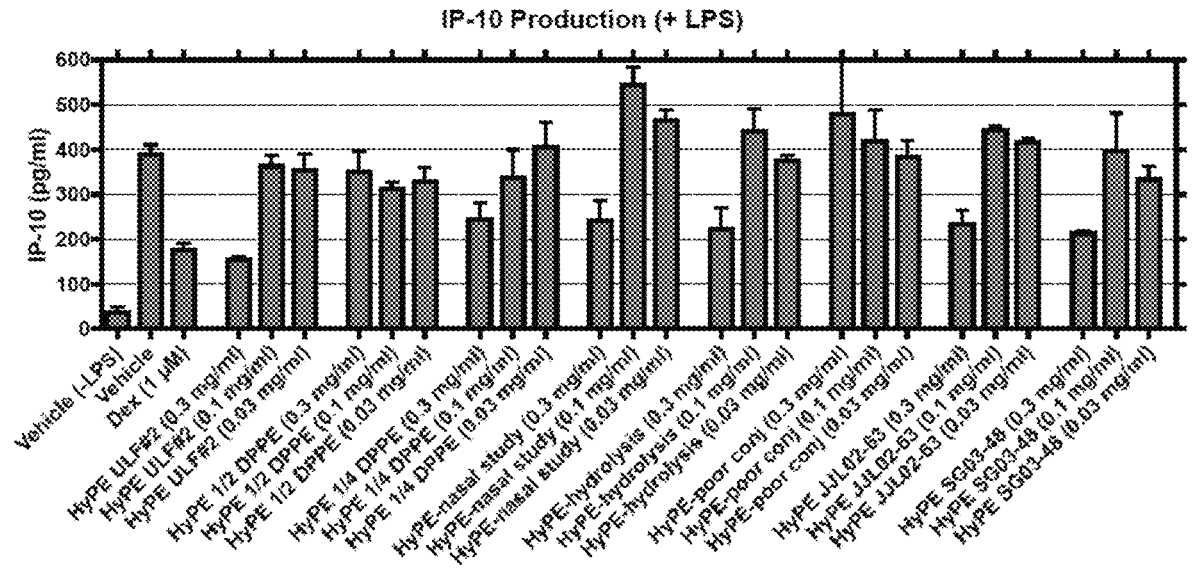
FIG. 12 depicts the mean IP-10 release from LPS-stimulated RAW 264.7 cells. Error bars represent standard deviations.
Figure 15:
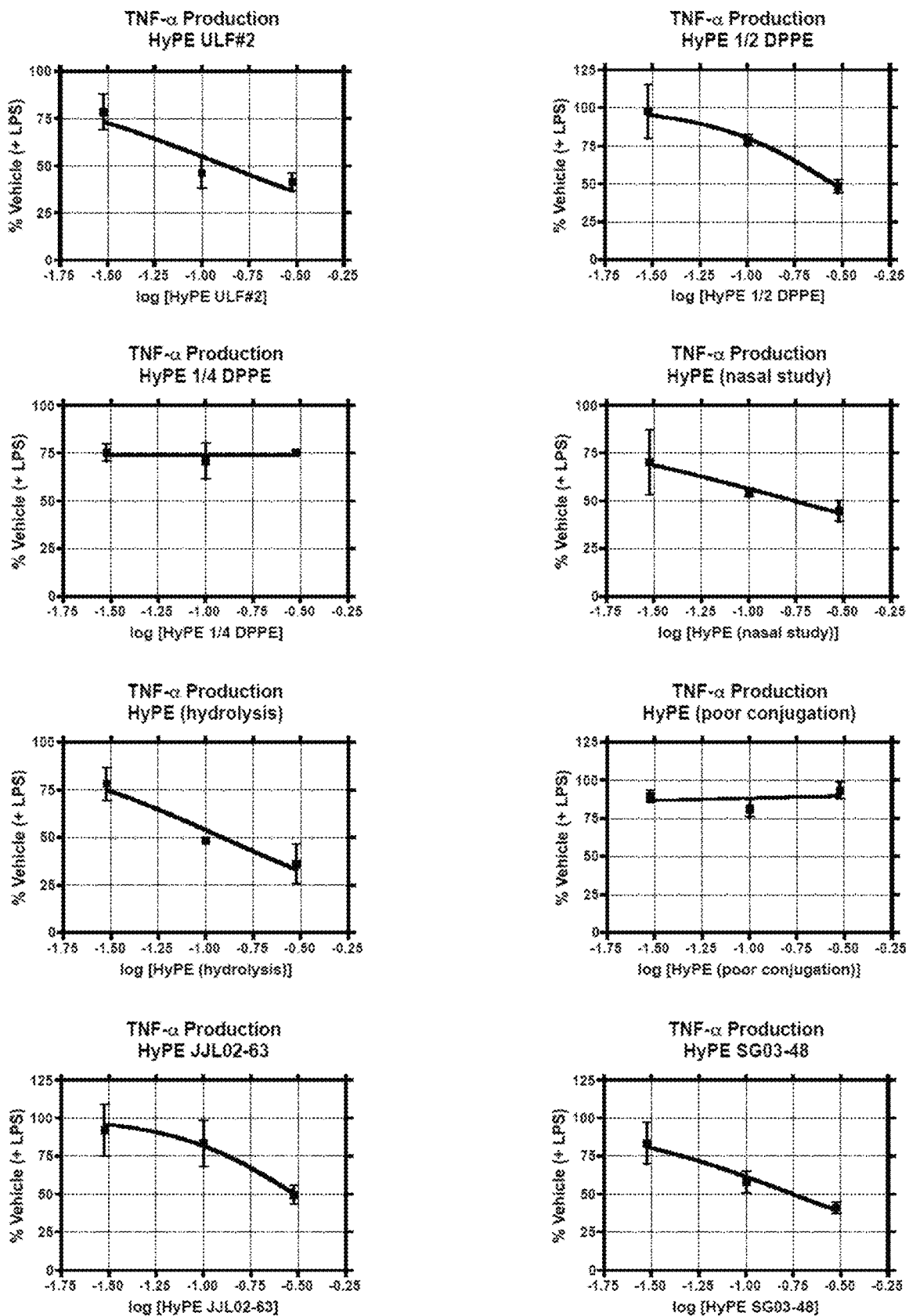
FIG. 15 depicts dose-response curves for TNF-α production (+LPS). Data fit using Prism 4, Sigmoidal dose-response curve (variable slope): Y=Bottom+(Top+Bottom)/(1+10^((LOGIC50−X)*HillSlope)). X is the log of Test Article concentration, Y is the response. Constraints Bottom=0, Top=100.
Figure 16:
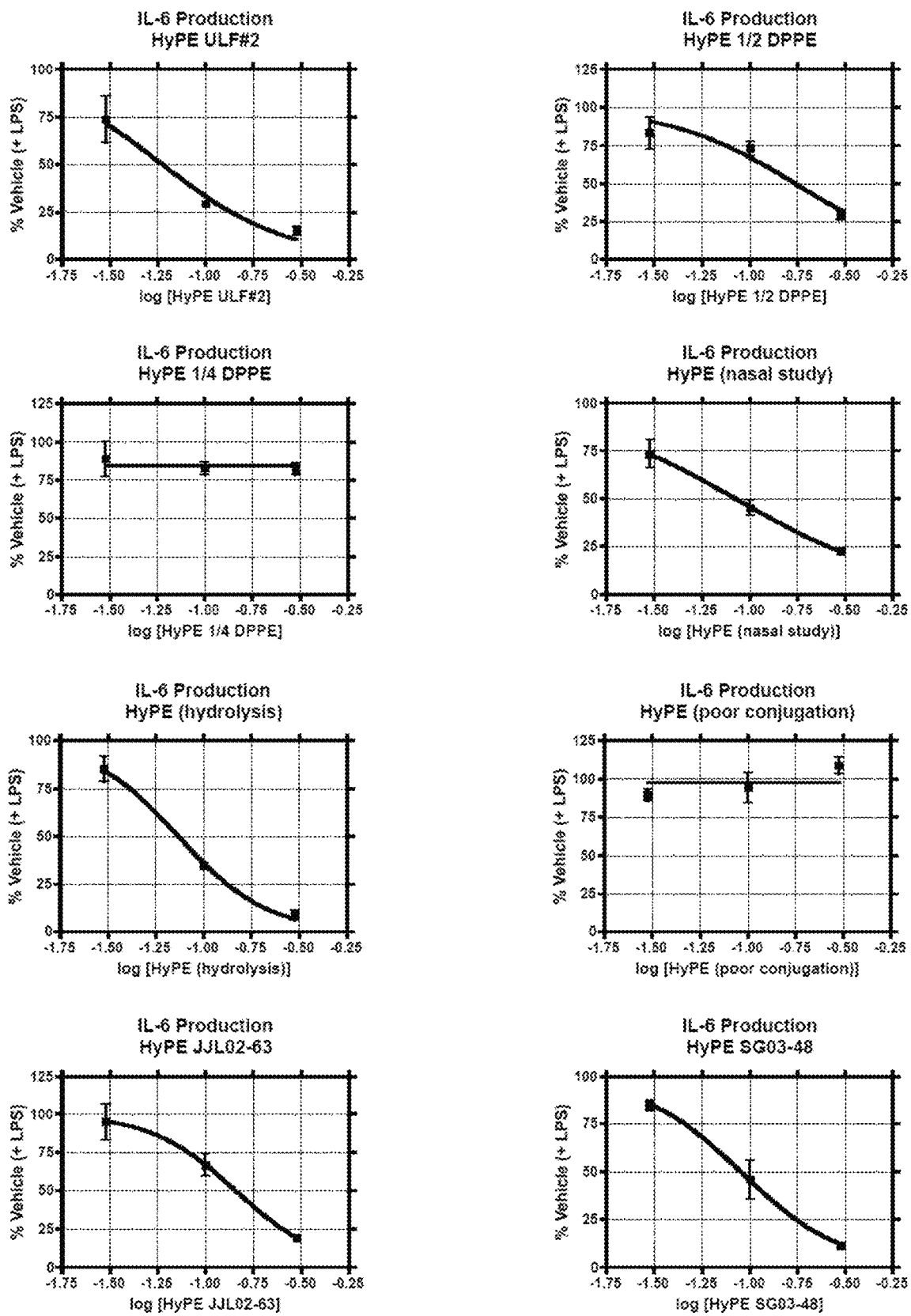
FIG. 16 depicts dose-response curves for IL-6 production (+LPS). Data fit using Prism 4, Sigmoidal dose-response curve (variable slope): Y=Bottom+(Top+Bottom)/(1+10^((LOGIC50−X)*HillSlope)). X is the log of Test Article concentration, Y is the response. Constraints Bottom=0, Top=100.
Figure 17:
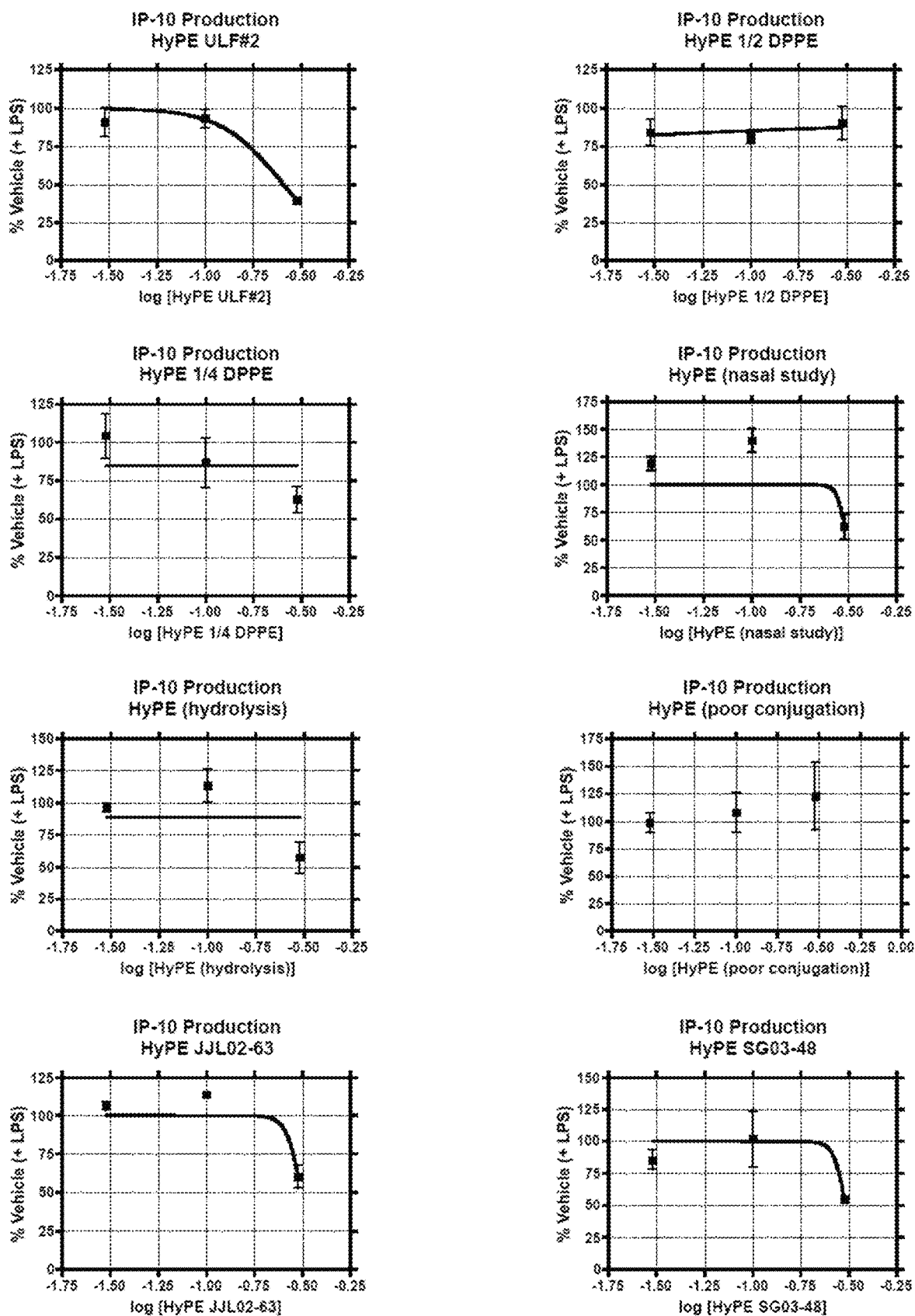
FIG. 17 depicts dose-response curves for IP-10 production (+LPS). Data fit using Prism 4, Sigmoidal dose-response curve (variable slope): Y=Bottom+(Top+Bottom)/(1+10^((LOGIC50−X)*HillSlope)). X is the log of Test Article concentration, Y is the response. Constraints Bottom=0, Top=100.
Figure 24:
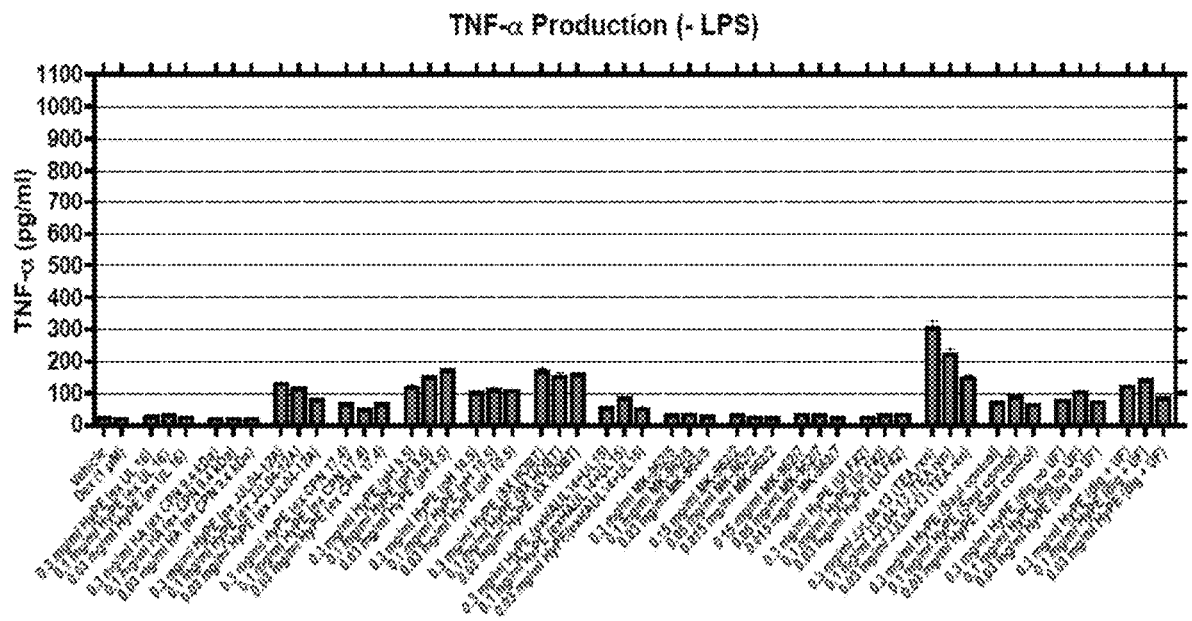
FIG. 24 depicts the mean TNF-α release from RAW 264.7 cells in the absence of LPS. Error bars represent standard deviations.
Figure 25:
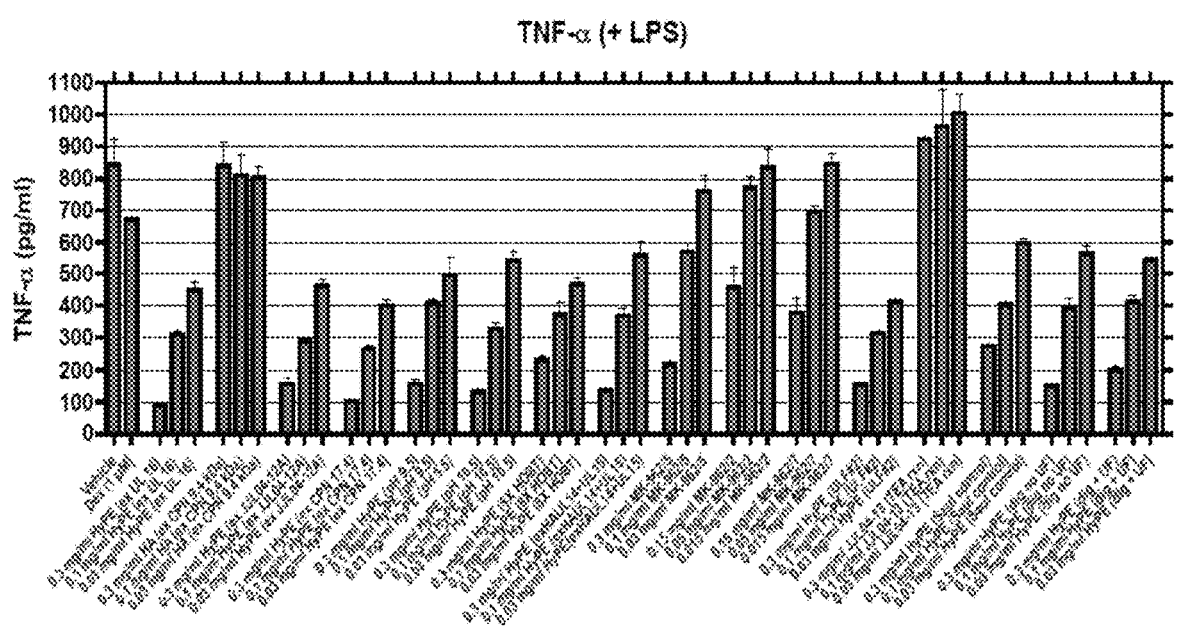
FIG. 25 depicts the mean TNF-α release from LPS-stimulated RAW 264.7 cells. Error bars represent standard deviations.
Figure 26:
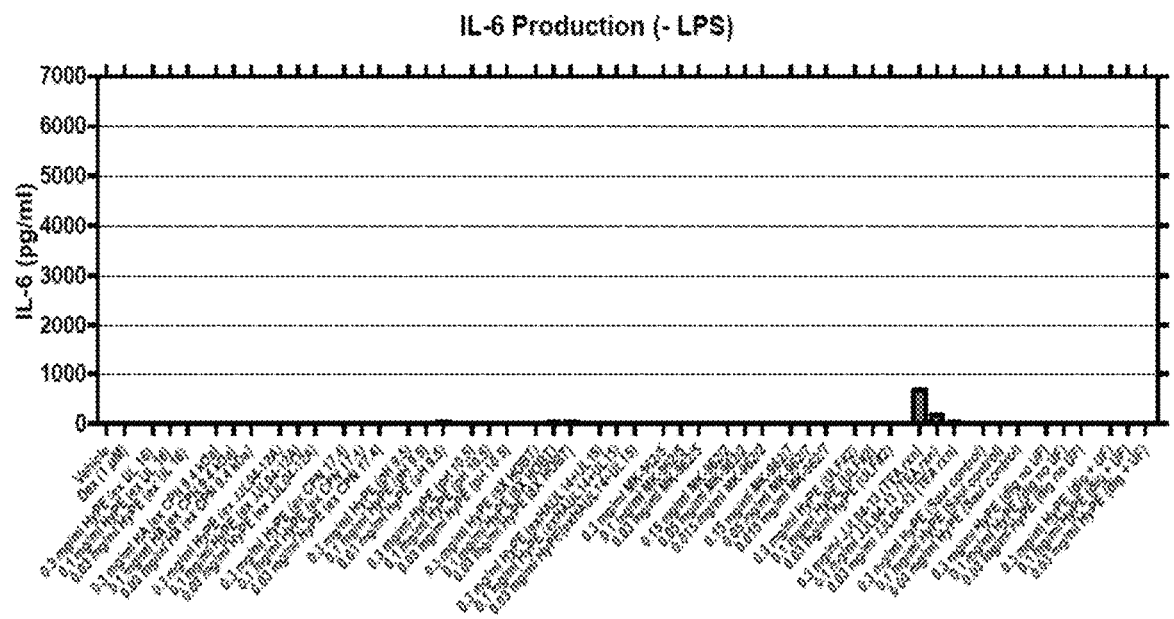
FIG. 26 depicts the mean IL-6 release from RAW 264.7 cells in the absence of LPS. Error bars represent standard deviations.
Figure 27:
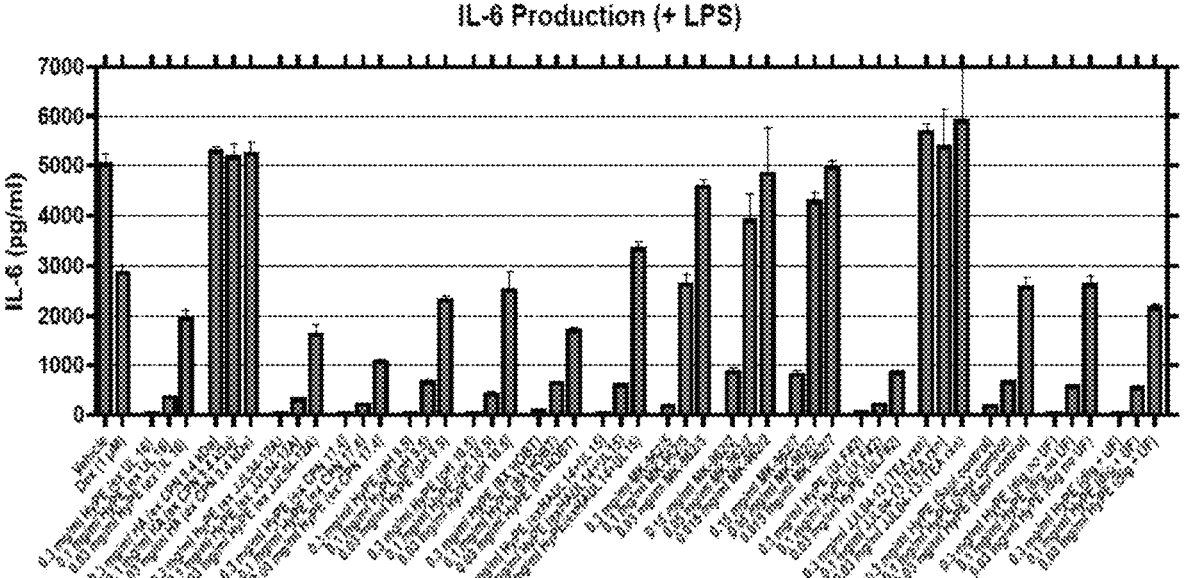
FIG. 27 depicts the mean IL-6 release from LPS-stimulated RAW 264.7 cells. Error bars represent standard deviations.
Figure 28:
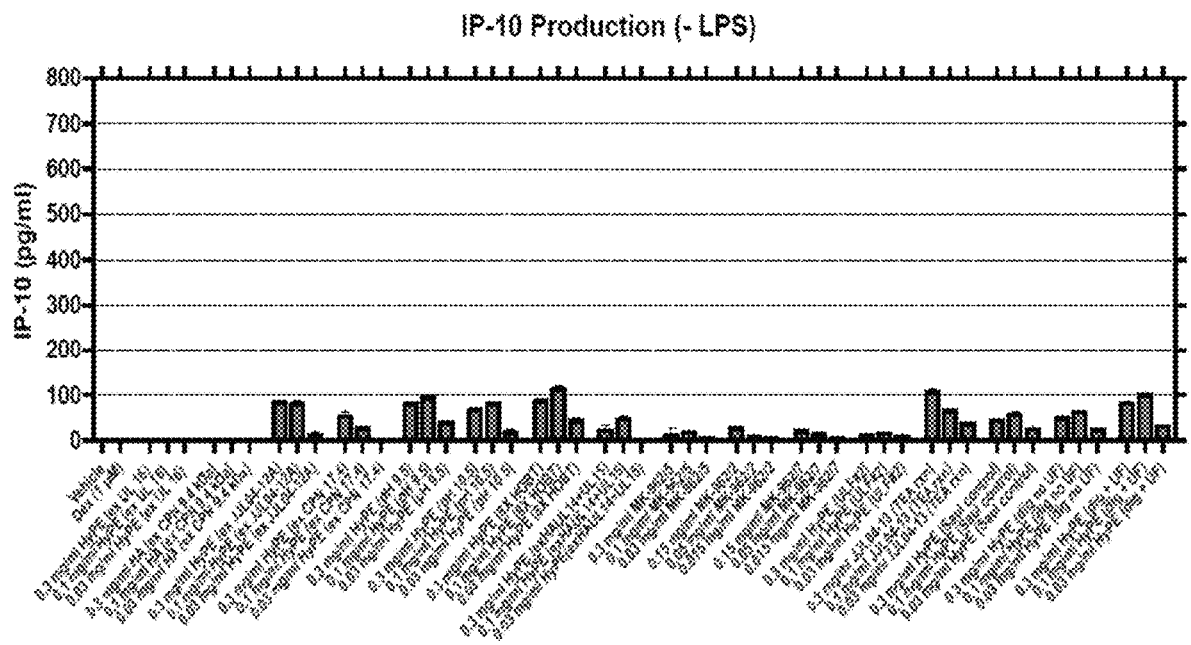
FIG. 28 depicts the mean IP-10 release from RAW 264.7 cells in the absence of LPS. Error bars represent standard deviations.
Figure 29:
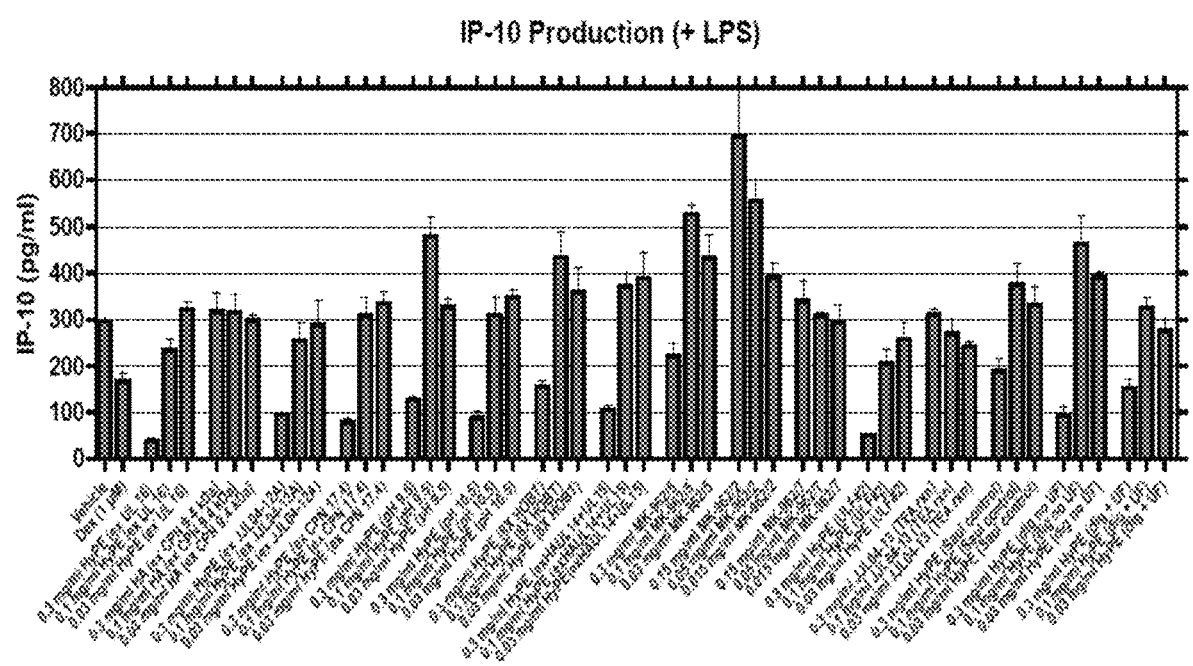
FIG. 29 depicts the mean IP-10 release from LPS-stimulated RAW 264.7 cells. Error bars represent standard deviations.
Figure 32:
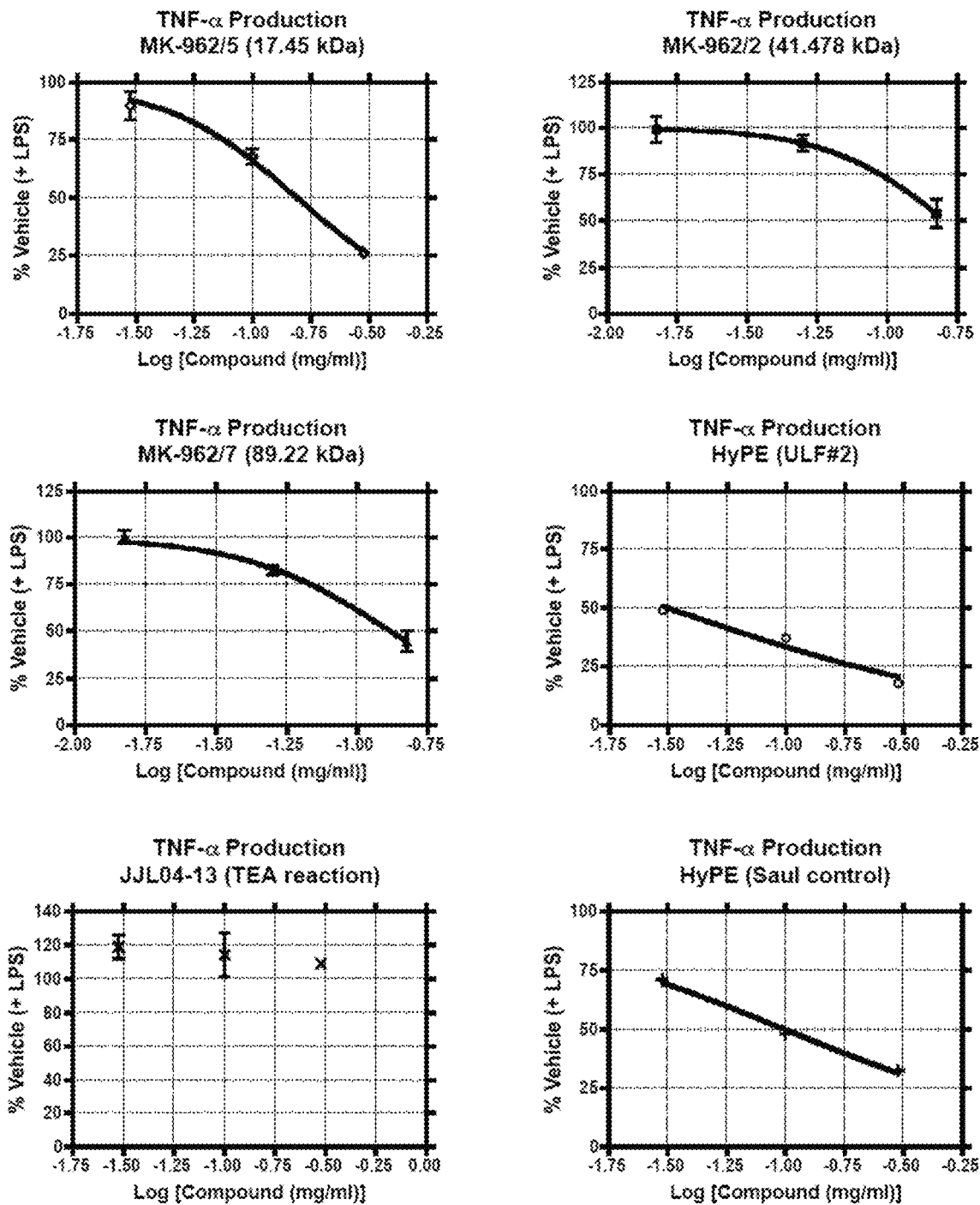
FIG. 32 depicts dose-response curves for TNF-α production (+LPS). Data fit using Prism 4, Sigmoidal dose-response curve (variable slope): Y=Bottom+(Top+Bottom)/(1+10^((LOGIC50−X)*HillSlope)). X is the log of Test Article concentration, Y is the response. Constraints Bottom=0, Top=100.
Figure 32:
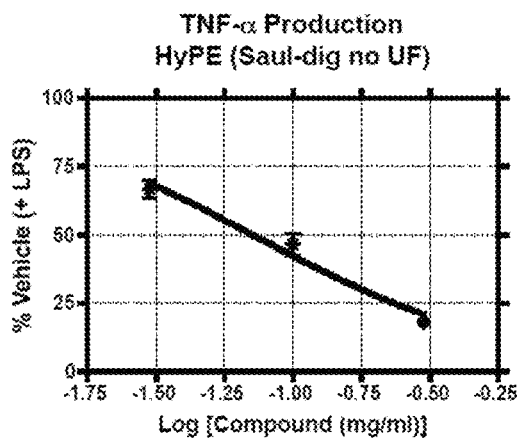
Figure 32:
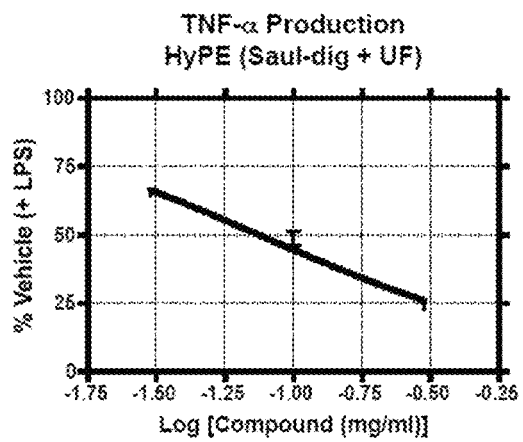
Figure 32:
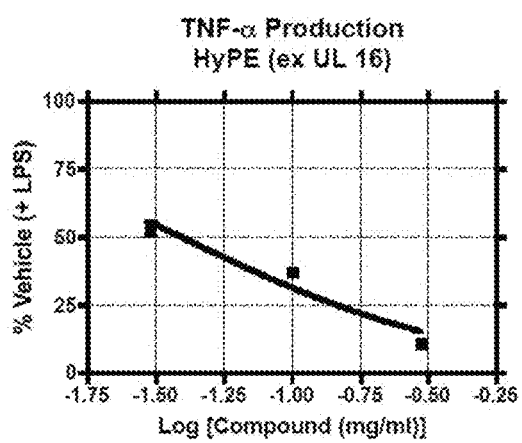
Figure 32:
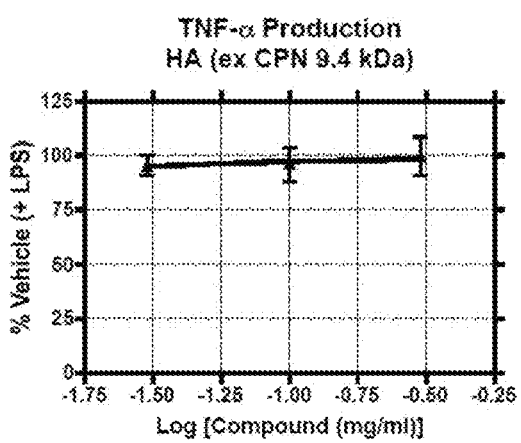
Figure 32:
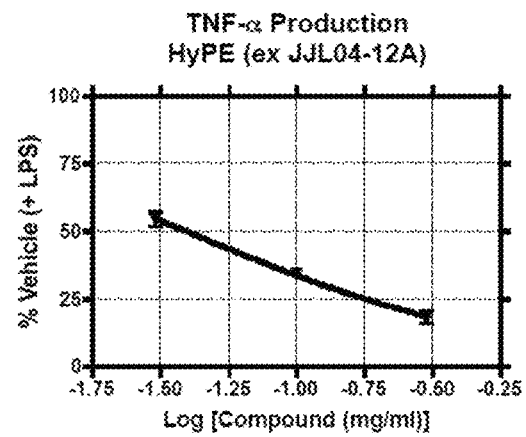
Figure 32:
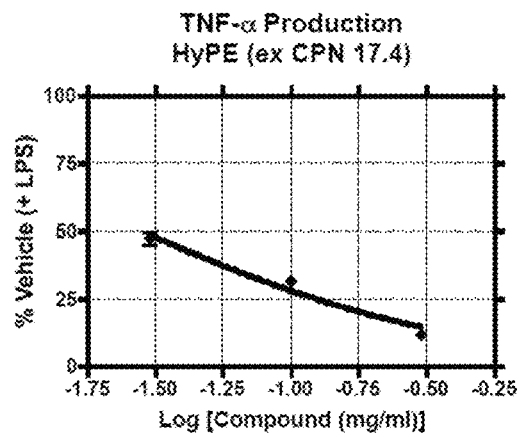
Figure 32:
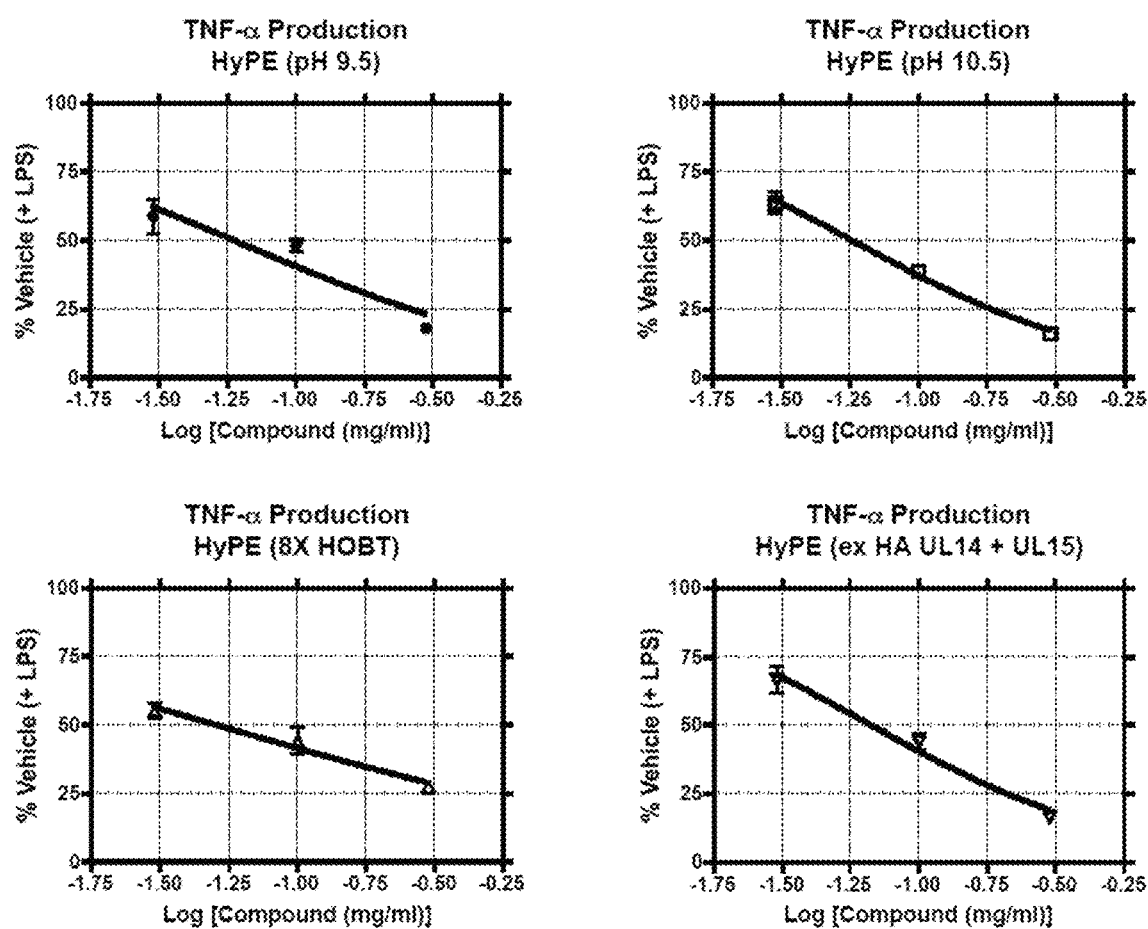
Figure 33:
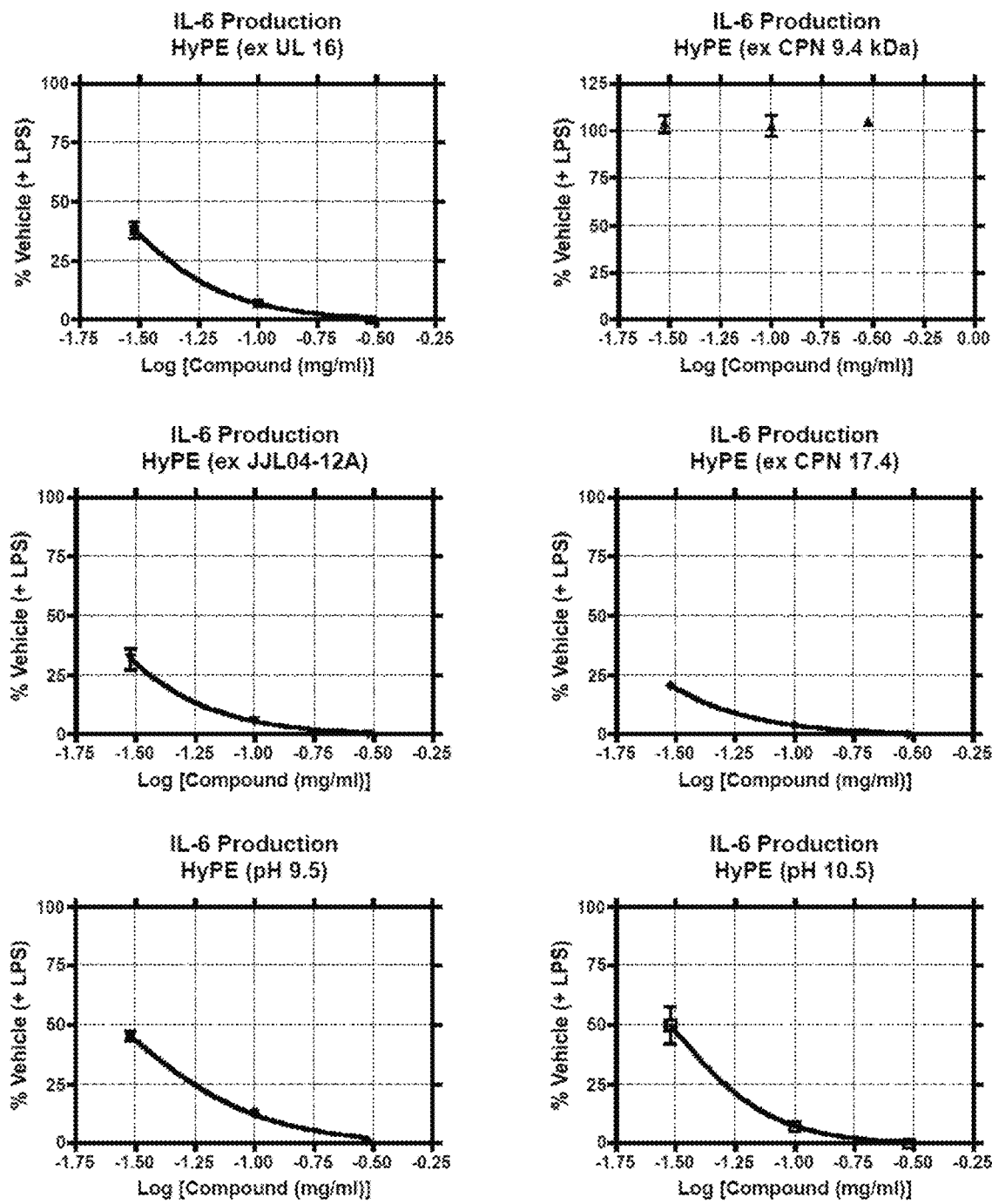
FIG. 33 depicts dose-response curves for IL-6 production (+LPS). Data fit using Prism 4, Sigmoidal dose-response curve (variable slope): Y=Bottom+(Top+Bottom)/(1+10^((LOGIC50−X)*HillSlope)). X is the log of Test Article concentration, Y is the response. Constraints Bottom=0, Top=100.
Figure 33:
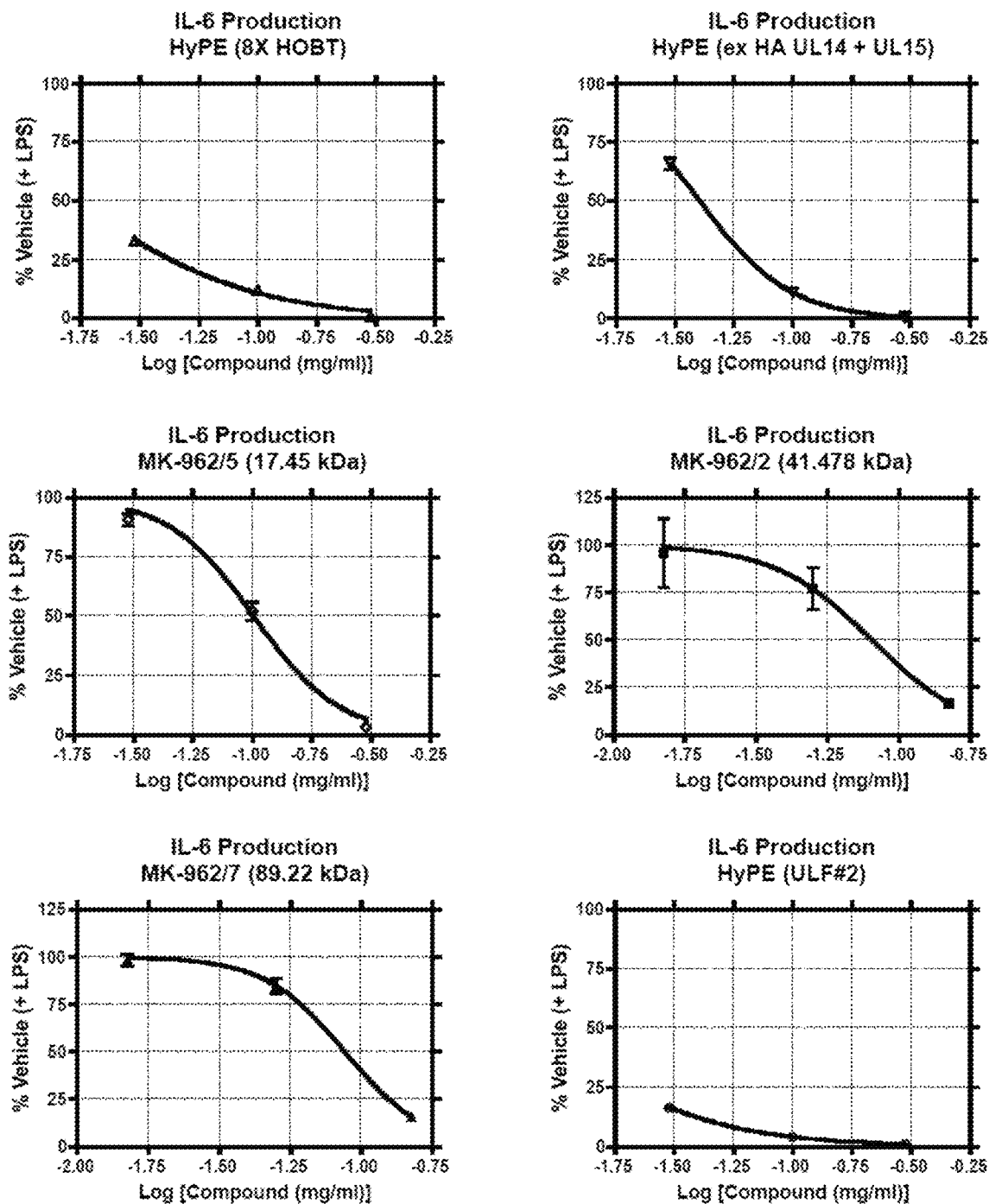
Figure 33:
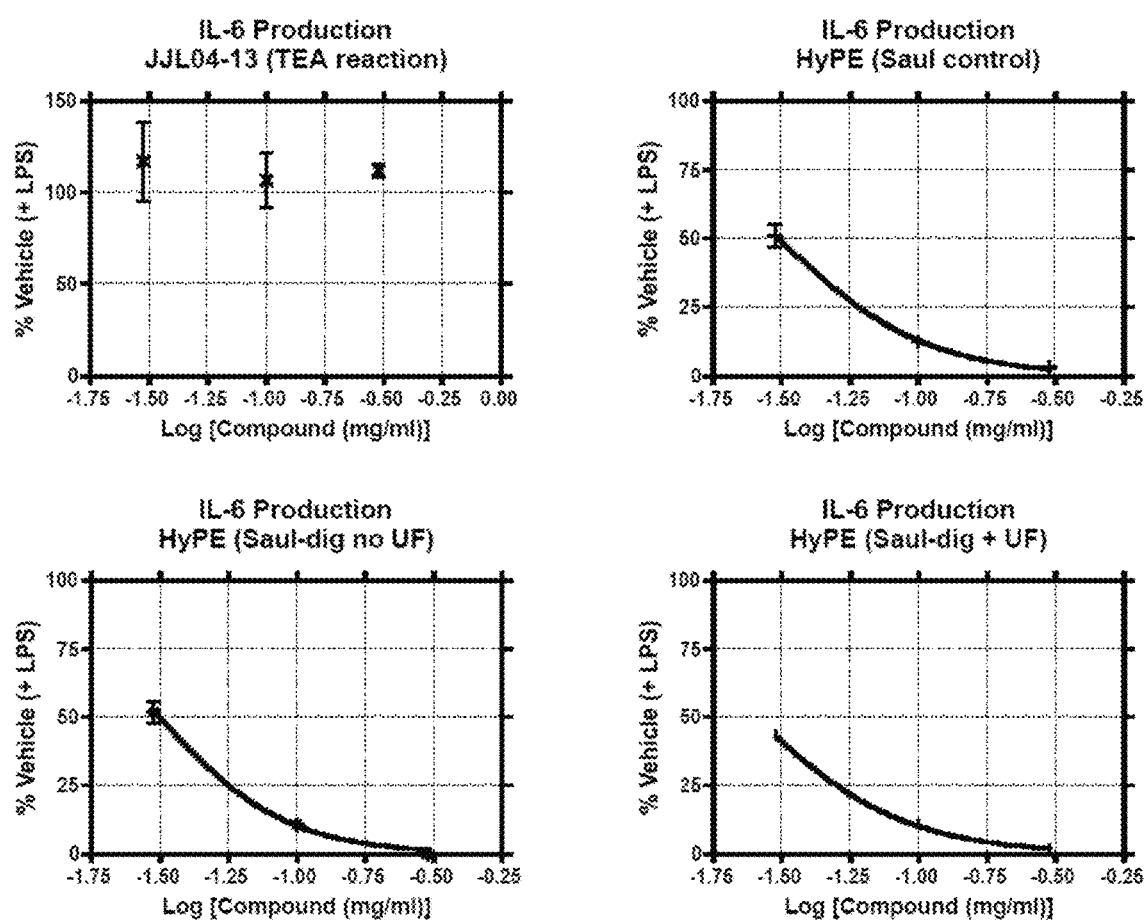
Figure 34:
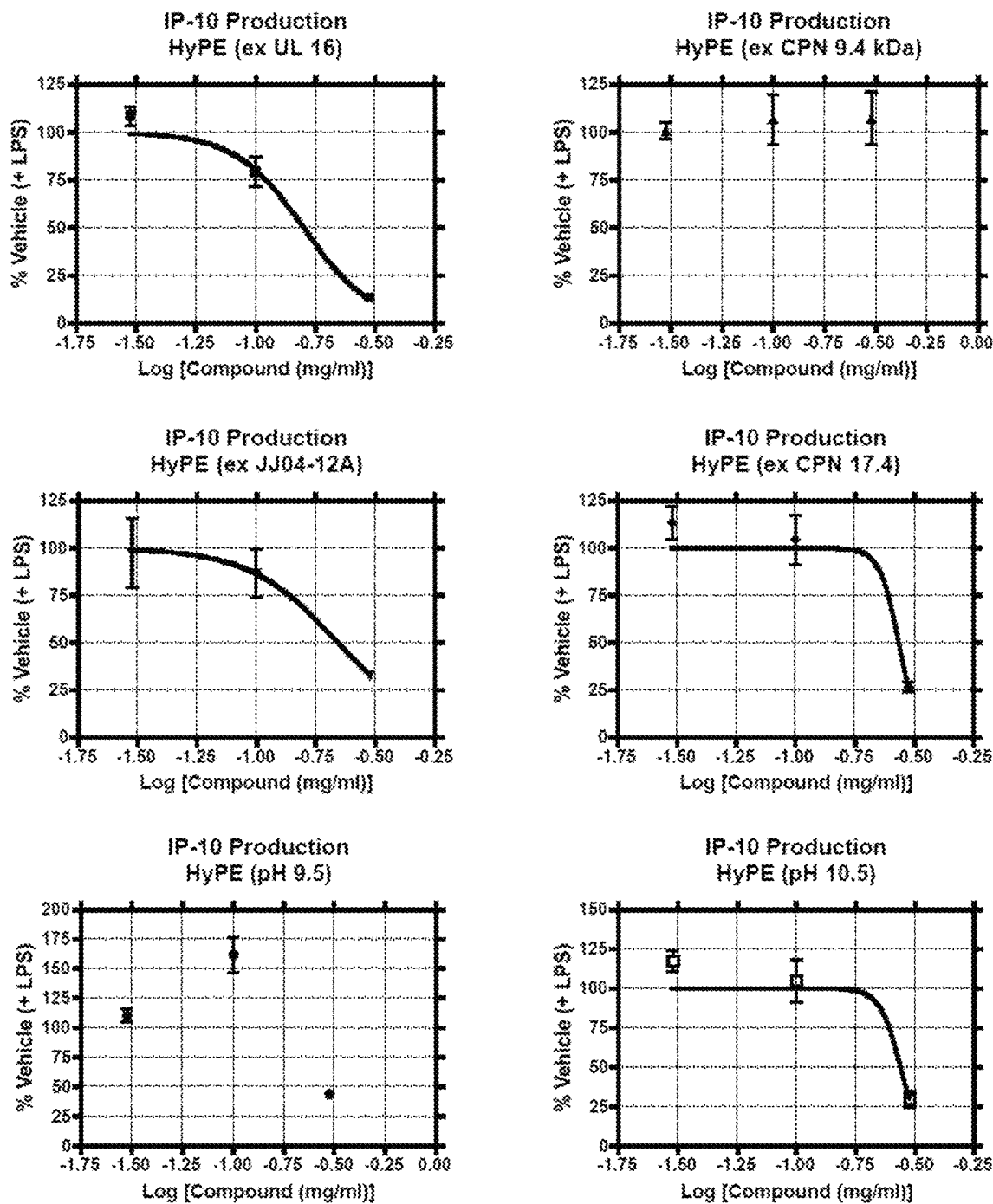
FIG. 34 depicts dose-response curves for IP-10 production (+LPS). Data fit using Prism 4, Sigmoidal dose-response curve (variable slope): Y=Bottom+(Top+Bottom)/(1+10^((LOGIC50−X)*HillSlope)). X is the log of Test Article concentration, Y is the response. Constraints Bottom=0, Top=100.
Figure 34:
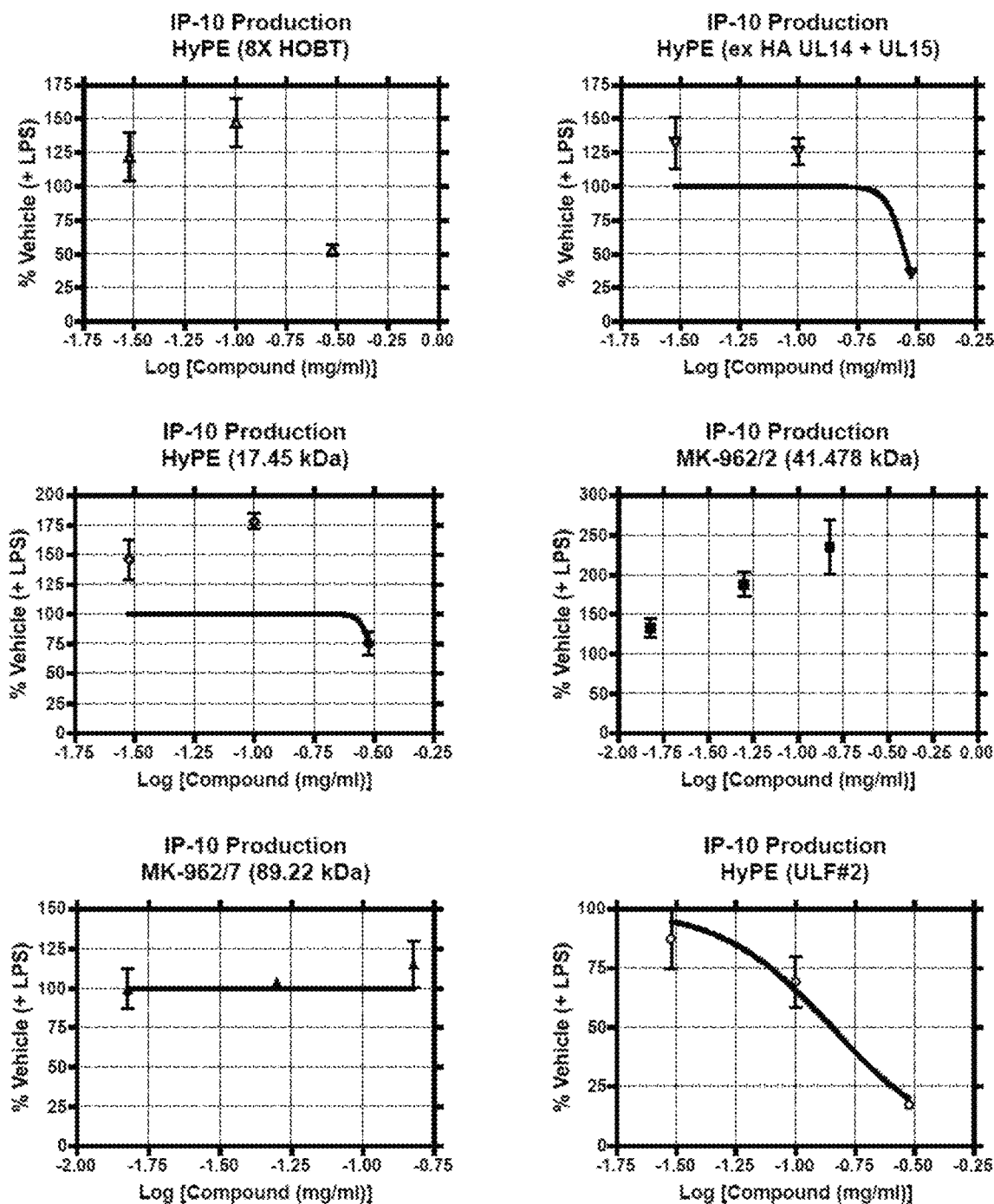
Figure 34:
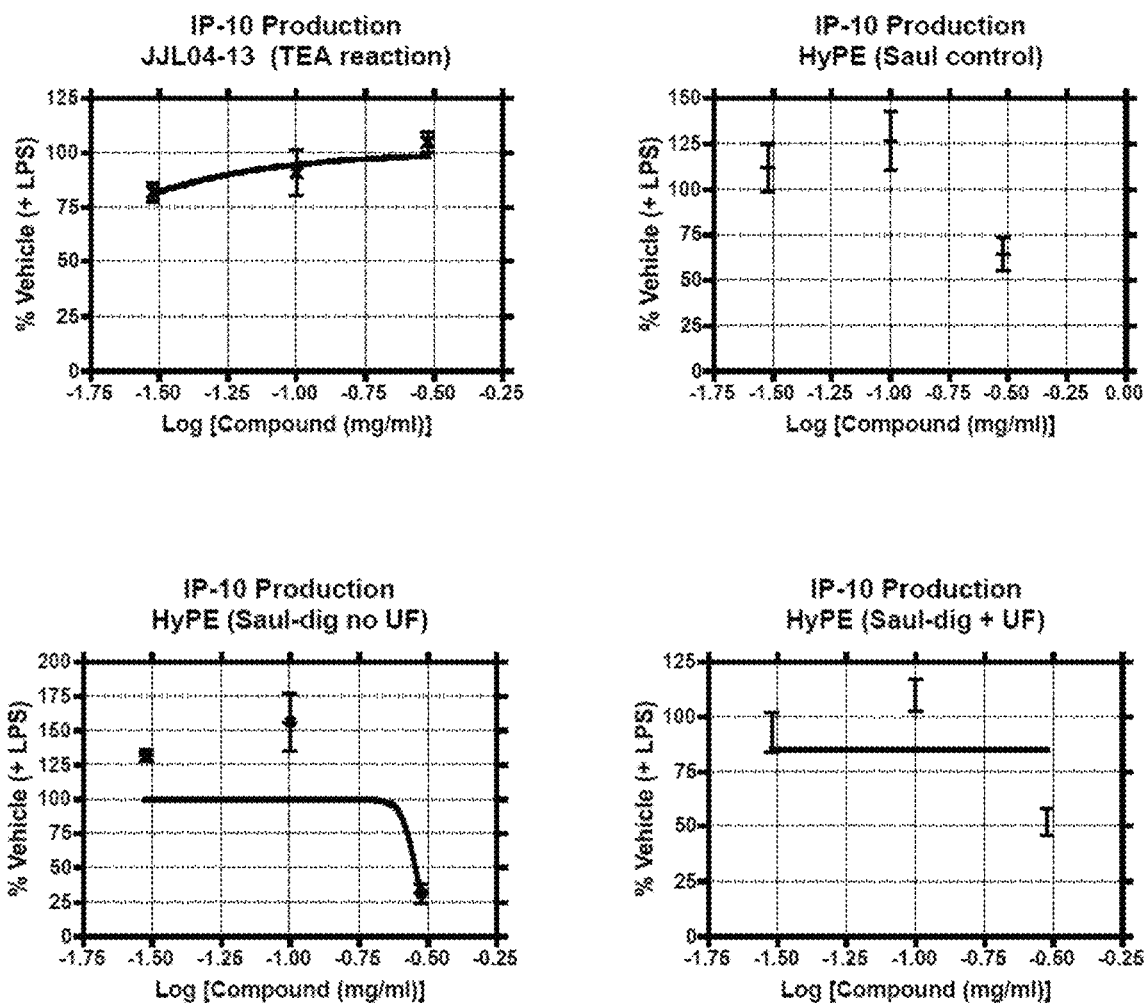

Cell culture supernatants were assayed for IL-6, TNF-α and IP-10 using a Luminexbased assay according to the manufacturer's instructions. Data were collected using a Luminex 100 (Luminex Corporation, Austin, Tex.). Standard curves were generated using a 5-parameter logistic curve-fitting equation weighted by 1/y (StarStation V 2.0; Applied Cytometry Systems, Sacramento, Calif.). Each sample reading was interpolated from the appropriate standard curve. Calculated concentrations were multiplied by the appropriate dilution factor when necessary. TNF-α data relating to high molecular weight HyPE compositions are shown in FIG. 7, FIG. 8 and FIG. 15. TNF-α data relating to low molecular weight HyPE compositions are shown in FIG. 24, FIG. 25 and FIG. 32. IL-6 data relating to high molecular weight HyPE compositions are shown in FIG. 9, FIG. 10 and FIG. 16. IL-6 data relating to low molecular weight HyPE compositions are shown in FIG. 26, FIG. 27 and FIG. 33. IP-10 data relating to high molecular weight HyPE compositions are shown in FIG. 11, FIG. 12 and FIG. 17. IP-10 data relating to low molecular weight HyPE compositions are shown in FIG. 28, FIG. 29 and FIG. 34.

Figure 13:
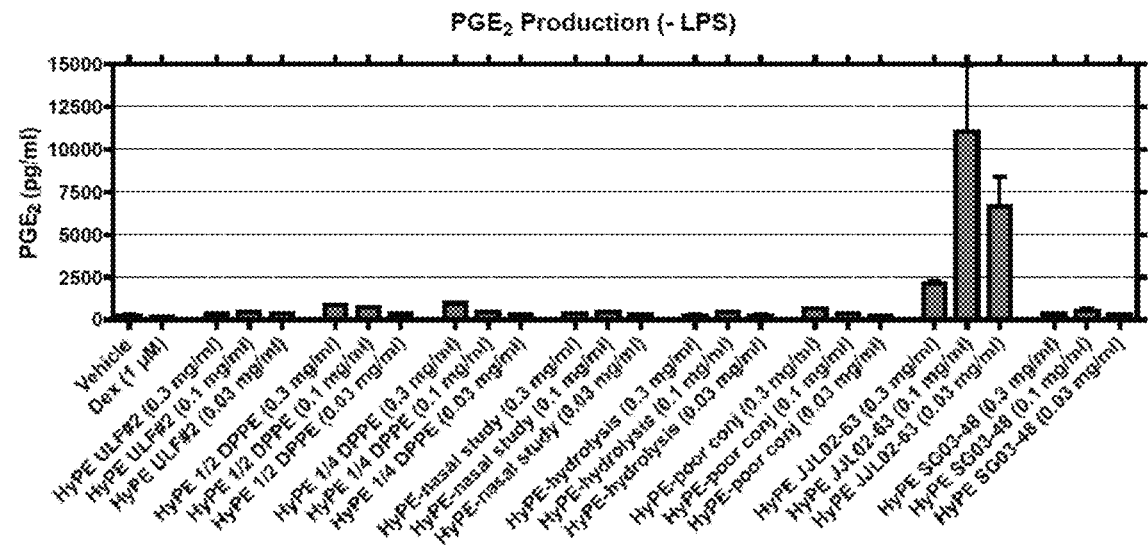
FIG. 13 depicts the mean $PGE_2$ release from RAW 264.7 cells in the absence of LPS. Error bars represent standard deviations.
Figure 14:
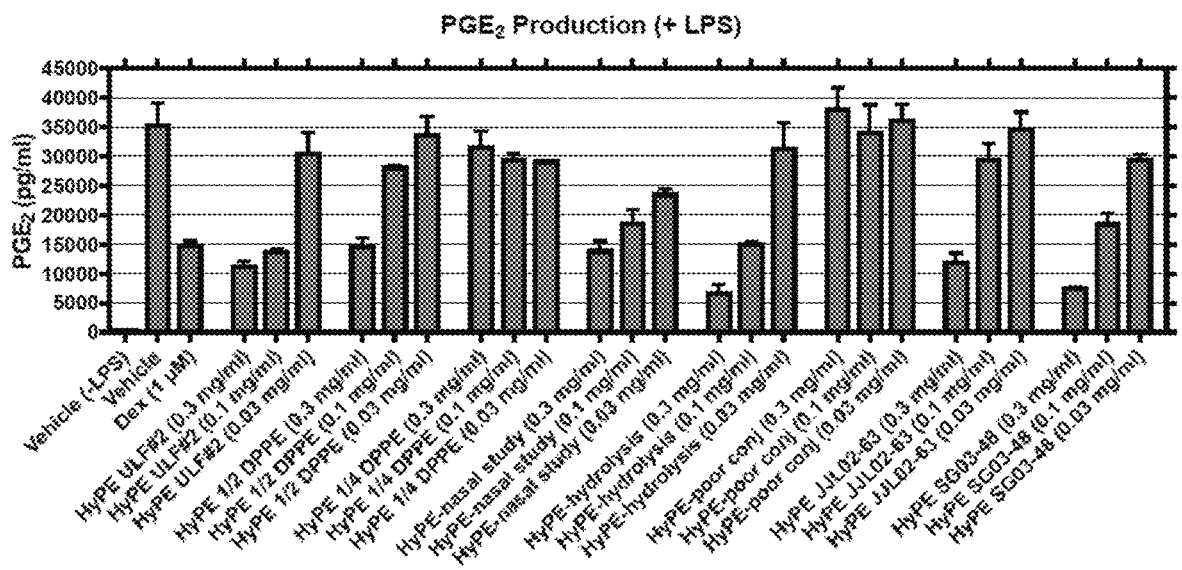
FIG. 14 depicts the mean $PGE_2$ release from LPS-stimulated RAW 264.7 cells. Error bars represent standard deviations.
Figure 18:
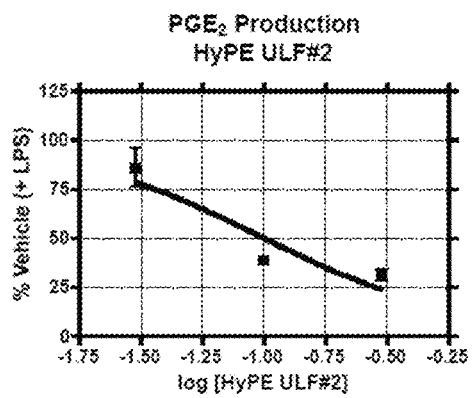
FIG. 18 depicts dose-response curves for $PGE_2$ production (+LPS). Data fit using Prism 4, Sigmoidal dose-response curve (variable slope): Y=Bottom+(Top+Bottom)/(1+10^((LOGIC50−X)*HillSlope)). X is the log of Test Article concentration, Y is the response. Constraints Bottom=0, Top=100.
Figure 18:
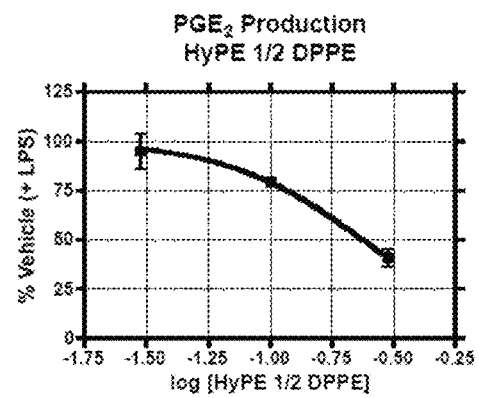
Figure 18:
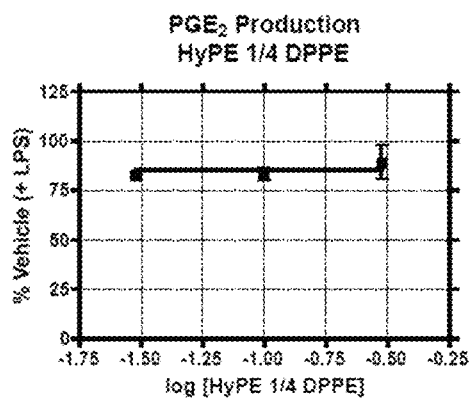
Figure 18:
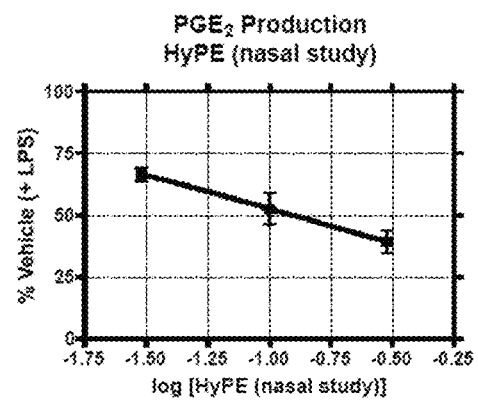
Figure 18:
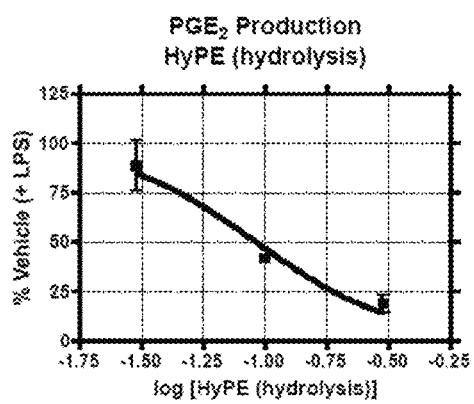
Figure 18:
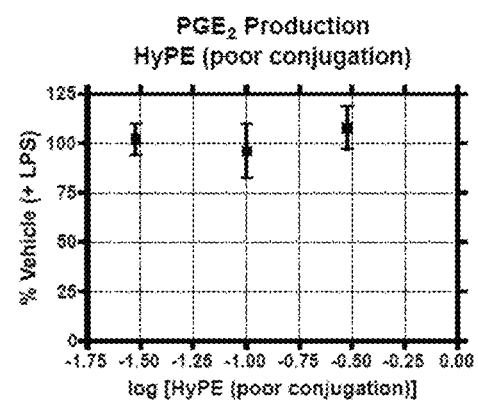
Figure 18:
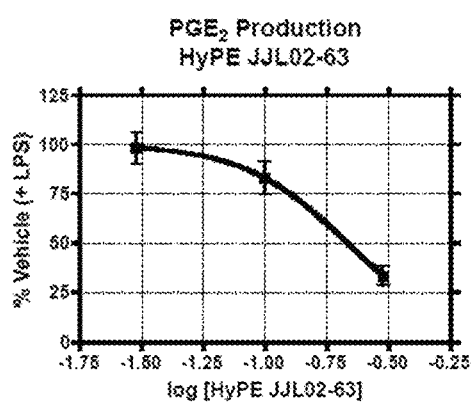
Figure 18:
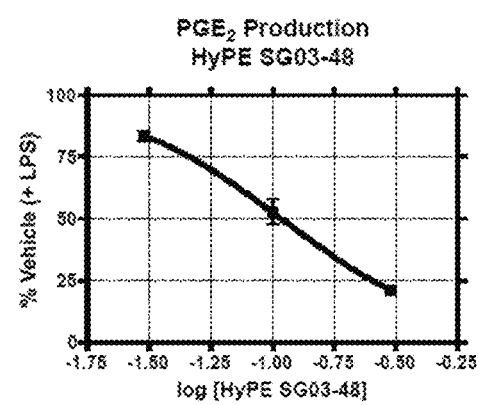
Figure 30:
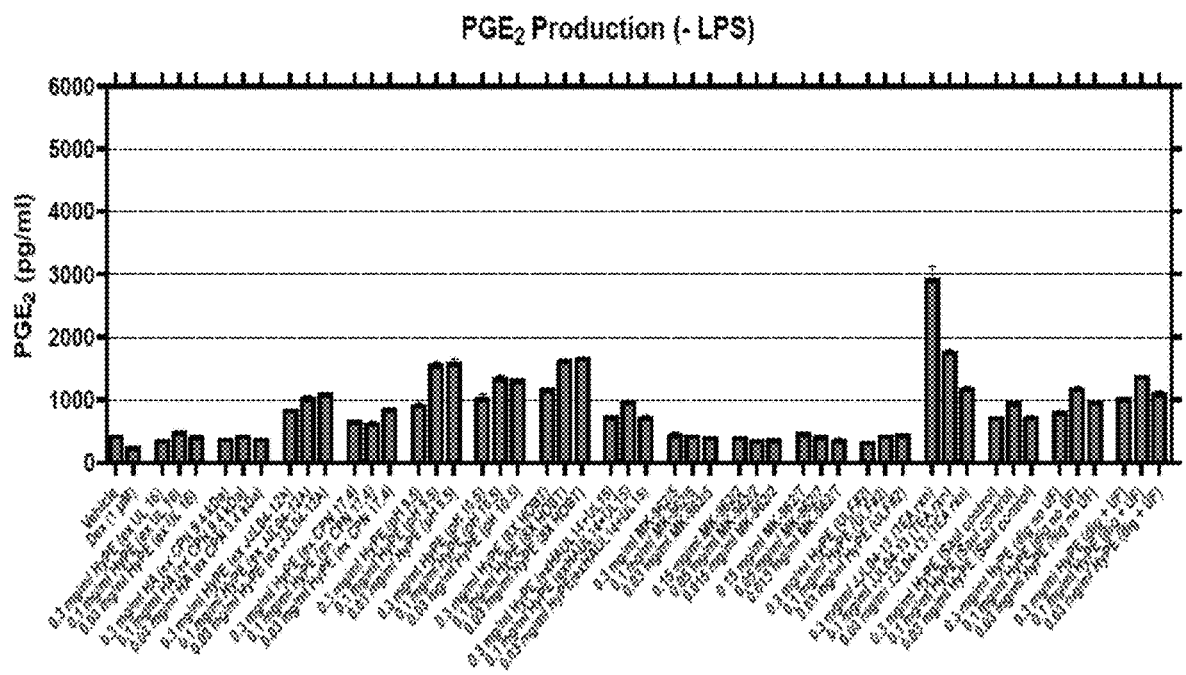
FIG. 30 depicts the mean $PGE_2$ release from RAW 264.7 cells in the absence of LPS. Error bars represent standard deviations.
Figure 31:
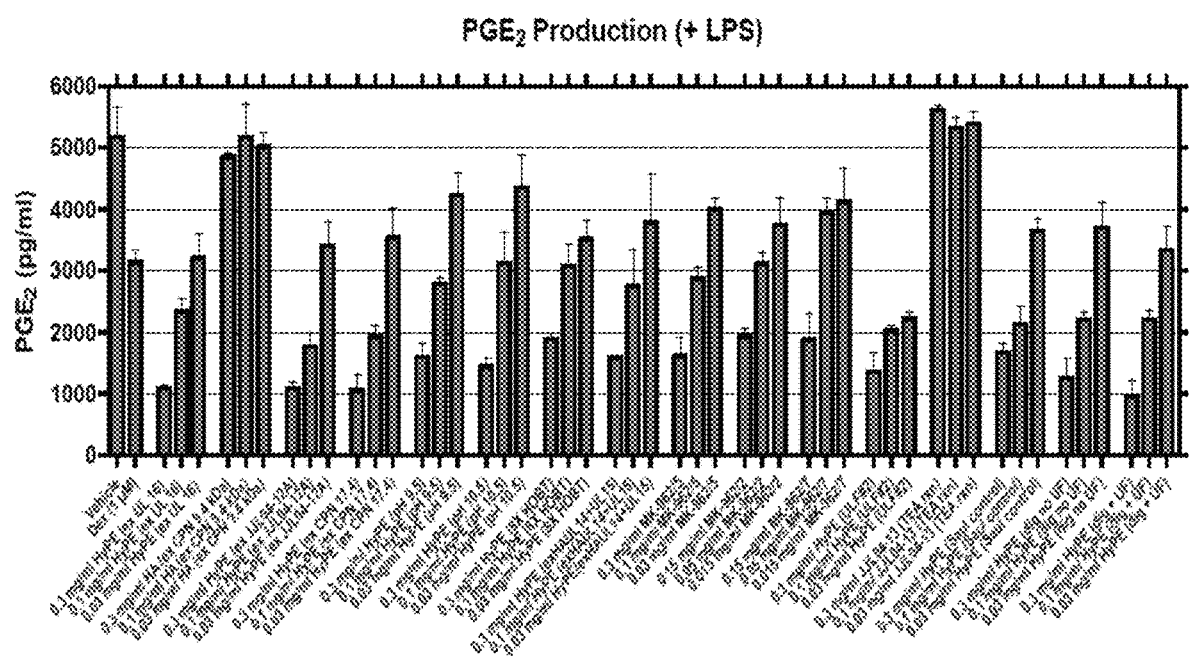
FIG. 31 depicts the mean $PGE_2$ release from LPS-stimulated RAW 264.7 cells. Error bars represent standard deviations.
Figure 35:
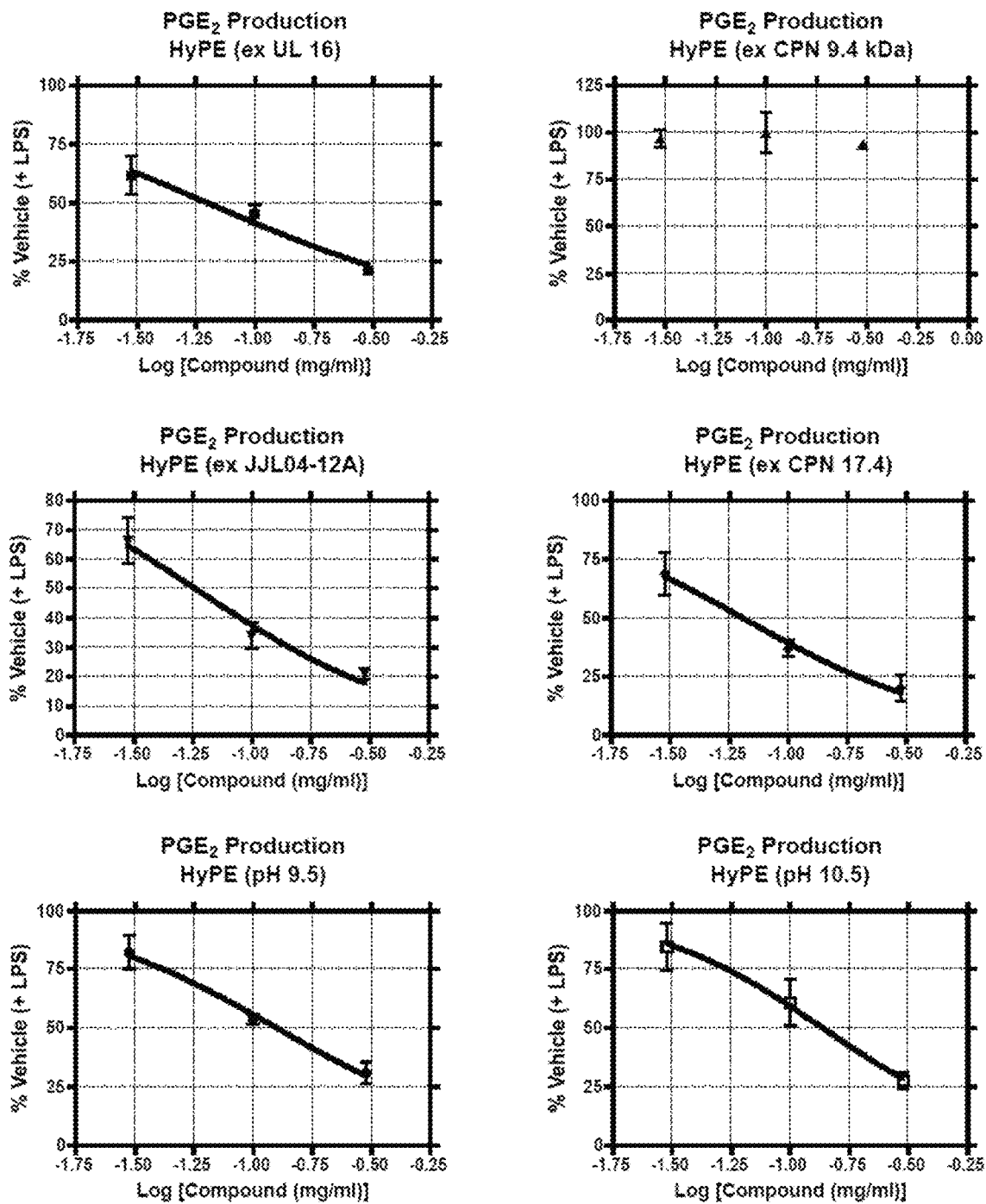
FIG. 35 depicts dose-response curves for $PGE_2$ production (+LPS). Data fit using Prism 4, Sigmoidal dose-response curve (variable slope): Y=Bottom+(Top+Bottom)/(1+10^((LOGIC50−X)*HillSlope)). X is the log of Test Article concentration, Y is the response. Constraints Bottom=0, Top=100.
Figure 35:
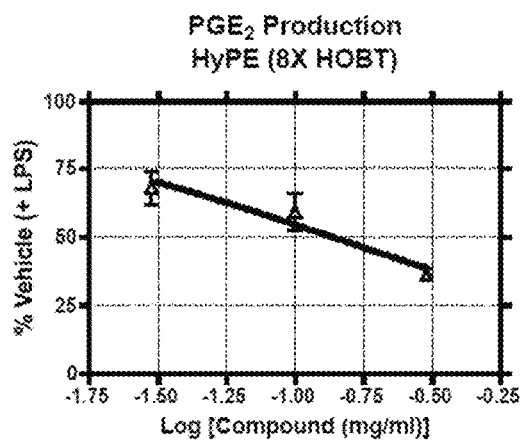
Figure 35:
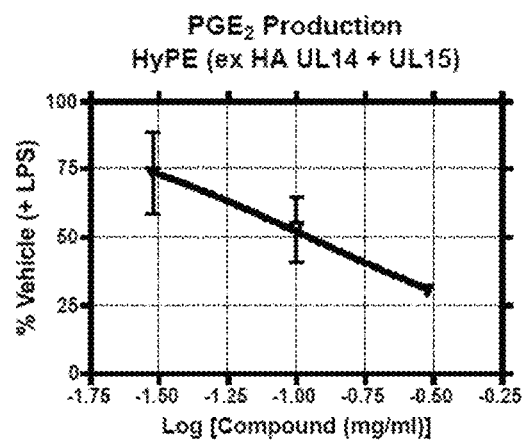
Figure 35:
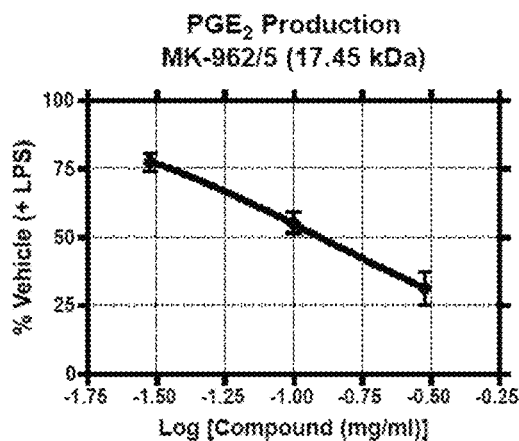
Figure 35:
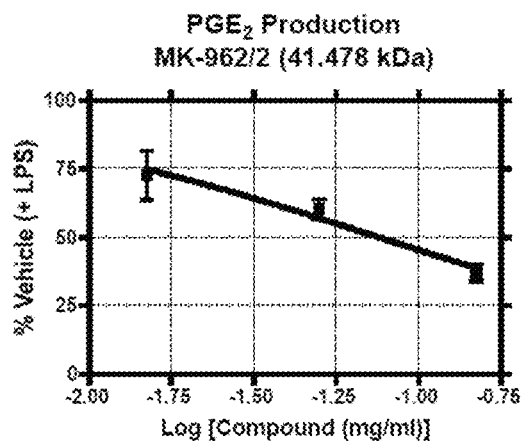
Figure 35:
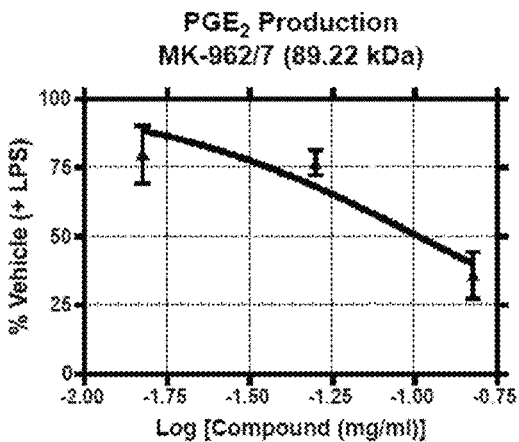
Figure 35:
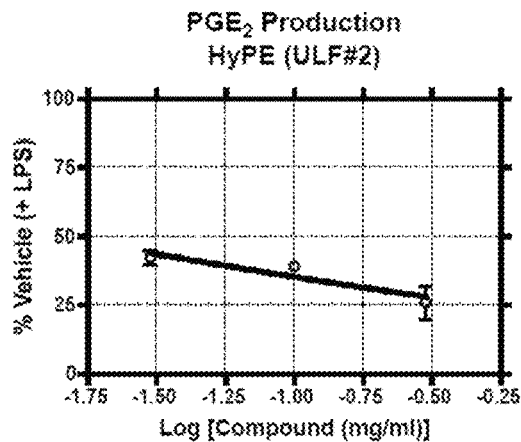
Figure 35:
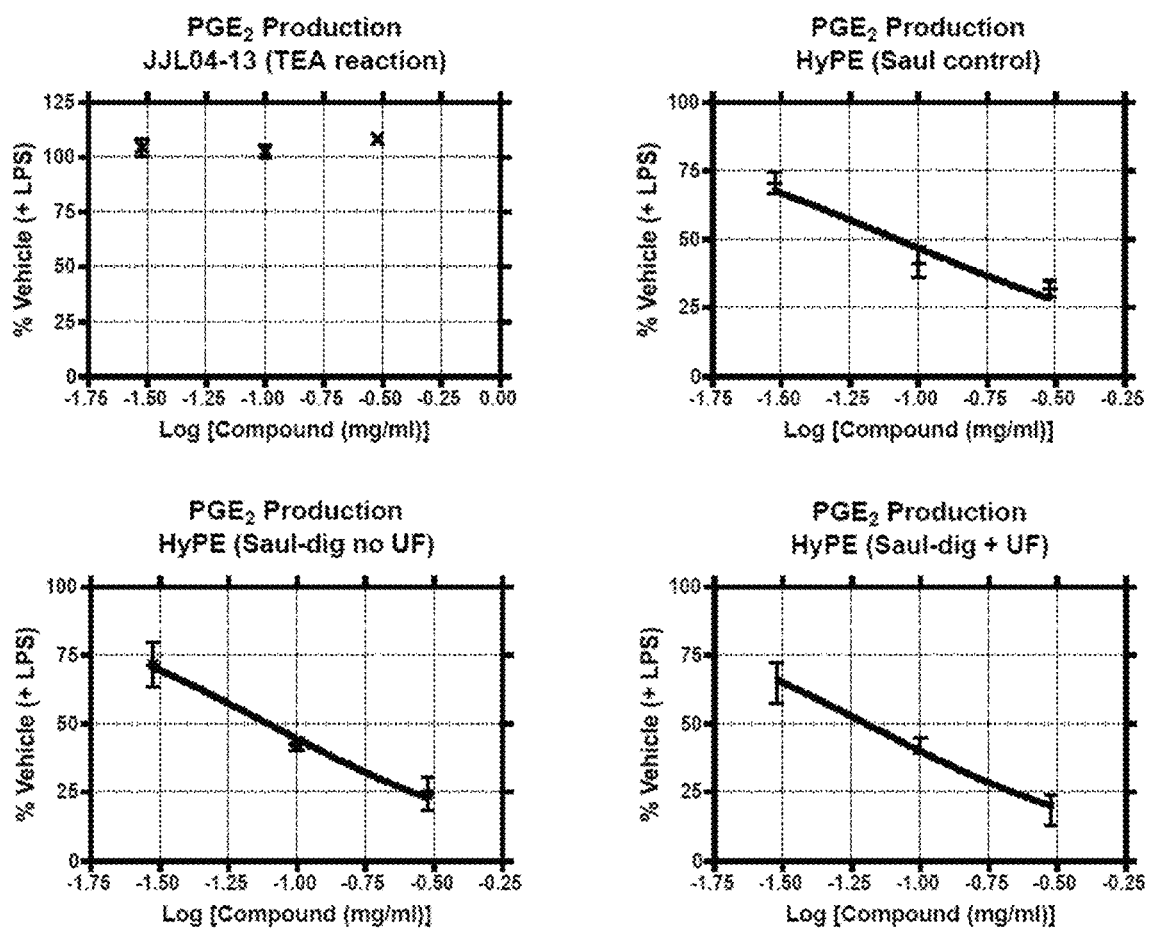

Cell culture supernatants were assayed for $PGE_2$ by ELISA following the manufacturer's instructions. Absorbance readings were detected using a ThermoMax microplate reader (Molecular Devices). Standard curves were generated using a 4-parameter logistic curve fitting equation (SoftMax Pro 4.7.1; Molecular Devices). Each sample reading was interpolated from the appropriate standard curve. Duplicate interpolated sample values were averaged and standard deviations were calculated. Calculated concentrations were multiplied by the appropriate dilution factor. $PGE_2$ data relating to high molecular weight HyPE compositions are shown in FIG. 13, FIG. 14 and FIG. 18. $PGE_2$ data relating to low molecular weight HyPE compositions are shown in FIG. 30, FIG. 31 and FIG. 35.

EXAMPLE 9

Preparation of Low Molecular Weight Sodium Hyaluronate

Raw material of sodium hyaluronate (1.32 MDa) was degraded by acidic hydrolysis. The sample solution was ultrafiltered immediately after degradation. The final product was prepared using spray dryer as in the case of previous samples. In addition it was filtered with 0.2 µm filter (PALL) before drying to achieve microbial purity.

EXAMPLE 10

SEC-MALS Determination of Molecular Weight

The chromatography system (Agilent, 1100 Series) consisted of a HPLC pump (G1310A), an automatic injector (G1313A) and the following column system: PL aquagel-OH Mix and PL aquagel-OH 30 (300×7.5 mm, 8 µm; Agilent Technologies) columns connected in series and thermostated at ambient temperature. Injection volume was 100 µl. Eluent (0.1 M sodium phosphate buffer pH 7.5) was monitored using a DAWN-EOS multi-angle laser light scattering photometer (18-angle, Wyatt Technologies Corporation) and a refractive index detector rEX Optilab (Wyatt Technologies Corporation). Data acquisition and molecular weight calculations were performed using the ASTRA V software, Version 5.3.2.15. The flow rate of mobile phase was maintained at 0.8 ml/min. The specific refractive index increment (dn/dc) of 0.155 mg/ml was used for sodium hyaluronate.

The hyaluronan samples were prepared by dissolving of a weighted amount of sample in the phosphate buffer (concentration 20.0 mg/ml). All samples were stirred several hours. The solutions were filtered through syringe filter (0.2 μm, 25 mm diameter, Whatman) and analysed by HPLC system.

Light scattering measurements can provide an absolute measurement of molar mass when used in series with a concentration sensitive detector such as a refractive index detector and if the value of dn/dc (differential refractive index increment) is known.

In essence, light scattering measurements automatically provide a column calibration curve for every sample, obviating time-consuming, conformation dependent calibration procedure.

Known dn/dc and known calibration constant of refractive index detector as calculated method were used. Differential refractive index increment (in mL/g) was determined by using the Wyatt Optilab refractometer.

The weight-average molecular weight of hyaluronan was verified by measurements of dextran standard.

The determined molecular weight and polydispersity value for low molecular weight hyaluronic acid were 7.86× 103 g/mol and 1.32 Mw/Mn, respectively. The chromatogram and distribution diagram are stated in FIG. 19 and FIG. 20 whereas red line pertains to light scattering signal and blue line to refractive index signal. FIG. 21 illustrates the UV spectrum.

EXAMPLE 11

Preparation of HyPE from 9.54 kD Hyaluronic Acid

Figure 37:
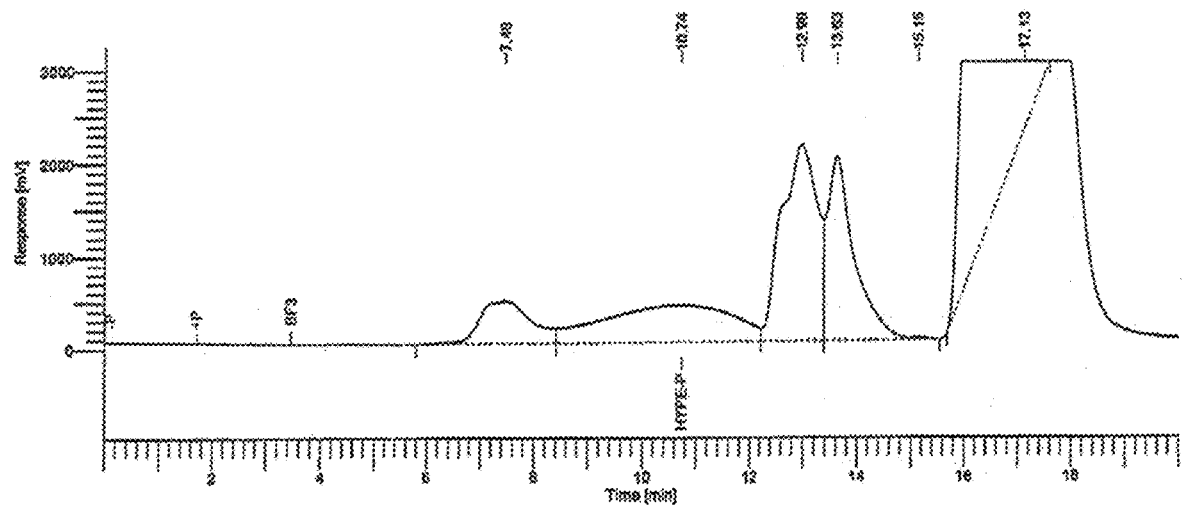
FIG. 37 depicts a chromatogram of the HyPE reaction from Example 11 after 2 hours.
Figure 38:
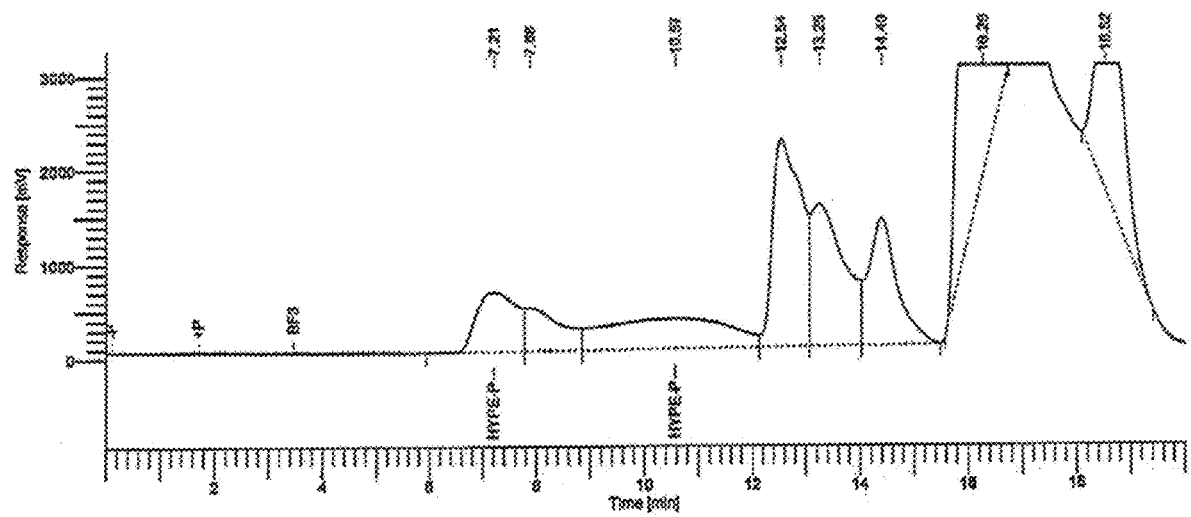
FIG. 38 depicts a chromatogram of the HyPE reaction from Example 11 after 6 hours.
Figure 39:
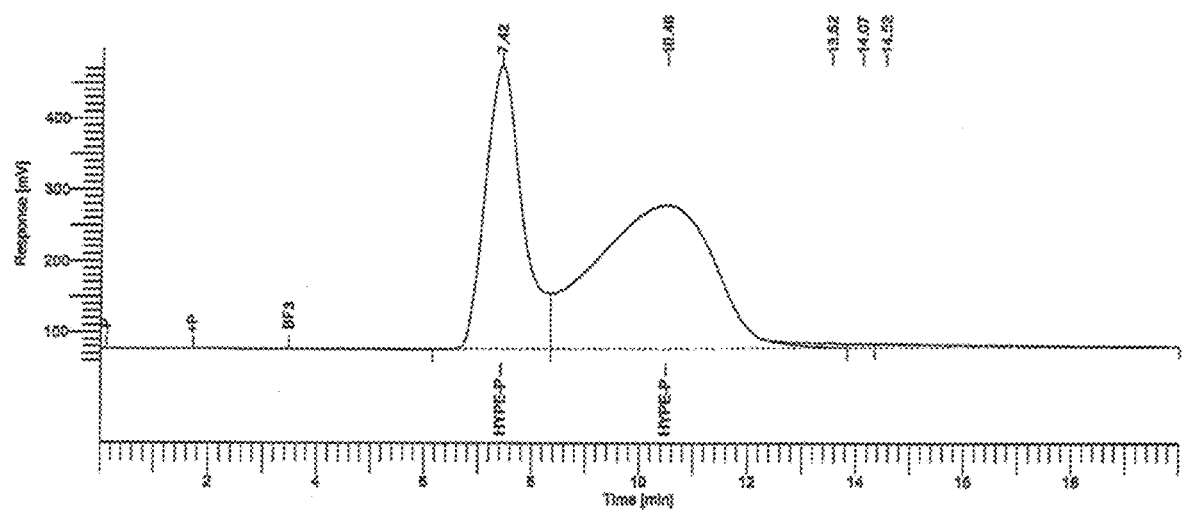
FIG. 39 depicts the GPC analysis of final HyPE isolated from Example 11.
Figure 40:
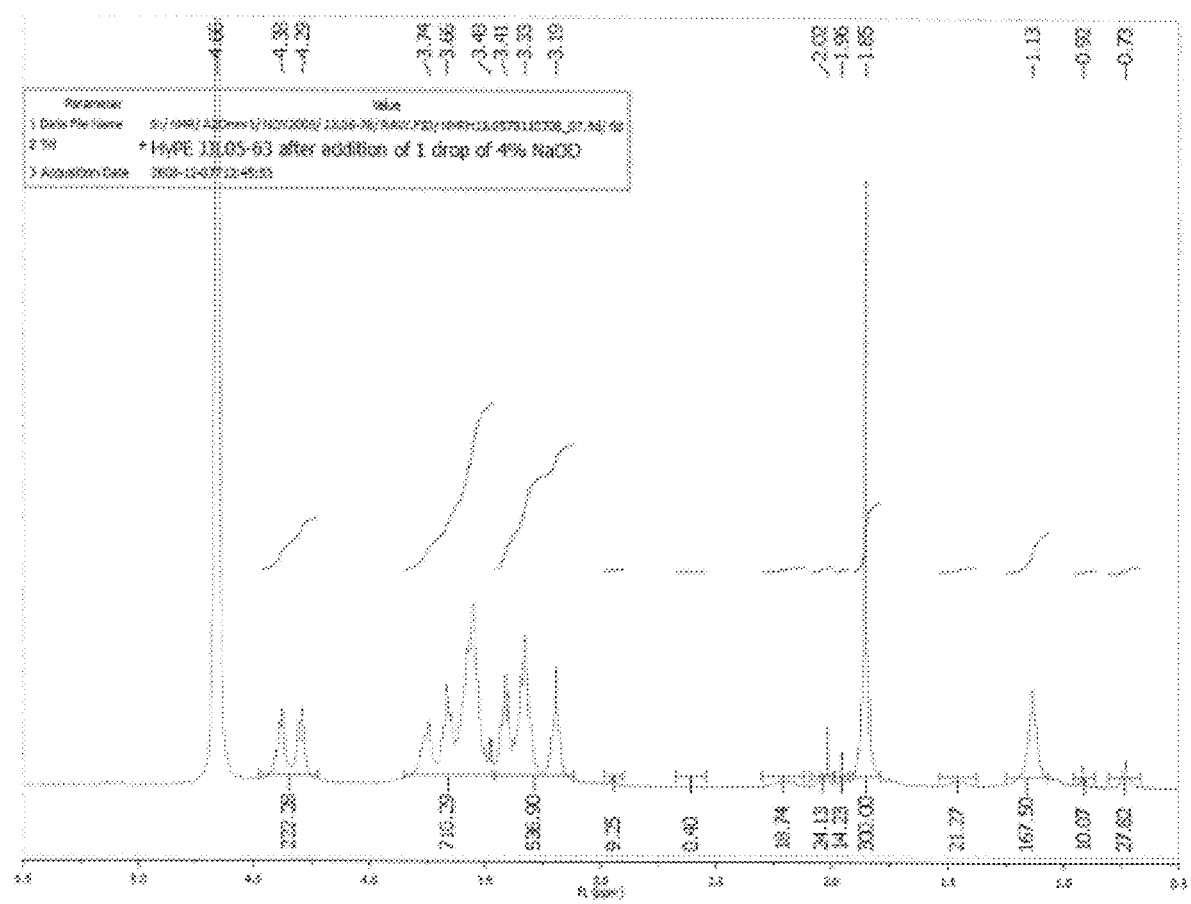
FIG. 40 depicts the NMR spectrum of final HyPE isolated from Example 11 and treated with 1 drop of 4% NaOD.

MES buffer was prepared by dissolving 14.5 g of MES in 75 mL of DI-H$_2$O and adjusting the pH to 6.4 with 4N NaOH. Using an apparatus similar to that depicted in FIG. 1, 10.0 g of HOBT was dissolved in 225 mL of DI-H$_2$O, 60 mL MES buffer, 12 mL of tert-butanol. The pH was adjusted to 6.4 with 4N NaOH. 15.1 g of HA was dissolved in 350 mL of DI-H$_2$O. 1.25 g or DPPE was dissolved in 440 mL of tert-butanol and 90 mL DI-H$_2$O with heating to 55 deg C. The solutions of HA and HOBT were warmed to 35 deg C. and mixed. The DPPE solution, at 50 deg C. was then added to afford a clear solution. This was allowed to cool to 43 deg C., when it was added to the flask and circulated through the sonoreactor system (FIG. 36). Some component of the reaction mixture came out of solution and it was necessary to heat the reaction mixture to 49 deg C. with sonication to form a clear solution. 12.5 g of EDAC was added as a powder to the reaction mixture at a temperature of 45 deg C. Sonication began with a power of 180 watts. The reaction was monitored by GPC as shown in FIGS. 37-38 and because the extent of agglomeration, as observed by the ratio of the area of the first peak to that of the second continued to increase, the reaction was allowed to continue beyond the normal 3 h and was continued the next day. The sonication was turned off and the reaction mixture was filtered through a 0.45 μm filter to remove a small amount of rubber debris apparently from the stator. The solution (1200 mL) was extracted with 600 mL DCM and 600 mL MeOH. The resulting emulsion quickly resolved and the aqueous layer was extracted again with 500 mL DCM and 500 mL EtOH. Finally, the aqueous layer was extracted with 250 mL DCM and 250 mL EtOH and left over the weekend. Residual DCM was removed by rotovaporation at 35 deg C. and 200 Torr. The solution was then transferred to a previously cleaned centrasette ultrafiltration system with a 10 kDa membrane and by constant volume diafiltration was washed with 5 L of 1.5% NaHCO$_3$ to remove residual organic solvents. The pH was then increased by slow addition of 2% Na$_2$CO$_3$ to pH 9.2. The solution was stiffed for 1 hour at room temperature. After further washing with 30 L of 1.5% NaHCO$_3$ the peat at ~12.5 min had disappeared and the solution was washed with 30 L of DI-H$_2$O until pH 7. To remove any digestion/ultrafiltration byproducts, such as free palmitic acid, the solution was then extracted again with 1 L DCM, 1 L MeOH and 0.75 L EtOH. The aqueous layer was extracted again with 400 mL DCM and 50 mL EtOH and finally a third time with 400 mL DCM and 50 mL EtOH. Residual DCM was removed by rotovaporation at 30 deg C. and 200 Torr. By constant volume diafiltration residual MeOH and EtOH were removed by washing with 15 L DI-H$_2$O. The solution was concentrated to 1 L and filtered through a 0.2 μm filter into a lyoguard container and placed in the lyopholizer. It was frozen by lowering the shelf temperature to −70 deg C. When frozen, vacuum was applied (14 mT) and the shelf temperature was raised to 30 deg C. Five days later 6.134 g of HyPE was recovered with a water-corrected weight of 5.2 g which corresponds to a 42% yield based on 12.5 g (water corrected) of HA. Total phosphorus was found to be 0.28% (dry basis). By LC/MS assay, 1,456 ppm of free EDU were found and after exposure to NaOH 12,557 ppm total EDU was found. No HOBT was detected and MES was less than 80 ppm. GPC of the final product is shown in FIG. 39 and NMR data are shown in FIG. 40.

While certain features of the invention have been illustrated and described herein, many modifications, substitutions, changes, and equivalents will now occur to those of ordinary skill in the art. It is, therefore, to be understood that the appended claims are intended to cover all such modifications and changes as fall within the true spirit of the invention.

What is claimed is:

1. A process of making a phospholipid (PL)-glycosaminoglycan (GAG) conjugate wherein said GAG is hyaluronic acid with a molecular weight between 5 to 20 kD and the polydispersity of said hyaluronic acid is from 1.25 to 1.5, said process comprising the steps of obtaining hyaluronic acid, degrading said hyaluronic acid by acid hydrolysis, selecting a hyaluronic acid subpopulation having a molecular weight between 5 to 20 kD by filtration, reacting said hyaluronic acid subpopulation with PL in a sonoreactor at a massPL to massGAG ratio from about 0.25:15 to about 5:15 respectively to produce a reaction mixture containing said PL-GAG conjugate, filtering said resulting reaction mixture to generate a filtrate, and extracting said PL-GAG conjugate from said filtrate.

2. The process of claim 1, wherein said phospholipid is a phosphatidylethanolamine, a phosphatidylserine, a phosphatidylcholine, a phosphatidylinositol, a phosphatidic acid or a phoshpatidylglycerol.

3. The process of claim 1, wherein said phospholipid comprises a palmitic acid or a myristic acid moiety.

4. The process of claim 1, wherein said phospholipid is myristoyl phosphatidylethanolamine or palmitoyl phosphatidylethanolamine.

5. The process of claim 4, wherein said phospholipid is dimyristoyl phosphatidylethanolamine or dipalmitoyl phosphatidylethanolamine.

6. The process of claim 1, wherein said filtration is ultrafiltration.

\* \* \* \* \*